(12) United States Patent
Anderson et al.

(10) Patent No.: US 9,328,104 B2
(45) Date of Patent: May 3, 2016

(54) SELECTIVE ANDROGEN RECEPTOR MODULATORS

(71) Applicant: Pfizer Inc., New York, NY (US)

(72) Inventors: James Thomas Anderson, Hillsdale, NJ (US); Eugene Lvovich Piatnitski Chekler, Concord, MA (US); Edmund L. Ellsworth, Vicksburg, MI (US); Bruce Kipp Erickson, Kalamazoo, MI (US); Adam Matthew Gilbert, Guilford, CT (US); Anthony P. Ricketts, Kalamazoo, MI (US); David P. Thompson, Battle Creek, MI (US); Rayomand Jal Unwalla, Bedford, MA (US); Patrick Robert Verhoest, Newton, MA (US)

(73) Assignee: Pfizer Inc., New York, NY (US)

( * ) Notice: Subject to any disclaimer, the term of this patent is extended or adjusted under 35 U.S.C. 154(b) by 178 days.

(21) Appl. No.: 14/093,812

(22) Filed: Dec. 2, 2013

(65) Prior Publication Data

US 2014/0155390 A1 Jun. 5, 2014

Related U.S. Application Data

(60) Provisional application No. 61/732,617, filed on Dec. 3, 2012.

(51) Int. Cl.
*C07D 207/08* (2006.01)
*C07D 211/22* (2006.01)
(Continued)

(52) U.S. Cl.
CPC ............ *C07D 417/04* (2013.01); *C07C 255/58* (2013.01); *C07C 255/59* (2013.01);
(Continued)

(58) Field of Classification Search
None
See application file for complete search history.

(56) References Cited

U.S. PATENT DOCUMENTS

| 2,482,055 A | 9/1949 | Duggar |
| 2,715,141 A | 8/1955 | Delmar et al. |

(Continued)

FOREIGN PATENT DOCUMENTS

| WO | 91/11172 A1 | 8/1991 |
| WO | 94/02518 A1 | 2/1994 |

(Continued)

OTHER PUBLICATIONS

Almarsson et al, "Crystal engineering of the composition of pharmaceutical phases. Do pharmaceutical co-crystals represent a new path to improved medicines?", ChemComm 17:1889-1896 (2004).

(Continued)

*Primary Examiner* — Zinna Northington Davis
(74) *Attorney, Agent, or Firm* — A. David Joran

(57) ABSTRACT

The present invention relates to a compound of Formula 1, 2 or 3:

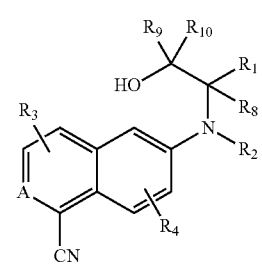

Formula 1

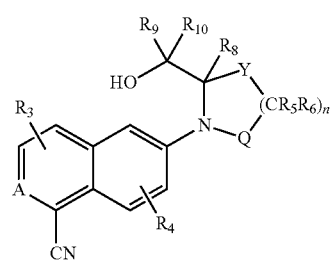

Formula 2

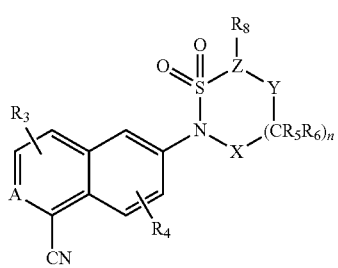

Formula 3 wherein A is N or —$CR_0$—, where $R_0$ is hydrogen, $C_1$-$C_6$ linear or branched chain alkyl, etc., Z is —$CR_e$—, or, —N—, where $R_e$ is hydrogen, $C_1$-$C_6$ linear or branched chain alkyl, etc.; $R_1$ is hydrogen, $C_1$-$C_6$ linear or branched chain alkyl, etc.; $R_2$ are independently hydrogen or $C_1$-$C_6$ linear or branched chain alkyl; $R_3$ and $R_4$ are independently hydrogen, $C_1$-$C_6$ linear or branched chain alkyl, etc.; $R_5$ and $R_6$ are independently hydrogen or $C_1$-$C_6$ linear or branched chain alkyl, etc.; $R_8$ is hydrogen, $C_1$-$C_6$ linear or branched chain alkyl, etc.; $R_9$ and $R_{10}$ are independently hydrogen or $C_1$-$C_6$ linear or branched chain alkyl, etc.; Q is —CO—, —$(CH_2)_q$—, —$(CHR_s)_q$—, or —$(CR_sR_t)_q$—, where $R_s$ and $R_t$ are independently $C_1$-$C_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof, to compositions containing such compounds; and to the uses of such compounds in the treatment of various diseases, particularly, those affected or mediated by the androgen receptor.

13 Claims, No Drawings

(51) Int. Cl.

| | | |
|---|---|---|
| *C07D 217/26* | (2006.01) | |
| *C07D 285/10* | (2006.01) | |
| *C07D 401/04* | (2006.01) | |
| *C07D 417/04* | (2006.01) | |
| *C07C 255/59* | (2006.01) | |
| *C07C 255/58* | (2006.01) | |
| *C07D 205/04* | (2006.01) | |

(52) U.S. Cl.
CPC ............ *C07D205/04* (2013.01); *C07D 207/08* (2013.01); *C07D 211/22* (2013.01); *C07D 217/26* (2013.01); *C07D 285/10* (2013.01); *C07D 401/04* (2013.01)

(56) References Cited

U.S. PATENT DOCUMENTS

| | | |
|---|---|---|
| 3,234,093 A | 2/1966 | Wiechert |
| 3,239,345 A | 3/1966 | Hodge et al. |
| 3,329,709 A | 7/1967 | Schmid et al. |
| 3,332,940 A | 7/1967 | Kirk et al. |
| 3,341,594 A | 9/1967 | Thoma et al. |
| 3,359,287 A | 12/1967 | Babcock et al. |
| 3,377,364 A | 4/1968 | Spero |
| 3,536,712 A | 10/1970 | Keck et al. |
| 3,644,353 A | 2/1972 | Lunts et al. |
| 3,700,681 A | 10/1972 | Barth |
| 3,705,169 A | 12/1972 | Kaiser et al. |
| 3,763,232 A | 10/1973 | Kaiser et al. |
| 3,839,557 A | 10/1974 | Raun |
| 3,919,290 A | 11/1975 | Egger et al. |
| 3,939,265 A | 2/1976 | Grandadam |
| 3,987,194 A | 10/1976 | Baughn et al. |
| 3,995,027 A | 11/1976 | Gale et al. |
| 4,026,897 A | 5/1977 | Nakagawa et al. |
| 4,048,268 A | 9/1977 | Ludwig |
| 4,119,710 A | 10/1978 | Engelhardt et al. |
| 4,138,581 A | 2/1979 | Minatoya et al. |
| 4,154,748 A | 5/1979 | Van Rheenen et al. |
| 4,192,870 A | 3/1980 | Grandadam et al. |
| 4,278,674 A | 7/1981 | Egger et al. |
| 4,283,388 A | 8/1981 | Ose |
| 4,419,364 A | 12/1983 | Olsson et al. |
| 4,900,735 A | 2/1990 | Grandadam |
| 5,248,695 A | 9/1993 | Resemann et al. |
| 5,631,298 A | 5/1997 | Anderson et al. |
| 6,106,864 A | 8/2000 | Dolan et al. |
| 7,534,441 B2 | 5/2009 | McNamara |
| 2002/0132830 A1 | 9/2002 | Morley |

FOREIGN PATENT DOCUMENTS

| | | |
|---|---|---|
| WO | 98/55148 A1 | 12/1998 |
| WO | 00/35298 A1 | 6/2000 |
| WO | 2004/110978 A2 | 12/2004 |
| WO | 2005/018573 A2 | 3/2005 |
| WO | 2009/082437 A2 | 7/2009 |

OTHER PUBLICATIONS

Haleblian, "Characterization of Habits and Crystalline Modification of Solids and Their Pharmaceutical Applications", Journal of Pharmaceutical Sciences 64(8):1269-1288 (1975).

Rautio et al, "Prodrugs: design and clinical applications", Nature Reviews: Drug Discovery 7:255-270 (2008).

Solmssen, "Synthetic Estrogens and the Relation Between Their Structure andn Their Activity", Chemical Reviews 37:481-598 (1945).

Verma et al, "Current Status of Drug Delivery Technologies and Future Directions", Pharmaceutical Technology On-Line 25(2):1-14 (2001).

Manfredi et al, "Synthesis and SAR of tetrahydropyrrolo[1,2-b][1,2,5]thiadiazol-2(3H)-one 1,1-dioxide analogues as highly potent selective androgen receptor modulators", Bioorganic & Medicinal Chemistry Letters 17(16):4487-4490 (2007).

PCT International Search Report and Written Opinion for International Application No. PCT/IB2013/060381 issued Apr. 1, 2014.

SELECTIVE ANDROGEN RECEPTOR MODULATORS

This application claims the benefit of U.S. Provisional Patent Application Ser. No. 61/732,617, filed Dec. 3, 2012.

FIELD OF THE INVENTION

The present invention relates to novel heterocyclic compounds which are effective as selective androgen receptor modulators (SARM). The present invention also relates to compositions comprising selective androgen receptor modulators, and to methods for preparing such compounds. The invention further relates to the use of these compounds to treat diseases or disorders that are related to modulation of the androgen receptor.

BACKGROUND OF THE INVENTION

The androgen receptor ("AR") is a ligand-activated transcriptional regulatory protein that mediates induction of male sexual development and function through its activity with endogenous androgens. Androgenic steroids play an important role in many physiologic processes, including the development and maintenance of male sexual characteristics such as muscle and bone mass, prostate growth, spermatogenesis, and the male hair pattern. The endogenous steroidal androgens include testosterone and dihydrotestosterone ("DHT"). Steroidal ligands which bind the AR and act as androgens (e.g. testosterone enanthate) or as antiandrogens (e.g. cyproterone acetate) have been known for many years and are used clinically.

New compounds are needed which are useful for treating and/or preventing a variety of hormone-related conditions, for example, conditions associated with androgen decline, such as, inter alia, anemia; anorexia; arthritis; bone disease; musculoskeletal impairment; cachexia; frailty; age-related functional decline in the elderly; growth hormone deficiency; hematopoietic disorders; hormone replacement; loss of muscle strength and/or function; muscular dystrophies; muscle loss following surgery; muscular atrophy; neurodegenerative diseases; neuromuscular disease; obesity; osteoporosis; and, muscle wasting.

SUMMARY OF THE INVENTION

The present invention provides compounds of Formula 1, 2 or 3:

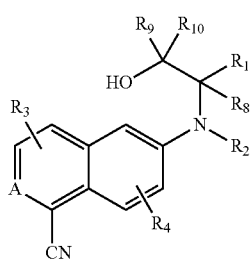

Formula 1

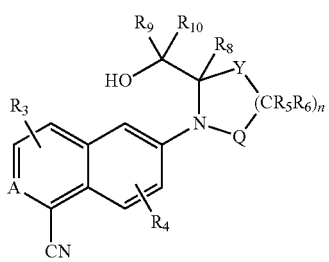

Formula 2

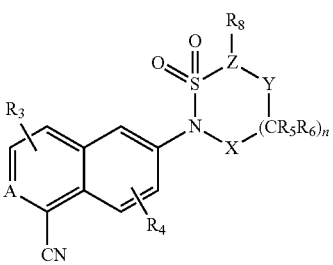

Formula 3 wherein A is N or $-CR_0-$, where $R_0$ is hydrogen, $C_1$-$C_6$ linear or branched chain alkyl, $C_1$-$C_6$ linear or branched chain perfluoroalkyl, aryl, perfluoroaryl, alkylaryl, heteroaryl; or, alkylheteroaryl; X and Y are independently $-CH_2-$, $-CHR_a-$, or, $-CR_aR_b-$, where $R_a$ and $R_b$ are independently $C_1$-$C_6$ linear or branched chain alkyl, aryl, alkylaryl, heteroaryl or, alkylheteroaryl; or, $R_a$ and $R_b$ together form a chain comprising $-(CH_2)_j-$, $-(CHR_c)_j-$, or $-(CR_cR_d)_j-$, where $R_c$ and $R_d$ are independently $C_1$-$C_6$ linear or branched chain alkyl, $C_1$-$C_6$ linear or branched chain perfluoroalkyl, aryl, alkylaryl, heteroaryl or alkylheteroaryl; where j is 2; 3, 4 or 5; Z is $-CR_e-$, or, $-N-$, where $R_e$ is hydrogen, $C_1$-$C_6$ linear or branched chain alkyl, $C_1$-$C_6$ linear or branched chain perfluoroalkyl, aryl, alkylaryl, heteroaryl or, alkylheteroaryl; $R_1$ is hydrogen, $C_1$-$C_6$ linear or branched chain alkyl, aryl, $C_1$-$C_6$ linear or branched chain perfluoroalkyl, alkylaryl, heteroaryl, alkylheteroaryl, $C_1$-$C_6$ linear or branched chain alkoxylcarbonyl, $C_1$-$C_6$ linear or branched chain alkylamino-carbonylamino, $C_1$-$C_6$ linear or branched chain alkyloxycarbonylamino, $C_1$-$C_6$ linear or branched chain alkylcarbonylamino, or, $C_1$-$C_6$ linear or branched chain alkylaminocarbonyl; $R_2$ are independently hydrogen or $C_1$-$C_6$ linear or branched chain alkyl; $R_3$ and $R_4$ are independently hydrogen, $C_1$-$C_6$ linear or branched chain alkyl, $C_1$-$C_6$ linear or branched chain perfluoroalkyl, $C_1$-$C_6$ linear or branched chain perfluoroalkoxy, halogen, cyano, hydroxyl, amino, carboxy, hydroxyl, aryl, heteroaryl, $C_1$-$C_6$ linear or branched chain alkoxylcarbonyl, $C_1$-$C_6$ linear or branched chain alkylamino-carbonylamino, or, $C_1$-$C_6$ linear or branched chain alkylaminocarbonyl; $R_5$ and $R_6$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_5$ and $R_6$ together form a chain comprising $-(CH_2)_k-$, $-(CHR_7)_k-$, or $-(CR_{7a}R_{7b})_k-$, where $R_7$, $R_{7a}$, and $R_{7b}$ are independently $C_1$-$C_6$ linear or branched chain alkyl, $C_1$-$C_6$ linear or branched chain perfluoroalkyl, aryl, alkylaryl, heteroaryl or alkylheteroaryl; where k is 2; 3, 4 or 5; $R_8$ is hydrogen, $C_1$-$C_6$ linear or branched chain alkyl, $C_1$-$C_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising $-(CH_2)_m-$, $-(CHR_f)_m-$, or $-(CR_f$ $R_g)_m$—, where $R_f$ and $R_g$ are independently $C_1$-$C_6$ linear or branched chain alkyl, aryl, alkylaryl, heteroaryl or alkylheteroaryl; where m is 2; 3, 4 or 5; $R_9$ and $R_{10}$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_9$ and $R_{10}$ together form a chain comprising —(CH$_2$)$_p$—, —(CHR$_h$)$_p$—, or —(CR$_h$R$_i$)$_p$—, where R$_h$ and R$_i$ are independently $C_1$-$C_6$ linear or branched chain alkyl, aryl, alkylaryl, heteroaryl or alkylheteroaryl; where p is 2; 3, 4 or 5; Q is —CO—, —(CH$_2$)$_q$—, —(CHR$_s$)$_q$—, or (CR$_s$R$_t$)$_q$—, where R$_s$ and R$_t$ are independently $C_1$-$C_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof.

DETAILED DESCRIPTION OF THE INVENTION

The present invention is related to novel compounds which are selective androgen receptor modulators useful for the treatment of diseases and conditions associated with deficient androgenic and/or anabolic activity. The present invention further provides pharmaceutical compositions comprising such SARMs as well as methods of treating and/or preventing such diseases and conditions. Accordingly, the present invention provides a compound having Formula 1 wherein $R_1$ and $R_2$ are independently $C_1$-$C_6$ linear or branched chain alkyl; and, $R_3$ and $R_4$ are both hydrogen.

In a particular embodiment of the compound having Formula 1, $R_1$ and $R_2$ are independently methyl, ethyl or propyl. In another embodiment of the compound having Formula 2, Q is —(CH$_2$)$_q$—, —(CHR$_s$)$_q$—, or —(CR$_s$R$_t$)$_q$—, where R$_s$ and R$_t$ are independently $C_1$-$C_6$ linear or branched chain alkyl; and, q is 1 or 2. In yet another embodiment of the compound having Formula 2, Q is —CO—.

In a particular embodiment of the compound having Formula 3, X and Y are independently —CH$_2$—, —CHR$_a$—, or, —CR$_a$R$_b$—, where R$_a$ and R$_b$ are independently $C_1$-$C_6$ linear or branched chain alkyl, aryl, alkylaryl, heteroaryl or, alkylheteroaryl. In another embodiment of the compound having Formula 3, X and Y are independently —CH$_2$—, —CHR$_a$—, or, —CR$_a$R$_b$—, where R$_a$ and R$_b$ are independently methyl or ethyl.

In certain specific embodiments, the compound of the present invention is selected from the group consisting of:
6-[(3S)-3-methyl-1,1-dioxido-1,2,5-thiadiazolidin-2-yl]isoquinoline-1-carbonitrile;
6-[(3S)-3-ethyl-1,1-dioxido-1,2,5-thiadiazolidin-2-yl]isoquinoline-1-carbonitrile
6-[(3R)-1,1-dioxido-3-(2,2,2-trifluoroethyl)-1,2,5-thiadiazolidin-2-yl]isoquinoline-1-carbonitrile;
6-[(3R)-1,1-dioxido-3-(2-phenylethyl)-1,2,5-thiadiazolidin-2-yl]isoquinoline-1-carbonitrile;
6-[1-methyl-(3S)-3-methyl-1,1-dioxido-1,2,5-thiadiazolidin-2-yl]isoquinoline-1-carbonitrile;
6-{(3R)-1,1-dioxido-3-[3-(trifluoromethyl)phenyl]-1,2,5-thiadiazolidin-2-yl}isoquinoline-1-carbonitrile;
6-[(3S)-3-(4-chlorophenyl)-1,1-dioxido-1,2,5-thiadiazolidin-2-yl]isoquinoline-1-carbonitrile;
6-[(3S)-3-methyl-1,1-dioxido-1,2-thiazolidin-2-yl]isoquinoline-1-carbonitrile;
6-[(3S)-3-methyl-1,1-dioxido-1,2,5-thiadiazolidin-2-yl]naphthalene-1-carbonitrile;
6-[(4R)-4-methyl-1,1-dioxido-1,2,6-thiadiazinan-2-yl]isoquinoline-1-carbonitrile;
6-[(4S)-4-methyl-1,1-dioxido-1,2,6-thiadiazinan-2-yl]isoquinoline-1-carbonitrile;
6-{(3R)-1,1-dioxido-3-(3-phenyl)-1,2,5-thiadiazolidin-2-yl}isoquinoline-1-carbonitrile;
6-(4,4-dimethyl-1,1-dioxido-1,2,6-thiadiazinan-2-yl)isoquinoline-1-carbonitrile;
6-(6,6-dioxido-6-thia-5,7-diazaspiro[2.5]oct-5-yl)isoquinoline-1-carbonitrile;
6-[(4R)-4-(3-methylbenzyl)-1,1-dioxido-1,2,6-thiadiazinan-2-yl]isoquinoline-1-carbonitrile;
6-[(4R)-6-ethyl-4-methyl-1,1-dioxido-1,2,6-thiadiazinan-2-yl]isoquinoline-1-carbonitrile;
6-(5-methyl-1,1-dioxido-1,2,6-thiadiazinan-2-yl)isoquinoline-1-carbonitrile;
6-[(4S)-4-(4-methylphenyl)-1,1-dioxido-1,2,6-thiadiazinan-2-yl]isoquinoline-1-carbonitrile;
6-[(4R)-4-(4-methylphenyl)-1,1-dioxido-1,2,6-thiadiazinan-2-yl]isoquinoline-1-carbonitrile;
6-[(4S)-4-(3-methylphenyl)-1,1-dioxido-1,2,6-thiadiazinan-2-yl]isoquinoline-1-carbonitrile;
6-[(4S)-4-ethyl-1,1-dioxido-1,2,6-thiadiazinan-2-yl]isoquinoline-1-carbonitrile; and,
6-(1,1-dioxido-4-propyl-1,2,6-thiadiazinan-2-yl)isoquinoline-1-carbonitrile, or a pharmaceutically acceptable salt thereof.

In certain specific embodiments, the compound of the present invention is selected from the group consisting of:
6-{[(2R,3S)-4,4,4-trifluoro-3-hydroxybutan-2-yl]amino}isoquinoline-1-carbonitrile;
6-{(2R)-2-[(1R)-2,2,2-trifluoro-1-hydroxyethyl]azetidin-1-yl}isoquinoline-1-carbonitrile;
6-{(2S)-2-[(1S)-2,2,2-trifluoro-1-hydroxyethyl]azetidin-1-yl}isoquinoline-1-carbonitrile;
6-{methyl[(2R,3R)-4,4,4-trifluoro-3-hydroxybutan-2-yl]amino}isoquinoline-1-carbonitrile;
6-{methyl[(2R,3S)-4,4,4-trifluoro-3-hydroxybutan-2-yl]amino}isoquinoline-1-carbonitrile;
6-{(2R)-2-[(1R)-2,2,2-trifluoro-1-hydroxyethyl]piperidin-1-yl}isoquinoline-1-carbonitrile;
6-{(2R)-2-[(1S)-2,2,2-trifluoro-1-hydroxyethyl]piperidin-1-yl}isoquinoline-1-carbonitrile;
6-{(2R,5R)-2-methyl-5-[(1R)-2,2,2-trifluoro-1-hydroxyethyl]pyrrolidin-1-yl}isoquinoline-1-carbonitrile;
6-{(2R,5R)-2-[(1R)-1-hydroxyethyl]-5-methylpyrrolidin-1-yl}isoquinoline-1-carbonitrile;
6-{(5R)-2-oxo-5-[(1S)-2,2,2-trifluoro-1-hydroxyethyl]pyrrolidin-1-yl}isoquinoline-1-carbonitrile;
6-{(5S)-2-oxo-5-[(1S)-2,2,2-trifluoro-1-hydroxyethyl]pyrrolidin-1-yl}isoquinoline-1-carbonitrile;
6-{(2R)-2-[(1R)-2,2,2-trifluoro-1-hydroxyethyl]pyrrolidin-1-yl}isoquinoline-1-carbonitrile;
6-{(2R)-2-[(1S)-2,2,2-trifluoro-1-hydroxyethyl]pyrrolidin-1-yl}isoquinoline-1-carbonitrile;
6-{(2S)-2-[(1S)-2,2,2-trifluoro-1-hydroxyethyl]pyrrolidin-1-yl}isoquinoline-1-carbonitrile;
6-{(2S)-2-[(1R)-2,2,2-trifluoro-1-hydroxyethyl]pyrrolidin-1-yl}isoquinoline-1-carbonitrile;
6-{(2S,5S)-2-methyl-5-[(1S)-2,2,2-trifluoro-1-hydroxyethyl]pyrrolidin-1-yl}isoquinoline-1-carbonitrile;
6-{(2R,5R)-2-[(1S)-1-hydroxyethyl]-5-methylpyrrolidin-1-yl}isoquinoline-1-carbonitrile;
6-((2R,3S)-4,4,4-trifluoro-3-hydroxybutan-2-ylamino)-1-naphthonitrile;
6-((R)-2-((R)-2,2,2-trifluoro-1-hydroxyethyl)azetidin-1-yl)-1-naphthonitrile;
6-((S)-2-((S)-2,2,2-trifluoro-1-hydroxyethyl)azetidin-1-yl)-1-naphthonitrile
6-(methyl((2R,3R)-4,4,4-trifluoro-3-hydroxybutan-2-yl)amino)-1-naphthonitrile;

6-(methyl((2R,3S)-4,4,4-trifluoro-3-hydroxybutan-2-yl)amino)-1-naphthonitrile;
6-((R)-2-((R)-2,2,2-trifluoro-1-hydroxyethyl)piperidin-1-yl)-1-naphthonitrile;
6-((R)-2-((S)-2,2,2-trifluoro-1-hydroxyethyl)piperidin-1-yl)-1-naphthonitrile;
6-((2R,5R)-2-methyl-5-((R)-2,2,2-trifluoro-1-hydroxyethyl)pyrrolidin-1-yl)-1-naphthonitrile;
6-((2R,5R)-2-((R)-1-hydroxyethyl)-5-methylpyrrolidin-1-yl)-1-naphthonitrile;
6-((R)-2-oxo-5-((S)-2,2,2-trifluoro-1-hydroxyethyl)pyrrolidin-1-yl)-1-naphthonitrile;
6-((S)-2-oxo-5-((S)-2,2,2-trifluoro-1-hydroxyethyl)pyrrolidin-1-yl)-1-naphthonitrile;
6-((R)-2-((R)-2,2,2-trifluoro-1-hydroxyethyl)pyrrolidin-1-yl)-1-naphthonitrile;
6-((R)-2-((S)-2,2,2-trifluoro-1-hydroxyethyl)pyrrolidin-1-yl)-1-naphthonitrile;
6-((S)-2-((S)-2,2,2-trifluoro-1-hydroxyethyl)pyrrolidin-1-yl)-1-naphthonitrile;
6-((S)-2-((R)-2,2,2-trifluoro-1-hydroxyethyl)pyrrolidin-1-yl)-1-naphthonitrile;
6-((2S,5S)-2-methyl-5-((S)-2,2,2-trifluoro-1-hydroxyethyl)pyrrolidin-1-yl)-1-naphthonitrile; and,
6-((2R,5R)-2-((S)-1-hydroxyethyl)-5-methylpyrrolidin-1-yl)-1-naphthonitrile, or, a pharmaceutically acceptable salt thereof.

Particularly preferred embodiments include 6-[(3R)-3-methyl-1,1-dioxido-1,2,5-thiadiazolidin-2-yl]isoquinoline-1-carbonitrile, 6-[(3S)-3-methyl-1,1-dioxido-1,2,5-thiadiazolidin-2-yl]isoquinoline-1-carbonitrile, 6-[(4R)-4-methyl-1,1-dioxido-1,2,6-thiadiazinan-2-yl]isoquinoline-1-carbonitrile, 6-[(4S)-4-methyl-1,1-dioxido-1,2,6-thiadiazinan-2-yl]isoquinoline-1-carbonitrile, and 6-(methyl-((2R,3R)-4,4,4-trifluoro-3-hydroxybutan-2-yl)amino)-1-naphthonitrile, or a pharmaceutically acceptable salt thereof.

The present invention also provides a pharmaceutical composition comprising: a compound having Formula 1, 2 or 3, or a pharmaceutically acceptable salt thereof; and, a pharmaceutical acceptable carrier. The present invention also provides a method for modulating an activity of an androgen receptor in a subject in need thereof, comprising contacting said androgen receptor with an effective amount of a compound having Formula 1, 2 or 3, thereby modulating the activity of said androgen receptor.

The present invention also provides a method of treating a disorder or condition related to dysregulation of androgen receptor in a subject, comprising administering to the subject a therapeutically effective amount of the compound having Formula 1, 2 or 3. In certain embodiments, the disorder or condition treated by the method is selected from among anemia; anorexia; arthritis; bone disease; musculoskeletal impairment; cachexia; frailty; age-related functional decline in the elderly; growth hormone deficiency; hematopoietic disorders; hormone replacement; loss of muscle strength and/or function; muscular dystrophies; muscle loss following surgery; muscular atrophy; neurodegenerative diseases; neuromuscular disease; obesity; osteoporosis; and, muscle wasting.

Compounds of the present invention can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given; other process conditions can also be used unless otherwise stated. Optimum reaction conditions can vary with the particular reactants or solvent used. Those skilled in the art will recognize that the nature and order of the synthetic steps presented can be varied for the purpose of optimizing the formation of the compounds described herein.

Accordingly, the general reaction schemes provided herein illustrate the preparation of the compounds of the invention. Unless otherwise indicated, the substituent variables used in the reaction schemes and the accompanying discussion are defined as indicated above.

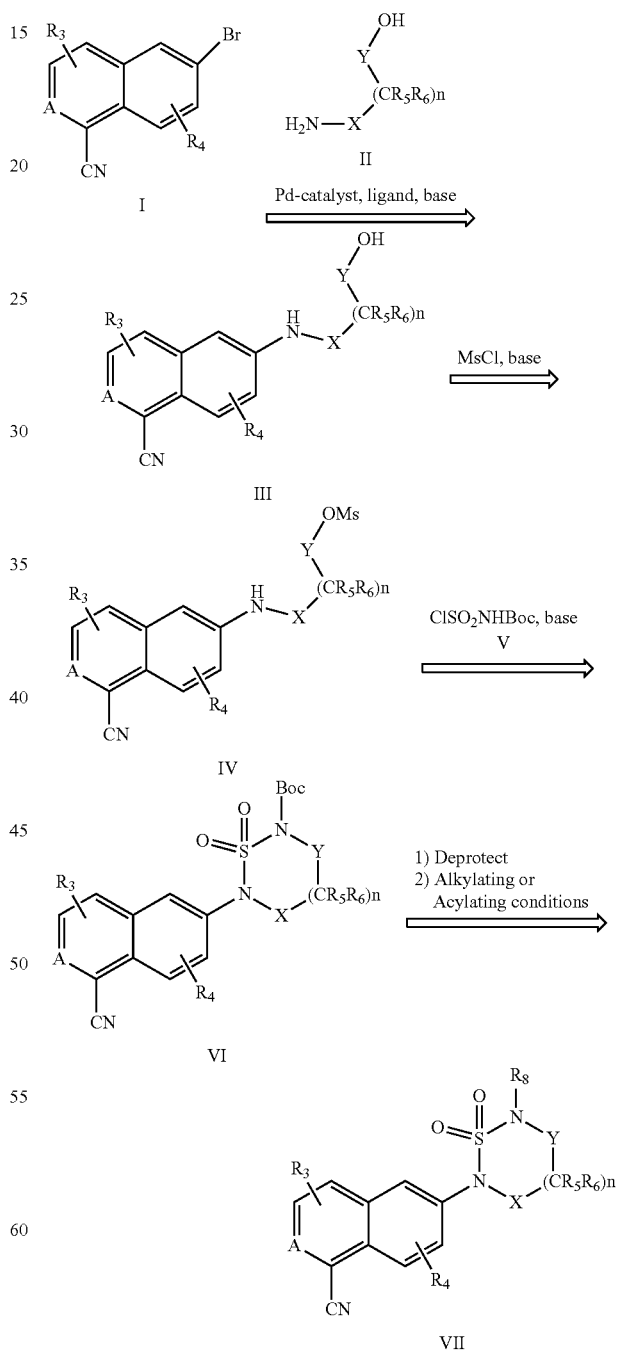

Bromides of general formula I are coupled with aminoalcohols II under coupling conditions such as Pd-catalyzed coupling conditions. The hydroxyl groups of compounds III are activated as leaving groups by mesylate formation among other methods in the presence of a base to generate compounds IV. The treatment of compounds IV with the reagent V produces Boc-protected intermediates VI. Boc-group deprotection followed by alkylation or acylation of intermediate NH compounds culminates the synthesis of a chemical class of compounds of general formula VII. The preparation of products VII with $R_3$ and $R_4$ being unprotected amino, hydroxyl or carboxylic acid groups would require protection of the corresponding functionality using standard methods of organic chemistry and de-protection in the appropriate point in the synthetic sequence.

The preparation of compounds with A being carbon is exemplified by the synthesis of 6-[(3S)-3-methyl-1,1-dioxido-1,2-thiazolidin-2-yl]isoquinoline-1-carbonitrile (Example 8).

When Z (Formula 3) is not equal to N, an alternative procedure to the one described above should be applied. The preparation of compounds with A being carbon is exemplified by the synthesis of 6-[(3S)-3-(4-chlorophenyl)-1,1-dioxido-1,2,5-thiadiazolidin-2-yl]isoquinoline-1-carbonitrile.

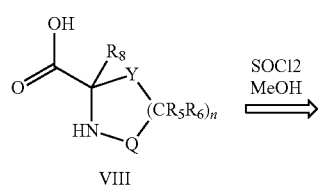

VIII

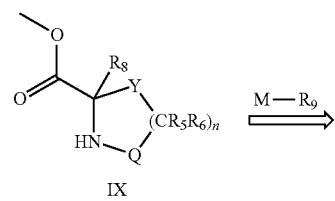

IX

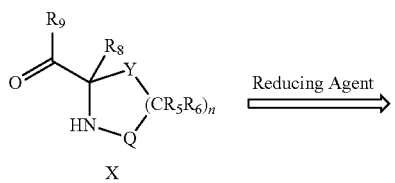

X

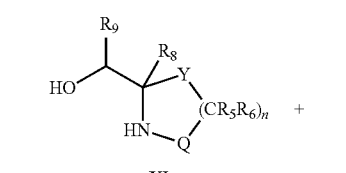

XI

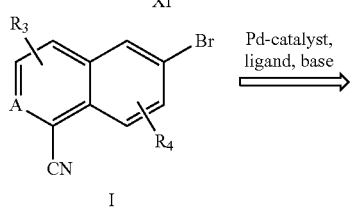

I

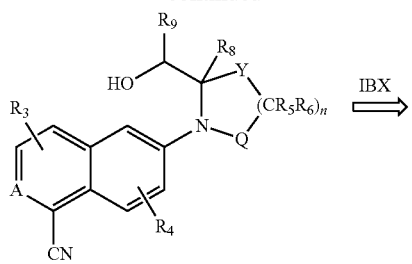

XII

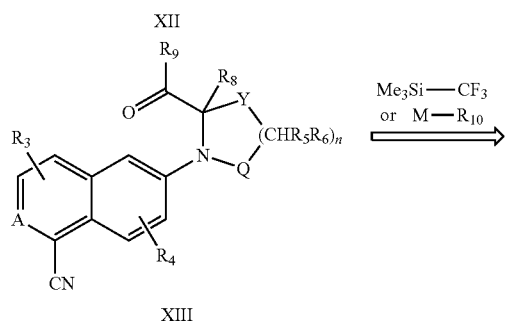

XIII

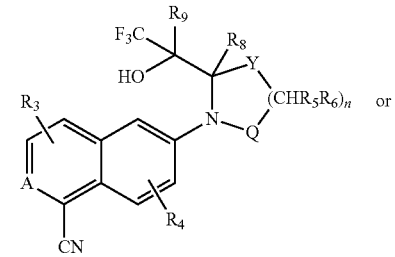

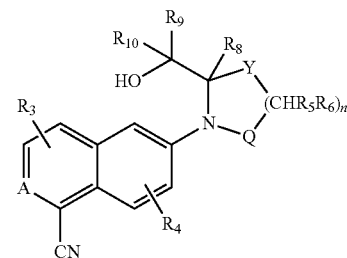

XIV

Aminoacids VIII are converted into methyl esters IX via a standard acid chloride formation protocols. The esters IX undergo transformations into a corresponding ketones (or aldehydes) X using a nucleophilic reagents M-$R_9$ that deliver fragments $R_9$. An alternative approach to produce ketones X would be to employ functional equivalents such as Weinreb amides that are described in the organic chemistry literature. The keto or aldehyde groups are reduced to produce aminoalcohols XI which are coupled with bromide I under Pd-catalyzed conditions. The hydroxyl groups of compounds XII are oxidized to yield a keto or aldehyde compounds XIII which are treated with either $CF_3$-group delivering reagents or with a nucleophilic reagents M-$R_{10}$ that contains fragments $R_{10}$. The product XIV contains $R_{10}$ functionality where $R_{10}$ may be represented by $CF_3$ or another group described in claims. The preparation of products XIV with $R_3$, $R_4$, $R_5$, $R_6$, $R_8$, $R_9$, and $R_{10}$ that contain unprotected NH, OH or COOH groups would require protection of the corresponding functionality using standard methods of organic chemistry and de-protection in the appropriate point in the synthetic sequence.

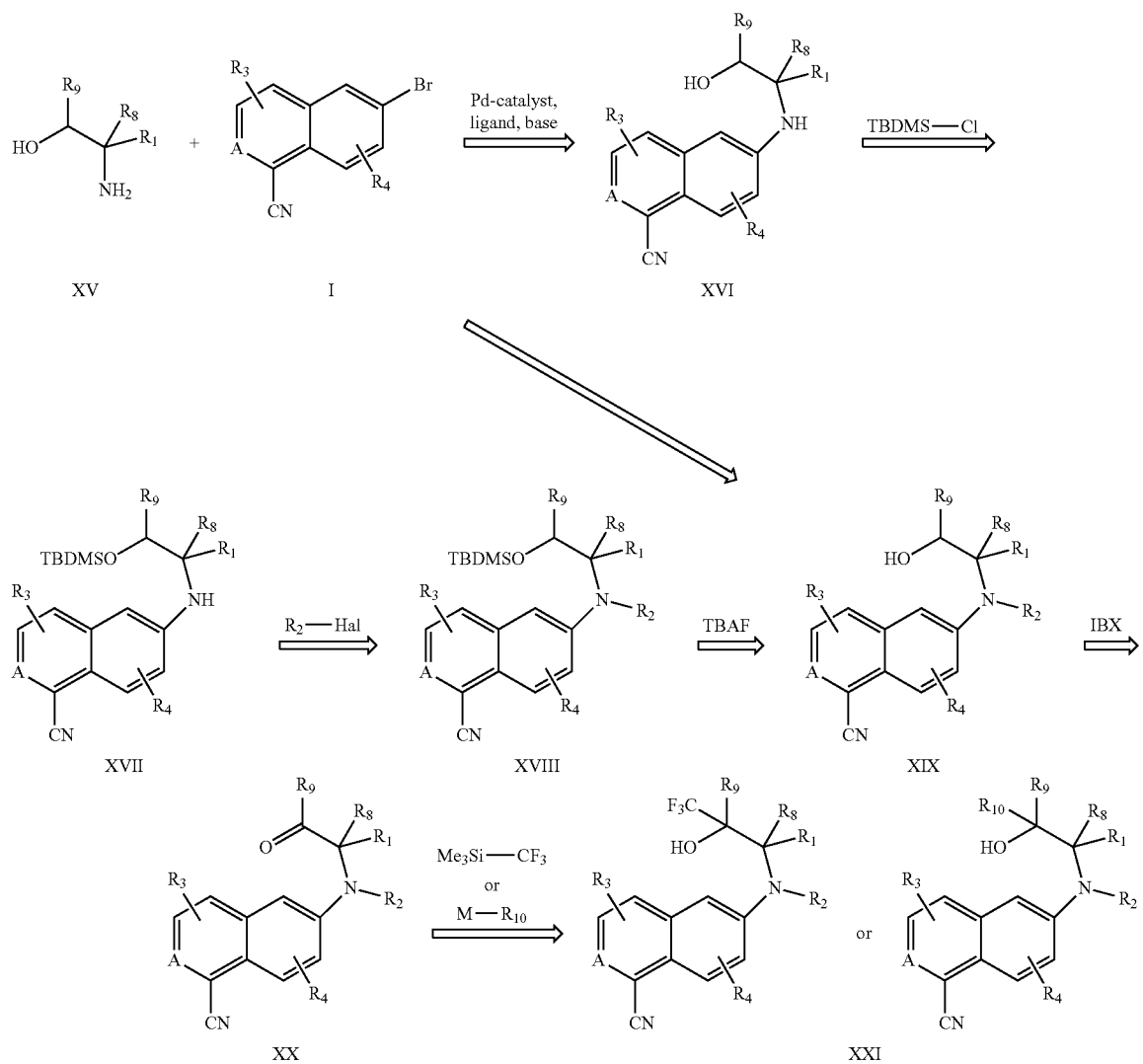

Aminoalcohols XV are coupled with bromides I under coupling conditions such as Pd-catalyzed amide coupling conditions. The hydroxyl groups of XVI are protected with TBDMS or like groups, and NH group of XVII may be modified by incorporation of $R_2$. The protecting groups in XVIII are removed to result in aminoalcohol XIX. The hydroxyl groups of XIX is oxidized to yield a keto or aldehyde compounds XX which are treated with either a $CF_3$- group containing reagent or with nucleophilic reagents $M\text{-}R_{10}$ that contains fragments $R_{10}$. The products XXI contain $R_{10}$ functionality where $R_{10}$ may be represented by $CF_3$ or another group described in claims. The preparation of products XXIII with $R_1$, $R_2$, $R_3$, $R_8$, $R_9$, and $R_{10}$ that contain unprotected NH, OH or COOH groups would require protection of the corresponding functionality using standard methods of organic chemistry and de-protection in the appropriate point in the synthetic sequence.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high-performance liquid chromatography (HPLC), gas chromatography (GC), gel-permeation chromatography (GPC), or thin layer chromatography (TLC).

Preparation of the compounds can involve protection and de-protection of various chemical groups. The chemistry of protecting groups can be found, for example, in Greene et al., *Protective Groups in Organic Synthesis*, 4th. Ed. (John Wiley & Sons, 2007), the entire disclosure of which is incorporated by reference herein for all purposes.

Unless otherwise defined herein, scientific and technical terms used in connection with the present invention have the meanings that are commonly understood by those of ordinary skill in the art. The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment. The term treatment encompasses any objective or subjective improvement in a subject with respect to a relevant condition or disease.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical. The term "heterocyclic" refers to a saturated or partially saturated (i.e. non aromatic) heterocycle which may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "heteroaryl" refers to an aromatic heterocycle which may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The term "oxo" means a double-bonded oxygen. The term "alkoxy" means a radical comprising an alkyl radical that is bonded to an oxygen atom, such as a methoxy radical. Examples of such radicals include methoxy, ethoxy, propoxy, isopropoxy, butoxy and tert-butoxy. The term "halo" means, fluoro, chloro, bromo or iodo.

As used herein, the terms "co-administration", "co-administered" and "in combination with", referring to a combination of a compound of Formula 1, 2 or 3 and one or more other therapeutic agents, includes the following:
a. simultaneous administration of such a combination of a compound of Formula 1, 2 or 3 and a further therapeutic agent to a patient in need of treatment, when such components are formulated together into a single dosage form which releases said components at substantially the same time to said patient,
b. substantially simultaneous administration of such a combination of a compound of Formula 1, 2 or 3 and a further therapeutic agent to a patient in need of treatment, when such components are formulated apart from each other into separate dosage forms which are taken at substantially the same time by said patient, whereupon said components are released at substantially the same time to said patient,
c. sequential administration of such a combination of a compound of Formula 1, 2 or 3 and a further therapeutic agent to a patient in need of treatment, when such components are formulated apart from each other into separate dosage forms which are taken at consecutive times by said patient with a significant time interval between each administration, whereupon said components are released at substantially different times to said patient; and,
d. sequential administration of such a combination of a compound of Formula 1, 2 or 3 and a further therapeutic agent to a patient in need of treatment, when such components are formulated together into a single dosage form which releases said components in a controlled manner.

The term 'excipient' is used herein to describe any ingredient other than a compound of Formula 1, 2 or 3. The choice of excipient will to a large extent depend on factors such as the particular mode of administration, the effect of the excipient on solubility and stability, and the nature of the dosage form. The term "excipient" encompasses diluent, carrier or adjuvant.

One way of carrying out the invention is to administer a compound of Formula 1, 2 or 3 in the form of a prodrug. Thus, certain derivatives of a compound of Formula 1, 2 or 3 which may have little or no pharmacological activity themselves can, when administered into or onto the body, be converted into a compound of Formula 1, 2 or 3 having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, ACS Symposium Series (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs in accordance with the invention can, for example, be produced by replacing appropriate functionalities present in the compounds of Formula 1, 2 or 3 with certain moieties known to those skilled in the art as 'promoieties' as described, for example, in 'Design of Prodrugs' by H. Bundgaard (Elsevier, 1985).

Thus, a prodrug in accordance with the invention is (a) an ester or amide derivative of a carboxylic acid in a compound of Formula 1, 2 or I3; (b) an ester, carbonate, carbamate, phosphate or ether derivative of a hydroxyl group in a compound of Formula 1, 2 or 3; (c) an amide, imine, carbamate or amine derivative of an amino group in a compound form Formula 1, 2 or 3; (d) a thioester, thiocarbonate, thiocarbamate or sulphide derivatives of a thiol group in a compound of Formula 1, 2 or 3; or (e) an oxime or imine derivative of a carbonyl group in a compound of Formula 1, 2 or 3.

Some specific examples of prodrugs in accordance with the invention include:
(i) where the compound of Formula 1, 2 or 3 contains a carboxylic acid functionality (—COOH), an ester thereof, such as a compound wherein the hydrogen of the carboxylic acid functionality of the compound of Formula 1, 2 or 3 is replaced by $C_1$-$C_8$ alkyl (e.g. ethyl) or ($C_1$-$C_8$ alkyl)C(=O)OCH$_2$— (e.g. $^t$BuC(=O)OCH$_2$—);

(ii) where the compound of Formula 1, 2 or 3 contains an alcohol functionality (—OH), an ester thereof, such as a compound wherein the hydrogen of the alcohol functionality of the compound of Formula 1, 2 or 3 is replaced by —CO($C_1$-$C_8$ alkyl) (e.g. methylcarbonyl) or the alcohol is esterified with an amino acid;

(iii) where the compound of Formula 1, 2 or 3 contains an alcohol functionality (—OH), an ether thereof, such as a compound wherein the hydrogen of the alcohol functionality of the compound of Formula 1, 2 or 3 is replaced by ($C_1$-$C_8$ alkyl)C(=O)OCH$_2$— or —CH$_2$OP(=O)(OH)$_2$;

(iv) where the compound of Formula 1, 2 or 3 contains an alcohol functionality (—OH), a phosphate thereof, such as a compound wherein the hydrogen of the alcohol functionality of the compound of Formula 1, 2 or 3 is replaced by —P(=O)(OH)$_2$ or —P(=O)(ONa)$_2$ or P(=O)(O$^-$)$_2$Ca$^{2+}$;

(v) where the compound of Formula 1, 2 or 3 contains a primary or secondary amino functionality (—NH$_2$ or —NHR where R≠H), an amide thereof, for example, a compound wherein, as the case may be, one or both hydrogens of the amino functionality of the compound of Formula 1, 2 or 3 is/are replaced by ($C_1$-$C_{10}$)alkanoyl, —COCH$_2$NH$_2$ or the amino group is derivatized with an amino acid; or, (vi) where the compound of Formula 1, 2 or 3 contains a primary or secondary amino functionality (—NH$_2$ or —NHR where R≠H), an amine thereof, for example, a compound wherein, as the case may be, one or both hydrogens of the amino functionality of the compound of Formula 1, 2 or 3 is/are replaced by CH$_2$OP(=O)(OH)$_2$.

Certain compounds of Formula 1, 2 or 3 may themselves act as prodrugs of other compounds of Formula 1, 2 or 3. It is also possible for two compounds of Formula 1, 2 or 3 to be joined together in the form of a prodrug. In certain circumstances, a prodrug of a compound of Formula 1, 2 or 3 may be created by internally linking two functional groups in a compound of Formula 1, 2 or 3, for instance by forming a lactone.

References below to compounds of Formula 1, 2 or 3 are taken to include the compounds themselves and prodrugs thereof. The invention includes such compounds of Formula 1, 2 or 3 as well as pharmaceutically acceptable salts of such compounds and pharmaceutically acceptable solvates of said compounds and salts.

Pharmaceutically acceptable salts of the compounds of Formula 1, 2 or 3 include acid addition and base salts. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphthalene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula 1, 2 or 3 may be prepared by one or more of three methods:

(i) by reacting the compound of Formula 1, 2 or 3 with the desired acid or base;

(ii) by removing an acid- or base-labile protecting group from a suitable precursor of the compound of Formula 1, 2 or 3 or by ring-opening a suitable cyclic precursor, for example, a lactone or lactam, using the desired acid or base; or, (iii) by converting one salt of the compound of Formula 1, 2 or 3 to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of Formula 1, 2 or 3, and pharmaceutically acceptable salts thereof, may exist in unsolvated and solvated forms. The term 'solvate' is used herein to describe a molecular complex comprising the compound of Formula 1, 2 or 3, or a pharmaceutically acceptable salt thereof, and one or more pharmaceutically acceptable solvent molecules, for example, ethanol. The term 'hydrate' may be employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

Hereinafter, all references to compounds of Formula 1, 2 or 3 include references to pharmaceutically acceptable salts, solvates, multi-component complexes and liquid crystals thereof and to solvates, multi-component complexes and liquid crystals of pharmaceutically acceptable salts thereof.

The compounds of Formula 1, 2 or 3 may exhibit polymorphism and/or one or more kinds of isomerism (e.g. optical, geometric or tautomeric isomerism). The compounds of Formula 1, 2 or 3 may also be isotopically labelled. Such variation is implicit to the compounds of Formula 1, 2 or 3 defined as they are by reference to their structural features and therefore within the scope of the invention.

Compounds of Formula 1, 2 or 3 containing one or more asymmetric carbon atoms can exist as two or more stereoisomers. Where a compound of Formula 1, 2 or 3 contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula 1, 2 or 3 containing, for example, an imino, keto, or oxime group, or so-called valence tautomerism in compounds which contain an aromatic moiety. It follows that a single compound may exhibit more than one type of isomerism.

The pharmaceutically acceptable salts of compounds of Formula 1, 2 or 3 may also contain a counterion which is optically active (e.g. d-lactate or l-lysine) or racemic (e.g. dl-tartrate or dl-arginine). Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1, 2 or 3 contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of Formula 1, 2 or 3 (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). In some relevant examples herein, columns were obtained from Chiral Technologies, Inc, West Chester, Pa., USA, a subsidiary of Daicel® Chemical Industries, Ltd., Tokyo, Japan.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art. *Stereochemistry of Organic Compounds* by E. L. Eliel and S. H. Wilen (Wiley, 1994).

The present invention includes all pharmaceutically acceptable isotopically-labelled compounds of Formula 1, 2 or 3 wherein one or more atoms are replaced by atoms having the same atomic number, but an atomic mass or mass number different from the atomic mass or mass number which predominates in nature. Isotopically-labelled compounds of Formula 1, 2 or 3 can generally be prepared by conventional techniques known to those skilled in the art or by processes analogous to those described in the accompanying Examples and Preparations using an appropriate isotopically-labelled reagent in place of the non-labelled reagent previously employed. In particular, hydrogen atoms may be replaced by deuterium atoms since such deuterated compounds are sometimes more resistant to metabolism.

Also included within the scope of the invention are active metabolites of compounds of Formula 1, 2 or 3, that is, compounds formed in vivo upon administration of the drug, often by oxidation or dealkylation. Some examples of metabolites in accordance with the invention include (i) where the compound of Formula 1, 2 or 3 contains a methyl group, an hydroxymethyl derivative thereof (—$CH_3$→—$CH_2OH$):

(ii) where the compound of Formula 1, 2 or 3 contains an alkoxy group, an hydroxy derivative thereof (—OR→—OH);

(iii) where the compound of Formula 1, 2 or 3 contains a tertiary amino group, a secondary amino derivative thereof (—NRR'→—NHR or —NHR);

(iv) where the compound of Formula 1 contains a secondary amino group, a primary derivative thereof (—NHR→—$NH_2$);

(v) where the compound of Formula 1, 2 or 3 contains a phenyl moiety, a phenol derivative thereof (-Ph→-PhOH); and, (vi) where the compound of Formula 1, 2 or 3 contains an amide group, a carboxylic acid derivative thereof (—$CONH_2$→COOH).

For administration to human patients, the total daily dose of a compound of Formula 1, 2 or 3 is typically in the range of 0.01 mg to 500 mg depending, of course, on the mode of administration. In another embodiment of the present invention, the total daily dose of a compound of Formula 1, 2 or 3 is typically in the range of 0.1 mg to 300 mg. In yet another embodiment of the present invention, the total daily dose of a compound of Formula 1, 2 or 3 is typically in the range of 1 mg to 30 mg. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly.

In the case of dry powder inhalers and aerosols, the dosage unit is determined by means of a prefilled capsule, blister or pocket or by a system that utilizes a gravimetrically fed dosing chamber. Units in accordance with the invention are typically arranged to administer a metered dose or "puff" containing from 1 to 5000 μg of drug. The overall daily dose will typically be in the range 1 μg to 20 mg which may be administered in a single dose or, more usually, as divided doses throughout the day.

A compound of Formula 1, 2 or 3 can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Compounds of Formula 1, 2 or 3 may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of Formula 1, 2 or 3 may also be used in fast-dissolving, fast-disintegrating dosage forms such as those described in Expert Opinion in Therapeutic Patents, 11 (6), 981-986, by Liang and Chen (2001). For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %. In one embodiment of the present invention, lubricants comprise from 0.5 weight % to 3 weight % of the tablet. Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula 1, 2 or 3, a film-forming polymer, a binder, a solvent, a humectant, a plasticizer, a stabilizer or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of Formula 1, 2 or 3 may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques. Compounds of the invention may also be administered topically to the skin or mucosa, that is, dermally or transdermally.

The compounds of Formula 1, 2 or 3 can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound of Formula 1, 2 or 3 comprising, for example, ethanol, aqueous ethanol, or a suitable alternative agent for dispersing, solubilizing, or extending release of the compound, a propellant as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µl to 100 µl. A typical formulation may comprise a compound of Formula 1, 2 or 3, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of Formula 1, 2 or 3 may also be administered directly to the eye or ear, typically in the form of drops of a micronized suspension or solution in isotonic, pH-adjusted, sterile saline.

Compounds of Formula 1, 2 or 3 may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in international patent publications WO-A-91/11172, WO-A-94/02518 and WO-A-98/55148.

Inasmuch as it may be desirable to administer a combination of active compounds, for example, for the purpose of treating a particular disease or condition, it is within the scope of the present invention that two or more pharmaceutical compositions, at least one of which contains a compound of Formula 1, 2 or 3, may conveniently be combined in the form of a kit suitable for co-administration of the compositions. Thus, a kit of the invention comprises two or more separate pharmaceutical compositions, at least one of which contains a compound of Formula 1, 2 or 3, and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid. The novel compounds of the present invention are also useful in the field of veterinary medicine. In addition to use in non-human animals for the uses described hereinabove for human subjects, the compounds of the present invention are also particularly useful in treating non-human animals that are being raised for human food consumption. The dosages and dosage forms described hereinabove for human subjects can be adjusted to accommodate the varying size of animals, as is well known to those of ordinary skill in the veterinary art.

The novel compounds of the present invention are useful in increasing lean mass, reducing fat mass, reducing percent fat mass, and increasing lean:fat when administered to animals.

Thus, the present invention also provides a method of affecting carcass composition, increasing lean mass, reducing fat mass, reducing percent fat mass, increasing lean:fat, increasing average daily gain (ADG), or decreasing feed to gain ratio (F:G) of an animal, or increasing feed efficiency in an animal, wherein the method comprises administering to the animal an effective amount of a compound having Formula 1, 2, or 3, or a pharmaceutically acceptable salt thereof. In one embodiment of this method, the animal is a feedlot animal. In another embodiment of this method, the animal is finishing livestock.

The term "feedlot animal" refers to an animal the meat of which is considered edible in a given culture or country. In some embodiments, such term may include, without limitation, swine (domestic pig, wild boars), bovine (bison, cattle, yaks), cervids (deer, elk, moose), ovine (sheep/lamb), and caprine (goats). A feedlot animal may also be a poultry, such as a chicken or a turkey, that is being raised for meat consumption.

The term "finishing livestock" refers to an animal that is normally fattened for the last few days, weeks or months before processing. In one embodiment, the finishing livestock is a cattle. In another embodiment, the finishing livestock is a swine. In another embodiment, the finishing livestock is a poultry, such as a chicken or a turkey. In one embodiment, the finishing livestock is a farmed fish.

In a preferred embodiment, the animal is a cattle or a swine. The swine may be, for example, a sow, a piglet, a grower pig or a finisher pig. The cattle may be, for example, a beef cattle, a calf post-weaning, a pastured calf, or a cattle in utero.

The phrase "increasing lean mass" generally refers to increasing muscle in an animal, which is considered in many cases a more desirable carcass for human food consumption.

"Reducing fat mass" and "reducing percent fat mass" refer to reduction of fat production in an animal.

The phrase "lean:fat", as for example in "increasing lean:fat" refers generally to the ratio of lean mass in an animal relative to fat mass in the animal. An increased lean:fat in an animal is in many cases considered to produce a carcass that is more desirable for human food consumption.

The phrase "F:G" refers to the ratio of feed input into an animal relative to weight gain (output) in the animal. A decrease in F:G increases productivity from an economic view point.

The invention also provides veterinary compositions for treating animals, particularly non-human animals, to achieve the outcomes (e.g., increased ADG) of the methods described herein, which compositions comprise an effective amount of a compound of Formula 1, 2, or 3, or a pharmaceutically acceptable salt of said compound.

Such compositions can be in any dosage form known to those of ordinary skill in the veterinary arts. In one embodiment, the veterinary composition of the present invention is in a form suitable for oral administration to the animal. In another embodiment, the veterinary composition of the invention is in a form suitable for parenteral administration. In another embodiment, the veterinary composition of the invention is in the form of an implant, for example a controlled-release or sustained-release implant. Other dosage forms known to those of ordinary skill can be used for the veterinary composition, such as suppositories, or topical sprays, creams or ointments.

For oral administration, the veterinary compositions may be in the form of capsules, tablets (including but not limited to coated tablets), boluses, granules, powders, food supplements, or liquid forms, such as oral liquid suspensions or liquid concentrates. Such oral forms may be suitable for administration directly to the animal, or they may be concentrated and suitable for dilution, for example by mixing with, or otherwise incorporating into, animal food or by dissolution into animal drinking water. Such forms are known to those of ordinary skill in the veterinary arts.

Feed compositions and compositions for mixing, blending or otherwise combining with animal food will vary depending on the animal species, but usually contain materials such as, but not limited to, cereals, soybean meal, corn cob meal, corn meal, alfalfa meal, corn grits, sugars, cane molasses, grains and/or ground grains (e.g. corn, soybean), fish flour, bone meal and/or ground bone, and can optionally also have incorporated therein nutrients, for example amino acids, mineral salts, vitamins and/or antioxidants. The compounds of the invention are in one embodiment coated onto or otherwise incorporated into a carrier, for example corn grits, suitable for animal feeding.

Methods for composing veterinary compositions suitable for parenteral administration to an animal are known in the art and can be used for the veterinary compositions of the subject invention. For parenteral administration to animals for veterinary use, compounds of the invention can be admixed with conventional carriers such as mineral oil, corn oil, sesame oil, carbowax, calcium stearate and the like. In one embodiment, such formulations are molded into pellets and administered as an injection or as a slow-release subcutaneous implant. The frequency and/or quantity of the injection can be varied depending on the species, the size of the animal, and the degree of growth promotion, improvement in carcass leanness, or feed efficiency desired.

In the case of poultry, this invention also provides a method of treating a poultry by administration of a SARM, for example, a compound of Formula 1, 2, or 3, or a pharmaceutically acceptable salt thereof, in ovo, for purposes of achieving in the poultry the results (e.g., increase in ADG, increase in muscle growth, decrease in fat production) of the methods described herein. The invention provides a method for treating a poultry, said method comprising in ovo administration of an effective amount of a SARM. The invention also provides a veterinary composition for treating a poultry, said composition in a form for in ovo administration, and said composition comprising an effective amount of a SARM, for example, a compound of Formula 1, 2, or 3, or a pharmaceutically acceptable salt thereof, and a carrier acceptable for in ovo administration. In ovo refers to injection, bath or other formulated delivery systems of various substances into avian eggs. An exemplary in ovo injection system that may be utilized to inject a substance into eggs is the INOVOJECT® automated injection device (Embrex, Inc., Durham, N.C.).

An effective amount of compound of Formula 1, 2, or 3 for the veterinary methods and compositions described herein is an amount that is effective in causing an increase in ADG, lean mass, lean:fat, feed efficiency, or a reduction in fat mass. The effective amount to be administered may vary somewhat depending upon the particular animal species being treated and the particular active ingredient employed, but in general an effective amount is from about 0.1 mg to about 60 mg, preferably from about 0.1 mg to about 30 mg, compound per kg body weight of the animal being treated. In another embodiment, the effective amount is from about 0.3 mg to about 30 mg compound per kg body weight of the animal being treated. This amount (about 0.1 mg to about 60 mg compound/kg animal body weight) is generally an amount administered approximately daily to the animal; however, other dosing frequencies (e.g. one-time, every-two-days, or weekly) are included within the invention.

As an example, in the case of in ovo administration, assuming an embryo weight of from about 1 gram to about 20 grams, an effective amount of the compound to administer will range from about 0.0001 mg to about 1.2 mg. In another embodiment, an effective amount of a compound of Formula 1, 2 or 3 is from about 0.1 to about 20 parts per million (ppm) of total daily feed intake of the animal being treated with the compound.

For in ovo administration of a SARM, preferably, and in one embodiment, the SARM is administered to the egg from about day E0 to about day E18, wherein E0 represents the date the egg is laid.

The invention also provides a method of treating a mammal, preferably a cattle or a swine, by administration of a SARM, for example, a compound of Formula 1, 2, or 3 herein, or a pharmaceutically acceptable salt thereof, to the mammal when the mammal is in utero. Said method of treatment is for purposes of achieving in the mammal the results (e.g., increase in ADG, increase in muscle growth, and/or decrease in fat production) of the methods described herein. It is believed that in utero administration of a SARM, for example, a compound of Formula 1, 2, or 3 herein, or a pharmaceutically acceptable salt thereof, increases the total number of muscle fibers in the mammal. In a mammal, all of the total muscle cells during the life of the mammal are generated in-utero, i.e., pre-birth. After any mammal is born, new muscle cells are not generated. The invention provides a method for treating a mammal, preferably a swine or a cattle, said method comprising in utero administration to the mammal of an effective amount of a SARM. This method increases total muscle cell and muscle fiber number in the mammals. The invention also provides a veterinary composition for treating a mammal, said composition in a form for in utero administration, and said composition comprising an effective amount of a SARM, for example a compound of Formula 1, 2, or 3, or a pharmaceutically acceptable salt thereof, and a carrier acceptable for in utero administration.

In utero administration to a mammal is generally achieved by administering to the mother of the in utero mammal in any of the forms described herein, e.g., oral, parenteral, in-feed, in-water, that would be acceptable for treatment of the mother. In one embodiment, the SARM, for example, the compound of Formula 1, 2, or 3, or a pharmaceutically acceptable salt thereof, is administered to the mother of the in utero mammal from about 5 days to about 75 days post-conception of the mammal. In another embodiment, the SARM is administered to the mother of the mammal, while the mammal is in utero, from about 5 days to about 35 days post-conception of the mammal. In another embodiment, the SARM is administered to the mother of the mammal, while the mammal is in utero, from about 55 days to about 75 days post conception of the mammal. Other stages of in utero development during which a SARM can be administered to the mother of the in utero mammal, as well as the duration and frequency of the treatment, are included within the invention; these development stages, duration and frequency will be determined taking into account such factors known in the art as, for example, the species of the mammal and the size of the mammal.

The novel compounds of the subject invention may also be usefully combined with other active pharmaceutical ingredients known in the veterinary fields. Such combinations may be accomplished by administering a compound of the present invention to an animal, as described herein, in one dosage form or unit, and administering the second active pharmaceutical ingredient to the animal separately, in a separate dosage form or unit. The administration to the animal of the two separate dosage forms may be at the same time or in any order. In another embodiment, the compound of the present invention and the second pharmaceutical ingredient (or additional pharmaceutical ingredients) are combined together in the same dosage form and are administered to the animal together.

In one embodiment, a compound of the present invention is administered to an animal in combination with a beta adrenergic agonist or beta adrenergic modulator. Such combination can advance the objectives of the methods of the present invention, such as increasing ADG and increasing lean:fat and feed efficiency. Examples of beta adrenergic agonists or modulators that can be used in the present invention include, but are not limited to, zilpaterol (see, e.g. U.S. Pat. No. 4,900,735), ractopamine (see, e.g., U.S. Pat. No. 5,631,298), salbutamol (see, e.g., U.S. Pat. No. 3,644,353), and cimaterol (see, e.g., U.S. Pat. No. 5,248,695). Other non-limiting examples of beta adrenergic agonists or modulators that can be used in the invention are hexoprenaline (see, e.g., U.S. Pat. No. 3,329,709), isoprenaline (see, e.g., U.S. Pat. No. 2,715,141), rimiterol (see, e.g., U.S. Pat. No. 3,705,169), isoetharine (see, e.g., DE 638650 (I. G. Farben, 1936)), metaproterenol (see, e.g., U.S. Pat. No. 3,341,594), reproterol (see, e.g. United States Patent Application US2002132830, procaterol (see, e.g., U.S. Pat. No. 4,026,897), carbuterol (see, e.g., U.S. Pat. No. 3,763,232), tulobuterol (see, e.g., DE 2244737), pirbuterol (see, e.g., U.S. Pat. No. 3,700,681), mabuterol (see, e.g., U.S. Pat. No. 4,119,710), bitolterol (see, e.g., U.S. Pat. No. 4,138,581), clenbuterol (see, e.g., U.S. Pat. No. 3,536,712), and bambuterol (see, e.g., U.S. Pat. No. 4,419,364).

In another embodiment, a compound of the present invention can be administered to an animal in combination with an antibiotic, in order to achieve the benefits (e.g. increasing lean mass, increasing ADG). Examples of antibiotics that can be used in the present invention include, but are not limited to, tetracycline (see, e.g., U.S. Pat. No. 2,482,055), oxytetracycline (see, e.g., U.S. Pat. No. 2,482,055), tiamulin (see, e.g. U.S. Pat. Nos. 3,919,290; 3,987,194; and 4,278,674), monensin (see, for example, U.S. Pat. Nos. 3,839,557 and 3,995,027), and tylosin (see for example U.S. Pat. Nos. 4,048,268 and 4,283,388).

In another embodiment, a compound of the present invention can be administered to an animal in combination with a steroid in order to achieve the objectives, such as increased ADG, of the veterinary methods described herein. Examples of steroids that can be used in the present invention include, but are not limited to, melengestrol acetate (see, e.g., U.S. Pat. Nos. 3,332,940; 3,359,287; and 4,154,748), trenbolone acetate (see, e.g., U.S. Pat. No. 3,939,265), zeranol (see, e.g. U.S. Pat. No. 3,239,345), and estradiol, for example Synovex® or Revalor® (see, e.g., U.S. Pat. No. 4,192,870).

The present invention also provides for administration of a SARM, for example a compound of Formula 1, 2, or 3 of the present invention, to an animal that has been castrated, be it by physical means or pharmaceutical means or biopharmaceutical means. Castration is used in the case of swine, particularly boars, in order to reduce, e.g., aggressive behavior and, in some cases, unpalatable boar taint, which is a result of hormone levels, for example testosterone levels, in the animal. The castration reduces the level of the testosterone, thereby reducing the aggression and the boar taint. But, the castration, by virtue of the consequent reduction in certain hormones, also impacts the meat quality of the swine. Hence, the present invention provides administering a SARM, for example a novel compound of the present invention, to a castrated animal, such as a castrated swine, in order to affect the carcass composition of the animal, increase lean mass in the animal, reduce fat mass, reduce percent fat mass, increase lean:fat, increase average daily gain (ADG), or decrease feed to gain ratio (F:G) in the animal.

In one embodiment of the invention, the castration of the animal is a physical castration. In another embodiment of the invention, the castration is by pharmaceutical or biopharmaceutical means. Examples of a biopharmaceutical means of castration include, but are not limited to, vaccines containing antibodies targeting certain hormones such as GnRH (gonadotropin releasing hormone) or LHRH (luteinizing hormone releasing hormone), for example the vaccine Improvac® (see, e.g., U.S. Pat. No. 7,534,441). Other pharmaceutical or biopharmaceutical means of castration include, but are not limited to, diethylstilbestrol (see, e.g., U. V. Solmssen, *Chem. Rev.* 37, 481-598 (1945)), medroxyprogesterone (see, e.g., U.S. Pat. No. 3,377,364), and cyproterone (see, e.g., U.S. Pat. No. 3,234,093).

The entire teachings of all of the patents and published patent applications recited hereinabove are incorporated herein by reference.

All the compounds of Formula 1, 2 or 3 can be made by the specific and general experimental procedures described below in combination with the common general knowledge of one skilled in the art (see, for example, Comprehensive Organic Chemistry, Ed. Barton and Ollis, Elsevier; Comprehensive Organic Transformations: A Guide to Functional Group Preparations, Larock, John Wiley and Sons).

The following non-limiting Preparations and Examples illustrate the preparation of compounds of the present invention.

[1]H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionization (ESI) or atmospheric pressure chemical ionization (APCI). The following abbreviations have been used for common solvents: $CDCl_3$, deuterochloroform; $d_6$-DMSO, deuterodimethylsulfoxide; $CD_3OD$, deuteromethanol; THF, tetrahydrofuran; DCM, dichloromethane; EtOAc, ethyl acetate; MeOH, methanol; DMF, dimethylformamide. 'Ammonia' refers to a concentrated solution of ammonia in water possessing a specific gravity of 0.88. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

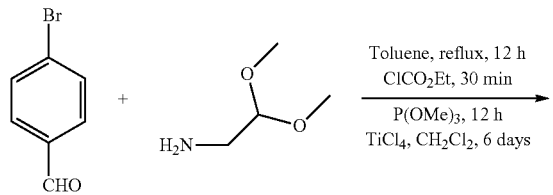

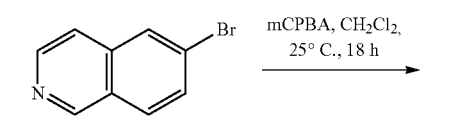

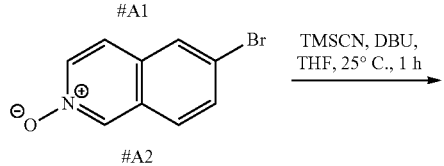

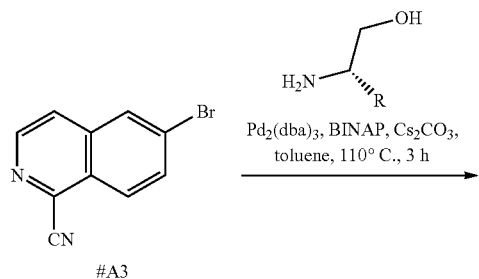

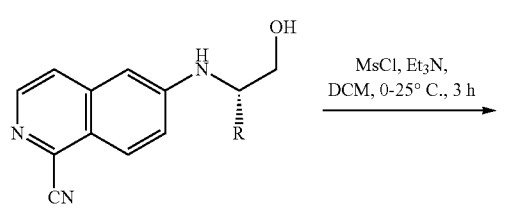

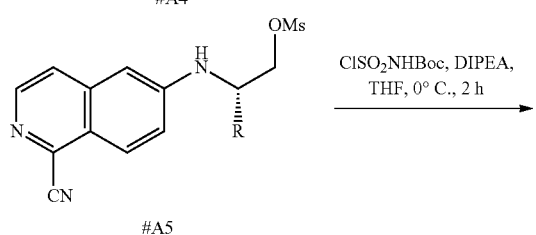

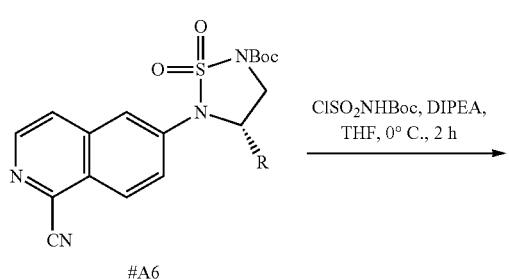

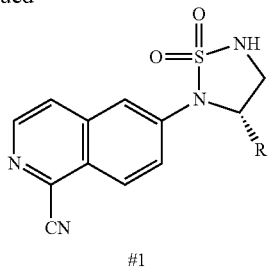

1

Step 1. Synthesis of 6-bromoisoquinoline (#A1). A mixture of 4-bromobenzaldehyde (300.0 g, 1620.0 mmol) and amino acetaldehyde dimethyl acetal (170.4 g, 1620 mmol) in anhydrous toluene (1.5 L) was refluxed under a Dean-Stark condenser for 12 h. The solution was concentrated under vacuum. The residue was dissolved in anhydrous THF and cooled to −10° C. Ethyl chloroformate (193.3 mL, 1782 mmol) was added and stirred for 10 min at −10° C., and then allowed to warm to room temperature. Subsequently trimethyl phosphite (249.6 mL, 1782.0 mmol) was added dropwise to the reaction mixture and stirred for 10 h at room temperature. The solvent was evaporated under vacuum and the residue was dissolved in anhydrous DCM (1.5 L) and stirred for 30 minutes. The reaction mixture was cooled to 0° C., and titanium tetrachloride (1.2 L, 6480 mmol) was added dropwise. The reaction mixture was stirred at 40° C. for 6 days. The reaction mixture was poured into ice and pH was adjusted to 8-9 with aqueous 6N NaOH solution. The suspension was extracted three times with EtOAc. The organic layer was extracted with 3 M HCl. The acidic aqueous solution was adjusted to pH to 7-8 with 3N NaOH solutions and extracted two times with EtOAc. The organic layer was dried over anhydrous sodium sulfate and concentrated under reduced pressure to provide the product. Crude compound was dissolved in minimum amount of DCM and mixed with pentane to get compound #A1 as light brown solid. Yield: 90 g (35%). R$_f$: 0.6 (30% EtOAc in petroleum ether).

LCMS m/z=209 (M+1). $^1$H NMR (400 MHz, d$_6$-DMSO): δ 7.82 (m, 2H), 8.11 (d, J=8.8 Hz, 2H), 8.30 (br s, 1H), 8.56 (d, J=6.0 Hz, 1H), 9.35 (s, 1H).

Step 2. Synthesis of 6-bromoisoquinoline 2-oxide (#A2). m-Chloroperoxybenzoic acid (120.0 g, 720.0 mmol) was added to a solution of #A1 (90.0 g, 480.0 mmol) in DCM (500 mL) at room temperature, and the reaction mixture was stirred for 16 h. 1N NaOH was added to the stirred reaction mixture to adjust the pH to 7-8. The layers were separated and the aqueous layer was extracted with DCM. The organic layer was dried over anhydrous sodium sulfate and concentrated under reduced pressure to render crude product. The solid product was triturated with the mixture of n-pentane and ethanol (8:2) to get the #A2 as white solid. Yield: 65 g (60%). R$_f$: 0.2 (EtOAc).

LCMS m/z=225 (M+1). $^1$H NMR (400 MHz, d$_6$-DMSO): δ 7.83 (m, 2H), 7.91 (d, J=6.8 Hz, 1H), 8.21 (dd, J=8.0, 1.2 Hz, 1H), 8.26 (br s, 1H), 8.97 (s, 1H).

Step 3. Synthesis of 6-bromoisoquinoline-1-carbonitrile (#A3). Trimethylsilyl cyanide (52.0 mL, 580.0 mmol) was added dropwise to the stirred solution of #A2 (65.0 g, 290.0 mmol) and DBU (50.0 mL, 348.0 mmol) in THF (500 mL) at room temperature over a period of 15 minutes. The reaction mixture was stirred at room temperature for 1 h. Water was added to the reaction mixture, and the solution was extracted with DCM. The organic layer was dried over anhydrous Na$_2$SO$_4$ and concentrated under reduced pressure to give crude product. The product was purified by column chromatography using silica gel (100-200 mesh) with 0-4% EtOAc in petroleum ether as an eluent to give #A3 as white solid. Yield: 41 g (61%). $R_f$: 0.6 (30% EtOAc in petroleum ether).

LCMS m/z=233 (M+1). $^1$H NMR (400 MHz, $d_6$-DMSO): δ 8.07 (dd, J=11.2, 2.0 Hz, 1H), 8.21 (m, 2H), 8.55 (br s, 1H), 8.77 (d, J=7.6 Hz, 1H).

A General Procedure to Prepare Intermediates of #A4, #A5, #A6 and #1, #2, #3, #4, #6, #7.

Step 4. A solution of #A3 (1 eq.) in toluene (50 mL) was degassed by bubbling with argon gas for 15 min and then $Pd_2dba_3$ (0.03 eq.), BINAP (0.06 eq.) and $Cs_2CO_3$ (3 eq.) were added to the solution followed by the addition aminoalcohol (2 eq.). The mixture was heated at 100° C. under argon atmosphere for 3 h. Reaction mixture was cooled to room temperature, diluted with EtOAC and washed with water and brine. The organic layer was dried over $Na_2SO_4$ and concentrated to get crude product. The crude compounds were purified by silica gel (100-200 mesh) column chromatography by using 0-5% MeOH in DCM. Yields: 25-45%.

Step 5. MsCl (1 eq.) was added dropwise to a solution of #A4 (1 eq.) and $Et_3N$ (2 eq.) in DCM (10 mL) at 0° C. and was stirred at room temperature for 3 h. The reaction mixture was diluted with DCM, washed with water and brine. The organic layer was dried over $Na_2SO_4$ and concentrated. Crude products were used in next step without further purification.

Step 6. t-Butanol (2 eq.) was slowly added to a solution of chloro sulfonyl isocyanate (2 eq.) in toluene (1 mL/1 mmol) at 0° C. The reaction mixture was stirred at room temperature for 45 min. This solution (t-butyl chlorosulfonylcarbamate) was then added to a solution of #A5 (1 eq.) and DIPEA (4 eq.) in THF and stirred at room temperature for 12 h. Reaction mixture was diluted with water and extracted with EtOAc. Organic layer was washed with water, brine, then dried over anhydrous $Na_2SO_4$ and concentrated. Crude products were purified by silica gel (100-200 mesh) column chromatography using 0-40% EtOAc in petroleum ether.

Step 7. TFA was added to a solution of #A6 (1 eq.) in DCM (8 mL) at 0° C. and stirred at room temperature for 2 h. Reaction mixture was concentrated, diluted with water, neutralized with sat. aq. $NaHCO_3$ soln. then extracted with DCM. The organic layer was washed with water and dried over $Na_2SO_4$ then concentrated. The crude products were purified by triturating with DCM and pentane to provide the compound. In the case of racemic materials, the enantiomers were separated by chiral preparative HPLC.

Column: CHIRALPAK IA, 4.6 mm×250, 5 μm; Mobile phase: n-Hexane: EtOH (65:35) (For X3: 35:65; For X2: 70:30); Flow rate: 1 mL/min; Eluent: EtOH.

Example 1

6-[(3S)-3-methyl-1,1-dioxido-1,2,5-thiadiazolidin-2-yl]isoquinoline-1-carbonitrile (#1; R=CH$_3$)

LCMS m/z=289.1 (M+1). $^1$H NMR (400 MHz, $d_6$-DMSO): δ 1.37 (d, J=6.3 Hz, 3H), 3.27 (m, 1H), 3.74 (m, 1H), 4.63 (m, 1H), 7.17 (d, J=5.7 Hz, 1H), 7.72 (m, 1H), 7.89 (dd, J=10.7, 2.1 Hz, 1H), 8.26 (m, 2H), 8.62 (d, J=5.7 Hz, 1H).

Example 2

6-[(3S)-3-ethyl-1,1-dioxido-1,2,5-thiadiazolidin-2-yl]isoquinoline-1-carbonitrile (Stereochemistry Arbitrarily Assigned) (#2; R=CH$_2$CH$_3$)

LCMS m/z=303.1 (M+1). $^1$H NMR (400 MHz, $d_6$-DMSO): δ 0.92 (t, J=7.4 Hz, 3H), 1.61-1.86 (m, 2H), 3.36 (dd, J=12.6, 4.0 Hz, 1H), 3.67 (dd, J=12.5, 6.5 Hz, 1H), 4.40-4.54 (m, 1H), 7.73 (d, J=2.2 Hz, 1H), 7.89 (dd, J=9.2, 2.3 Hz, 1H), 8.11 (br. s., 1H), 8.17 (d, J=5.7 Hz, 1H), 8.27 (d, J=9.3 Hz, 1H) 8.62 (d, J=5.7 Hz, 1H).

Example 3

6-[(3R)-1,1-dioxido-3-(2,2,2-trifluoroethyl)-1,2,5-thiadiazolidin-2-yl]isoquinoline-1-carbonitrile (Stereochemistry Arbitrarily Assigned) (#3; R=CH$_2$CF$_3$)

LCMS m/z=357.1 (M+1). $^1$H NMR (400 MHz, $d_6$-DMSO): δ 2.72-3.02 (m, 2H), 3.72-3.87 (m, 1H), 4.94-5.06 (m, 1H), 7.76 (d, J=2.2 Hz, 1H), 7.89 (dd, J=9.2, 2.2 Hz, 1H), 8.19 (d, J=5.7 Hz, 1H), 8.28-8.36 (m, 2H), 8.65 (d, J=5.7 Hz, 1H) (additional peak under water peak).

Example 4

6-[(3R)-1,1-dioxido-3-(2-phenylethyl)-1,2,5-thiadiazolidin-2-yl]isoquinoline-1-carbonitrile (Stereochemistry Arbitrarily Assigned) (#4; R=CH$_2$CH$_2$C$_6$H$_5$)

LCMS m/z=379.2 (M+1). $^1$H NMR (400 MHz, $d_6$-DMSO): δ 2.01 (br. s., 2H), 2.63-2.81 (m, 2H), 3.51 (br. s., 1H), 3.71 (d, J=5.4 Hz, 1H), 4.52 (br. s., 1H), 7.10-7.39 (m, 5H), 7.51 (br. s., 1H), 7.85 (d, J=9.1 Hz, 1H), 8.05 (d, J=4.8 Hz, 1H), 8.17-8.33 (m, 2H), 8.62 (d, J=5.1 Hz, 1H).

Example 5

6-[1-methyl-(3S)-3-methyl-1,1-dioxido-1,2,5-thiadiazolidin-2-yl]isoquinoline-1-carbonitrile (#5, R=CH$_3$, N—CH$_3$)

$K_2CO_3$ (2 eq.) and MeI (2 eq.) were added to a solution of #1 (1 eq.) in DMF (3 mL) at 0° C. and stirred at room temperature for 2 h. Reaction mixture was diluted with water. The resulting solid was filtered, washed with water and dried. The crude products were purified by triturating with DCM and pentane to get the pure compound.

LCMS m/z=303.1 (M+1). $^1$H NMR (400 MHz, $d_6$-DMSO): δ 1.34 (d, J=6.1 Hz, 3H), 2.78 (s, 3H), 3.20 (dd, J=10.1, 6.5 Hz, 1H) 3.77 (dd, J=10.2, 6.44 Hz, 1H) 4.68 (q, J=6.3 Hz, 1H) 7.85 (d, J=2.2 Hz, 1H) 7.90 (dd, J=9.2, 2.3 Hz, 1H) 8.21 (d, J=5.6 Hz, 1H) 8.31 (d, J=9.1 Hz, 1H) 8.66 (d, J=5.7 Hz, 1H).

Example 6

6-{(3R)-1,1-dioxido-3-[3-(trifluoromethyl)phenyl]-1,2,5-thiadiazolidin-2-yl}isoquinoline-1-carbonitrile (Stereochemistry Arbitrarily Assigned) (#6; R=m-CF$_3$—C$_6$H$_5$)

LCMS m/z=419.1 (M+1). $^1$H NMR (400 MHz, $d_6$-DMSO): δ 3.41 (dd, J=12.7, 4.8 Hz, 1H), 4.11 (dd, J=12.7, 6.9 Hz, 1H), 5.84 (t, J=5.9 Hz, 1H), 7.61-7.66 (m, 2H), 7.66-7.76 (m, 2H), 7.81 (dd, J=9.2, 2.4 Hz, 1H), 7.88 (s, 1H), 8.07 (d, J=5.8 Hz, 1H), 8.22 (d, J=9.2 Hz, 1H), 8.51 (s, 1H), 8.57 (d, J=5.8 Hz, 1H).

Example 7

6-[(3S)-3-(4-chlorophenyl)-1,1-dioxido-1,2,5-thiadiazolidin-2-yl]isoquinoline-1-carbonitrile (Stereochemistry Arbitrarily Assigned) (#7; R=p-Cl—C$_6$H$_5$)

LCMS m/z=385.6 (M+1). $^1$H NMR (400 MHz, d$_6$-DMSO): δ 4.06 (dd, J=12.5, 6.9 Hz, 1H), 5.70 (t, J=6.1 Hz, 1H), 7.41-7.52 (m, 4H), 7.57 (d, J=2.2 Hz, 1H), 7.78 (dd, J=9.2, 2.3 Hz, 1H), 8.06 (d, J=5.6 Hz, 1H), 8.20 (d, J=9.2 Hz, 1H), 8.43 (br. s., 1H), 8.56 (d, J=5.8 Hz, 1H) (additional peak under water peak).

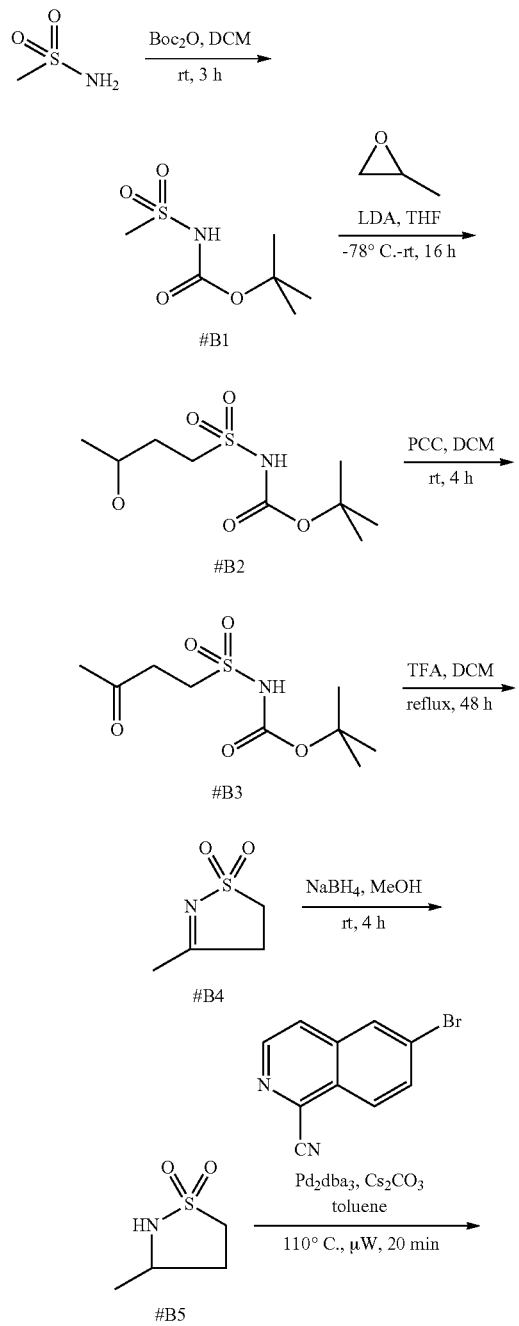

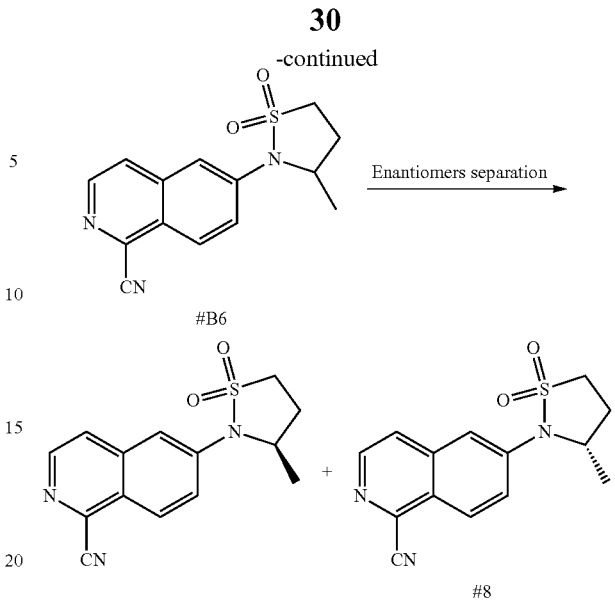

Step 1. Synthesis of tert-butyl methylsulfonylcarbamate (#B1). A solution of Boc$_2$O (41.2 g, 189.2 mmol) in DCM (200 mL) was added dropwise to a stirred suspension of methane sulfonamide (15.0 g, 157.7 mmol), Et$_3$N (23.6 mL, 173.5 mmol) and DMAP (1.9 g, 15.8 mmol) in DCM (200 mL). The resulting suspension was stirred for 3 h at room temperature and concentrated under vacuum. The resulting residue was diluted with EtOAc (300 mL) and acidified with 1 N HCl (200 mL). The organic layer was washed with water followed by brine, dried over Na$_2$SO$_4$ and concentrated under reduced pressure to obtain a crude mixture, which was triturated with 10% EtOAc in petroleum ether to obtain #B1 as a white solid (25.0 g, 81%). R$_f$: 0.6 (50% EtOAc in petroleum ether).

LCMS m/z=194.3 (M−H). $^1$H NMR (400 MHz, CDCl$_3$): δ 1.44 (s, 9H), 3.19 (s, 3H), 7.19 (s, 1H).

Step 2. Synthesis of tert-butyl 3-hydroxybutylsulfonylcarbamate(#B2). Freitag, D., Metz, P. *Tetrahedron* 2006, 62(8), 1799-1805.

n-BuLi (10.2 mL, 1M in hexane, 10.2 mmol) was added to a solution of diisopropylamine (1.7 mL, 10.2 mmol) in THF (20 mL) at −78° C., and the resulting mixture was stirred for 10 minutes at −78° C. and then 30 minutes at −5° C. The reaction mixture was again cooled to −78° C., then a solution of #B1 (1.0 g, 5.1 mmol) in THF (10 mL) was added dropwise to this reaction mixture (maintaining the reaction mixture temperature at −78° C.) and the stirring was continued for 20 minutes. A solution of propylene oxide (0.47 mL, 6.7 mmol) in THF (15 mL) was added dropwise to this reaction mixture at −78° C. and stirring was continued for 30 minutes. The reaction mixture was slowly warmed to room temperature and stirring was continued for 16 h. The mixture was poured onto an ice-cold saturated aqueous NH$_4$Cl solution. The resulting precipitate was dissolved by addition of water, and the mixture was acidified with 1N HCl to pH=3. The aqueous layer was extracted with DCM. The organic layer was washed with brine, dried over anhydrous Na$_2$SO$_4$, concentrated to get residue which was chromatographed on silica gel (230-400 mesh) using diethyl ether as eluent to obtain #B2 as a colorless oil (0.3 g. 25%). R$_f$: 0.3 (Et$_2$O).

LCMS m/z=252.1 (M−1)

Step 3. Synthesis of Boc-protected sulfonamide ketone (#B3). Pyridinium chlorochromate (0.53 g, 2.5 mmol) was added to a solution of #B2 (0.30 g, 1.2 mmol) in DCM (15 mL) and the resulting dark-brown solution was stirred for 4 h at ambient temperature. The reaction mixture was diluted with Et$_2$O (10 mL) and stirring was continued for 15 minutes. It was filtered through silica gel (230-400 mesh) and washed with Et$_2$O and the filtrate was concentrated under reduced pressure to afford #B3 as brown oil (0.2 g, 68%). R$_f$: 0.4 (Et$_2$O).

LCMS m/z=250.1 (M–H). $^1$H NMR (300 MHz, CDCl$_3$): δ 1.51 (s, 9H), 2.23 (s, 3H), 3.02 (t, J=7.2 Hz, 2H), 3.68 (t, J=6.9 Hz, 2H), 7.00 (s, 1H).

Step 4. Synthesis of unsaturated heterocycle (#B4). TFA (4.2 mL, 55.7 mmol) was added to a solution of #B3 (3.5 g, 13.9 mmol) in DCM (50 mL) and the resulting solution was heated to reflux for 48 h. After cooling, EtOH (40 mL) was added to this solution and the solution was concentrated under vacuum to one third of the original volume and subsequent crystallization was done at −20° C. to afford #B4 as an off-white solid (1.1 g, 61%). R$_f$: 0.3 (1:1 EtOAc/DCM).

GCMS m/z=133.0 (M). $^1$H NMR (400 MHz, CDCl$_3$): δ 2.34 (s, 3H), 3.18-3.29 (m, 4H).

Step 5. Synthesis of saturated heterocycle (#B5). NaBH$_4$ (0.46 g, 12.4 mmol) was added in small portions to a solution of #B4 (1.1 g, 8.3 mmol) in dry MeOH (40 mL) at 0° C. and the reaction mixture was stirred at room temperature for 4 h. The reaction mixture was quenched with ice water and extracted with DCM. The organic layers were dried over Na$_2$SO$_4$ and concentrated to provide the pure #B5 as colorless oil (0.85 g, 77%). R$_f$: 0.4 (1:1 EtOAc/DCM).

GCMS m/z=135.1 (M). $^1$H NMR (400 MHz, CDCl$_3$): δ 1.30 (d, J=6 Hz, 3H), 2.00-2.10 (m, 1H), 2.40-2.56 (m, 1H), 3.09-3.17 (m, 1H), 3.20-3.27 (m, 1H), 3.70-3.77 (m, 1H), 4.12 (br s, 1H).

Step 6. Synthesis of coupling product (#B6). Pd$_2$dba$_3$ (0.094 g, 0.10 mmol), BINAP (0.19 g, 0.31 mmol) and Cs$_2$CO$_3$ (3.3 g, 10.3 mmol) were added to a degassed solution of 6-bromoisoquinoline-1-carbonitrile (0.8 g, 3.4 mmol) in toluene (10 mL) followed by the addition of #B5 (0.52 g, 3.8 mmol) under nitrogen atmosphere. The resulting reaction mixture was irradiated in a microwave at 110° C. for 20 minutes. The reaction mixture was cooled to room temperature, diluted with EtOAc, filtered and the filtrate was washed with water. The organic layer was separated and the aqueous layer was extracted with EtOAc. The organic layers were combined, dried over Na$_2$SO$_4$ and evaporated under reduced pressure to afford the crude mixture which was chromatographed on silica gel (100-200 mesh) using 25% EtOAc in petroleum ether to give #B6 as a light brown solid (0.25 g, 25%). R$_f$: 0.4 (25% EtOAc/petroleum ether).

Racemic: LCMS m/z=288.1 (M+H). $^1$H NMR (300 MHz, CDCl$_3$): δ 1.41 (d, J=6.3 Hz, 3H), 2.27-2.38 (m, 1H), 2.71-2.79 (m, 1H), 3.30-3.38 (m, 1H), 3.50-3.58 (m, 1H), 4.38-4.44 (m, 1H), 7.67 (d, J=2.1 Hz, 1H), 7.71 (dd, J=2.1, 9.3 Hz, 1H), 7.83 (d, J=5.7 Hz, 1H), 8.35 (d, J=9 Hz, 1H), 8.61 (d, J=5.7 Hz, 1H).

The racemic compound was chromatographed for enantiomeric separation. Conditions: Column: CHIRAL PAK IA, 4.6×250 mm, 5 μm; Column ID: ANL_CHIR IA_145; Mobile Phase: A=hexane, B=isopropyl alcohol; ISOCRATIC: 60:40; FLOW: 0.8 mL/min; Column Temp: 25° C.; Eluent: EtOH Enantiomer of #8: Chiral HPLC purity: 99.38% (retention time 12.55 minutes)

LCMS m/z=287.9 (M+H). $^1$H NMR (300 MHz, d$_6$-DMSO): δ 1.30 (d, J=6.3 Hz, 3H), 2.10-2.17 (m, 1H), 2.65-2.76 (m, 1H), 3.51-3.55 (m, 1H), 3.70-3.79 (m, 1H), 4.50-4.57 (m, 1H), 7.81 (d, J=2.1 Hz, 1H), 7.87 (dd, J=2.7, 9.0 Hz, 1H), 8.20 (d, J=5.4 Hz, 1H), 8.28 (d, J=9.0 Hz, 1H), 8.64 (d, J=5.7 Hz, 1H).

Example 8

6-[(3S)-3-methyl-1,1-dioxido-1,2-thiazolidin-2-yl]isoquinoline-1-carbonitrile

LCMS m/z=287.9 (M+1). $^1$H NMR (400 MHz, d$_6$-DMSO): δ 1.31 (d, J=5.7 Hz, 3H), 2.08-2.27 (m, 1H), 2.67-2.74 (m, 1H), 3.49-3.59 (m, 1H), 3.71-3.79 (m, 1H), 4.50-4.57 (m, 1H), 7.81 (s, 1H), 7.87 (d, J=9.3 Hz, 1H), 8.21 (d, J=5.4 Hz, 1H), 8.29 (d, J=9.0 Hz, 1H), 8.64 (d, J=5.7 Hz, 1H). Chiral HPLC purity: 98.9% (retention time 20.42 minutes)

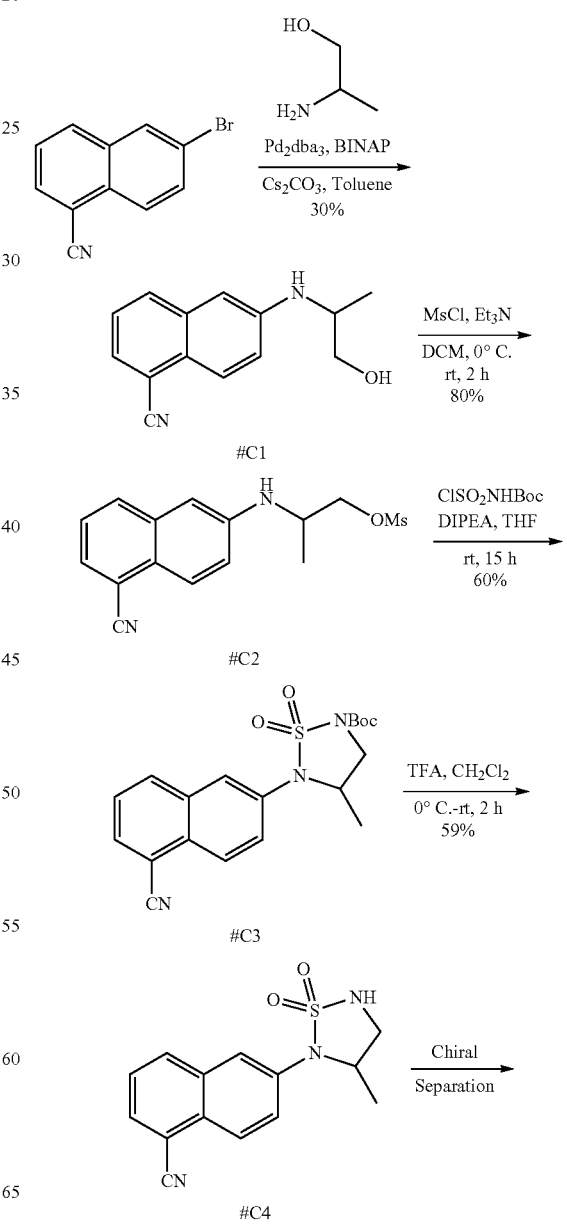

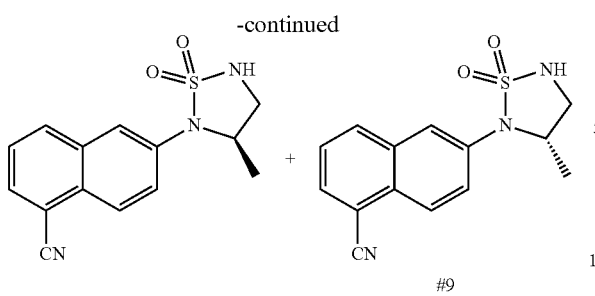

Step 1. Synthesis of coupling product (#C1). A solution of #A3 (1.0 g, 4.3 mmol) in toluene (100 mL) was bubbled with argon gas for 15 minutes. Pd$_2$dba$_3$ (0.12 g, 0.13 mmol), BINAP (0.24 g, 0.39 mmol) and Cs$_2$CO$_3$ (4.7 g, 14.6 mmol) were added to the solution followed by the addition of racemic 2-aminopropan-1-ol (0.66 mL, 8.6 mmol). The mixture was heated at 100° C. under argon atmosphere for 3 h. The reaction mixture cooled to room temperature, diluted with EtOAc and washed with water. The organic layer was washed with brine, dried over Na$_2$SO$_4$ and concentrated under reduced pressure. The crude compound was purified by silica gel column chromatography using 25% EtOAc in petroleum ether as an eluent to yield product #C1 as yellow solid (0.3 g, 30%). R$_f$: 0.3 (40% EtOAc in petroleum ether). LCMS m/z=227.0 (M+H).

Step 2. Synthesis of mesylate product (#C2). Mesyl chloride (0.80 mL, 10.6 mmol) was added to a solution of #C1 (0.60 g, 2.7 mmol) and Et$_3$N (1.4 mL, 10.6 mmol) in DCM (40 mL) at 0° C., and the mixture was stirred at room temperature for 2 h. The reaction mixture diluted with DCM and, washed with water. The organic layer was washed with brine, dried over Na$_2$SO$_4$ and concentrated under reduce pressure. The crude product #C2 (0.65 g of oily solid) was used for the next step without purification. R$_f$: 0.4 (40% EtOAc in petroleum ether). LCMS m/z=305.0 (M+H).

Step 3. Synthesis of cyclized Boc-protected product (#C3). ClSO$_2$NCO (1 mL, 10.6 mmol) was added dropwise over 5 minutes to a mixture of t-butanol (1 mL) and toluene (2.5 mL), and the reaction mixture was stirred at room temperature for 45 minutes. The mixture (t-butyl chlorosulfonylcarbamate) was added to a solution of #C2 (0.65 g, 2.1 mmol) and DIPEA (1.8 mL, 10.6 mmol) in THF (10 mL), and the mixture was stirred at room temperature for 15 h. The reaction mixture was diluted with DCM and extracted with water. The organic layer dried over Na$_2$SO$_4$ and concentrated in vacuo. Product was purified by passing through silica gel column (100-200 mesh) using 25% EtOAc in petroleum ether to yield 0.5 g (60%) of #C3 as off-white solid. R$_f$: 0.5 (50% EtOAc in petroleum ether).

$^1$H NMR (400 MHz, d$_6$-DMSO): δ 1.29 (d, J=6.2 Hz, 3H), 1.59 (s, 9H), 3.62 (m, 1H), 4.19 (m, 1H), 4.26 (m, 1H), 7.75 (t, J=7.8 Hz, 1H), 7.83 (m, 1H), 8.17 (d, J=6.6 Hz, 1H), 8.21 (d, J=6.6 Hz, 1H), 8.24 (d, J=8.4 Hz, 1H), 8.40 (d, J=8.9 Hz, 1H).

Step 4. Synthesis of racemic mixture (#C4) and final product #9. TFA (10 mL) was added to a solution of #C3 (0.50 g, 0.82 mmol) in DCM (10 mL) at 0° C., and the mixture was stirred at room temperature for 2 h. The reaction mixture was concentrated, diluted with water, neutralized with NaHCO$_3$, extracted with DCM and washed with water. The organic layer was dried over Na$_2$SO$_4$ and concentrated. Crude compound was purified by treating with DCM and n-pentane to yield 0.22 g (59%) of #C4 as white solid. R$_f$: 0.3 (60% EtOAc in petroleum ether). #C4 (racemic, 220 mg) was subjected to chiral preparative HPLC to obtain two enantiomers as off-white solids (65 mg of #9 and 35 mg of the other enantiomer). Chiral preparative HPLC conditions:

Column: CHIRALPAK IC, 250×30 mm, 5 μm; Mobile phase: n-Hexane/EtOH (60%/40%); Flow rate: 30 mL/min.

Enantiomer of #9: Chiral HPLC purity: 98.60% (retention time 10.93 minutes)

Example 9

6-[(3S)-3-methyl-1,1-dioxido-1,2,5-thiadiazolidin-2-yl]naphthalene-1-carbonitrile (Stereochemistry is Arbitrarily Assigned)

LCMS m/z=286.0 (M−H). $^1$H NMR (400 MHz, d$_6$-DMSO): δ 1.31 (d, J=6.2 Hz, 3H), 3.13-3.25 (m, 1H), 3.71 (dt, J=12.5, 6.8 Hz, 1H), 4.49-4.62 (m, 1H), 7.62-7.70 (m, 1H), 7.75-7.83 (m, 2H), 7.99 (t, J=7.8 Hz, 1H), 8.07 (d, J=6.6 Hz, 1H), 8.14 (d, J=8.9 Hz, 1H), 8.28 (d, J=8.4 Hz, 1H). Chiral HPLC purity: 99.1% (retention time 17.12 minutes)

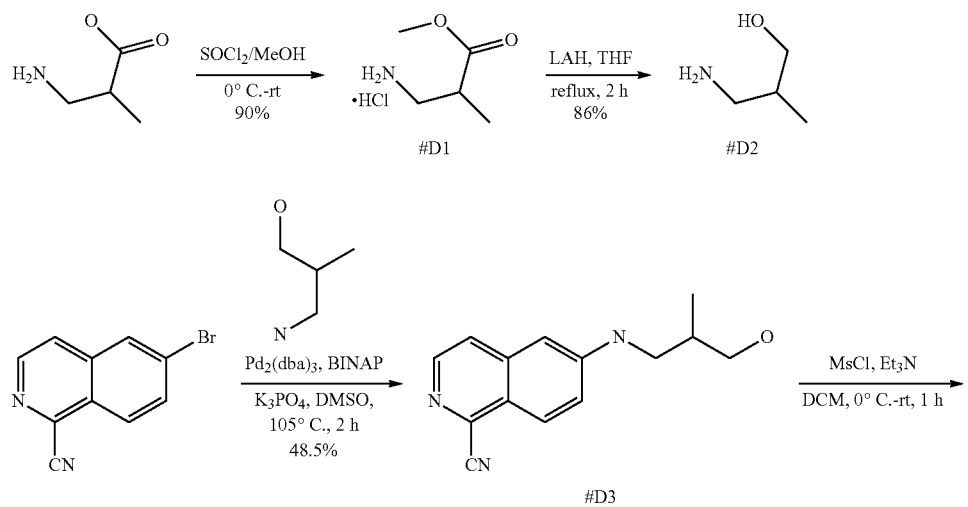

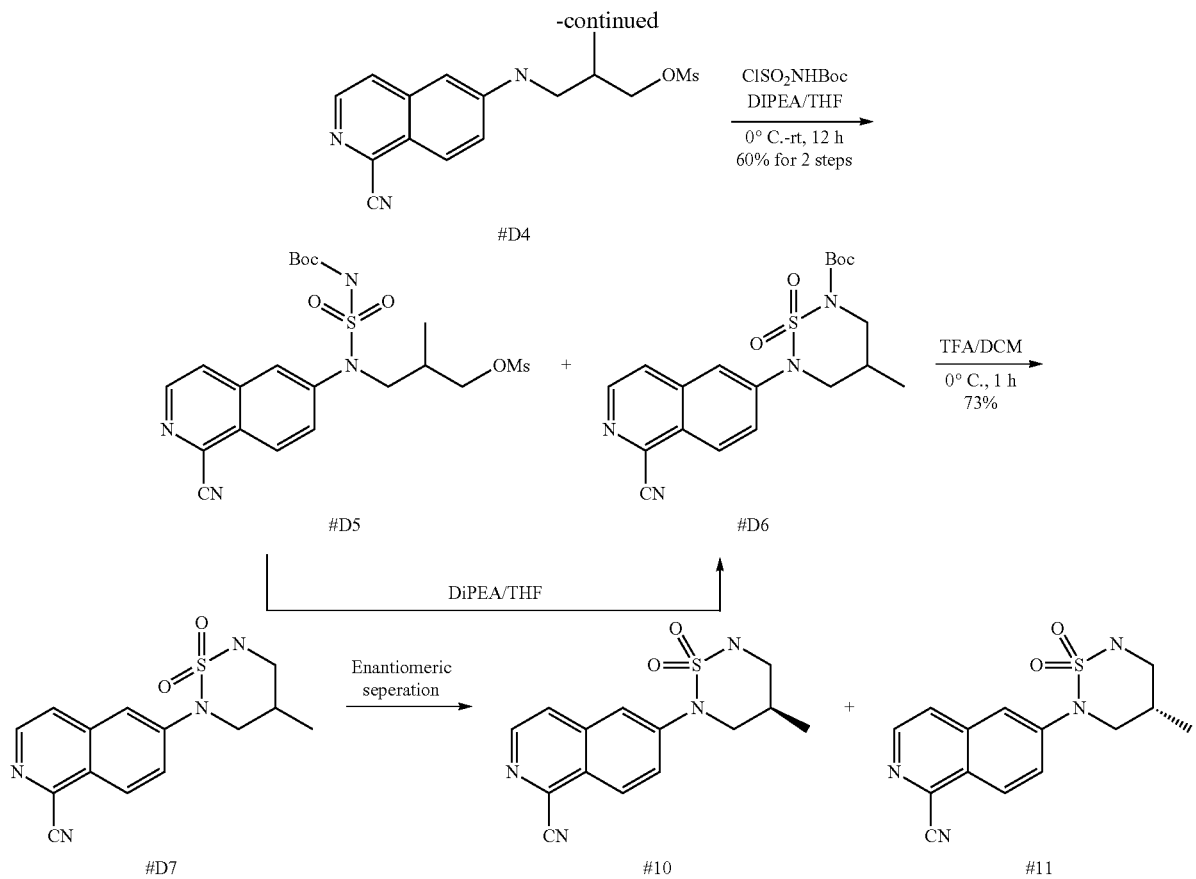

Step 1. Synthesis of aminoester (#D1). Thionylchlride (8.5 mL, 116.5 mmol) was added to the solution of amino acid (4.0 g, 38.8 mmol) in MeOH (170 mL) at 0° C., and the reaction mixture was stirred for 6 h at room temperature. The reaction was monitored by TLC, and after disappearance of the starting material it was cooled to room temperature and solid NaHCO$_3$ was added. The reaction mixture was filtered, concentrated in vacuo and the resulting residue was triturated with diethyl ether to obtain crude #D1 (4 g, 90%) as a white solid. R$_f$: 0.4 (t-BuOH:AcOH:H$_2$O (4:0.5:0.5)).

GCMS m/z=117.1 (M). $^1$H NMR (400 MHz, d$_6$-DMSO): δ 1.17 (d, J=6.8 Hz, 3H), 2.83-2.88 (m, 2H), 3.03-3.05 (m, 1H), 3.65 (s, 3H), 8.02-8.30 (br s, 3H).

Step 2. Synthesis of aminoalcohol (#D2). #D1 (2.0 g, 13.0 mmol) was added portionwise to a suspension of LiAlH$_4$ (1.4 g, 39.2 mmol) in THF (75 mL) under nitrogen atmosphere at 0° C. The reaction mixture was stirred for 30 minutes and then allowed to stir at room temperature for another 30 minutes. The reaction mixture was refluxed for 2 h, and then it was cooled to −10° C. and quenched carefully with ice cold water (1.4 mL). 10% NaOH solution (2.8 mL) and ice cold water (4.2 mL) were added, and the mixture was stirred for 15 minutes. It was filtered, and the filtrate washed with EtOAc (3×100 mL), dried over anhydrous Na$_2$SO$_4$ and concentrated under vacuum to obtain #D2 (1.2 g, 86%) as a pale yellow liquid. R$_f$: 0.2 (20% MeOH in DCM).

$^1$H NMR (400 MHz, d$_6$-DMSO): δ 0.78 (d, J=6.8 Hz, 3H), 1.46-1.54 (m, 1H), 2.41-2.45 (m, 2H), 2.50-2.54 (m, 1H), 3.22-3.34 (m, 4H).

Step 3. Synthesis of coupling product (#D3). K$_3$PO$_4$ (6.1 g, 28.8 mmol), BINAP (0.44 g, 0.72 mmol) and Pd$_2$(dba)$_3$ (0.32 g, 0.36 mmol) was added to the degassed suspension of 6-bromo-1-cyanoisoquinoline #A3 (1.7 g, 7.2 mmol), #D2 (1.2 g, 14.5 mmol) in DMSO at room temperature. The reaction mixture was heated at 105° C. for 2 h. The reaction was cooled to room temperature, water (500 mL) followed by EtOAc (100 mL) were added, and the mixture was stirred for 10 minutes. The biphasic mixture was filtered through a Celite™ pad and washed with EtOAc (100 mL). The organic layer was separated, and the aqueous layer was extracted with EtOAc (3×100 mL). The combined organic layers were dried over anhydrous Na$_2$SO$_4$, concentrated under reduced pressure to get a crude material. This was purified by column chromatography on 100-200 mesh silica gel, using 50-70% EtOAc in petroleum ether as the eluent to obtain #D3 (0.5 g, 48.5%) as a yellow solid. R$_f$: 0.4 (60% EtOAC in petroleum ether).

LCMS m/z=242.0 (M+H). $^1$H NMR (400 MHz, d$_6$-DMSO): δ 0.97 (d, J=6.4 Hz, 3H), 1.87-1.99 (m, 1H), 2.92-2.99 (m, 1H), 3.20-3.27 (m, 1H), 3.38-3.42 (m, 2H), 4.59 (t, J=5.2 Hz, 1H), 6.77 (d, J=2.0, 1 H), 7.01 (t, J=5.6 Hz, 1H), 7.34 (dd, J=9.2 Hz, J=2.0 Hz, 1H), 7.73 (d, J=6.0 Hz, 1H), 7.88 (d, J=8.8 Hz, 1H), 8.312 (d, J=6.0 Hz, 1H).

Step 4. Methanesulfonated coupling product (#D4). Triethylamine (0.44 mL, 3.1 mmol) was added to a solution of #D3 (0.50 g, 2.0 mmol) in DCM at 0° C. Methanesulfonylchloride (0.25 mL, 3.1 mmol) was added over 10 minutes, and the reaction mixture was stirred for 1 h at room temperature. After disappearance of the starting material by TLC, it was diluted with DCM and washed with water. The organic layer was separated, dried over Na$_2$SO$_4$, concentrated under reduced pressure to obtain crude #D4 (0.6 g, crude) as yellow solid. This was used for next step without any purification. $R_f$: 0.6 (50% EtOAc in petroleum ether).

LCMS m/z=320.0 (M+H). $^1$H NMR (400 MHz, CDCl$_3$): δ 1.17 (d, J=6.8 Hz, 3H), 2.32-2.37 (m, 1H), 3.06 (s, 3H), 3.26-3.41 (m, 2H), 4.16-4.20 (m, 1H), 4.33-4.37 (m, 1H), 4.75 (br s, 1H), 6.70 (d, J=2.4, 1H), 7.09 (dd, J=9.2 Hz, 2.4 Hz, 1H), 7.57 (d, J=6.0 Hz, 1H), 8.05 (d, J=9.2 Hz, 1H), 8.39 (d, J=5.6 Hz, 1H).

Step 5. Cyclized and uncyclized intermediates (#D5, #D6). Chlorosulfonylisocyanate (1.2 mL, 13.1 mmol) was added dropwise to a solution t-BuOH (1.4 mL, 13.1 mmol) in toluene (4.0 mL) at −5° C. The reaction mixture was stirred at room temperature for 20 minutes, and then THF (1 mL) was added to the resulting suspension to obtain clear solution. In another flask, DIPEA (2.3 mL, 13.1 mmol) was added to a solution of #D4 (0.6 g, crude 2.6 mmol) in dry THF (3 mL). The above prepared reagent (ClSO$_2$NH-Boc) was added to this reaction mixture dropwise at room temperature over a period of 20 minutes. The resulting reaction mixture was then stirred for 16 h at room temperature. The mixture was diluted with EtOAc (100 mL) and washed with water (100 mL). The aqueous layer was washed with EtOAc (2×100 mL), combined all the organic layers, dried over Na$_2$SO$_4$, concentrated under reduced pressure to obtain the crude product (LCMS shows desired #D6 and uncyclized #D5. This crude was purified by column chromatography on 100-200 mesh silica gel, using 10-30% EtOAc in petroleum ether as an eluent to obtain desired #D6 (0.35 g, 47.8%), and uncyclized #D5 (0.22 g, crude).

The uncyclized #D5 (0.22 g, crude) was dissolved in THF (1 mL) and DIPEA (0.6 mL) was added to the solution. The reaction mixture was stirred for another 12 h at room temperature. After which time, it was diluted with EtOAc (100 mL) and washed with water (100 mL). The aqueous layer was washed with EtOAc (2×100 mL), combined all the organic layers, dried over Na$_2$SO$_4$, concentrated under reduced pressure to obtain crude product. This crude was purified by column chromatography on 100-200 mesh silica gel, using 10-30% EtOAc in petroleum ether as an eluent to obtain desired #D6 (1.1 g, 13.2%). Total amount of #D6 was (0.5 g, 60% for two steps, 82% LCMS purity). $R_f$: 0.8 (60% EtOAc in petroleum ether).

LCMS m/z=403.1 (M+H). $^1$H NMR (400 MHz, CDCl3): δ 1.04 (d, J=6.8 Hz, 3H), 1.50 (s, 9H), 2.38-2.48 (m, 1H), 3.65-3.82 (m, 2H), 3.92-4.02 (m, 1H), 4.30-4.38 (m, 1H), 7.79-7.81 (m, 1H), 7.86-7.88 (m, 2H), 8.34-8.37 (d, J=9.2 Hz, 1H), 8.67 (d, J=6.0 Hz, 1H).

Step 6. Racemate #D7 and final products (#10, #11). TFA (5 mL) was added to a solution of #D6 (0.15 g, 0.37 mmol) in DCM (100 mL) at 0° C. The reaction mixture was stirred for 1 h at 0° C. The solution was neutralized with saturated aqueous NaHCO$_3$ solution at 0° C. The mixture was diluted with water, extracted with DCM (3×100 mL). The combined organic layers were dried over anhydrous Na$_2$SO$_4$ and concentrated under reduced pressure to obtain racemic #D7 (0.10 mg, 73%).

LCMS m/z=303.0 (M+H). $R_f$: 0.3 (60% EtOAc in petroleum ether).

Enantiomeric separation: #D7 was submitted for chiral separation to obtain final compounds #10 (0.015 mg) and #11 (0.016 mg).

Column: CHIRALPAK IA, 4.6×250 mm, 5 µm; Mobile phase: n-Hexane/i-PrOH/DCM (60%/15%/15%); Flow rate: 0.8 mL/min.

Example 10

6-[(4R)-4-methyl-1,1-dioxido-1,2,6-thiadiazinan-2-yl]isoquinoline-1-carbonitrile (#10; R=(R)—CH$_3$)

LCMS m/z=303.0 (M+1). $^1$H NMR (400 MHz, d$_6$-DMSO): δ 0.98 (d, J=6.4 Hz, 3H), 2.22-2.26 (m, 1H), 3.16-3.22 (m, 1H), 3.34-3.39 (m, 1H), 3.59-3.65 (m, 1H), 3.77-3.81 (m, 1H), 7.75-7.79 (m, 1H, disappeared in D20 exchange), 7.95 (dd, J=8.8 Hz, J=2.0 Hz, 1H), 8.06 (d, J=1.6 Hz, 1H), 8.23-8.27 (m, 2H), 8.703 (d, J=5.2 Hz, 1H). $R_f$: 0.3 (60% EtOAc in petroleum ether). Chiral HPLC purity: 98.2% (retention time 11.43 minutes).

Example 11

6-[(4S)-4-methyl-1,1-dioxido-1,2,6-thiadiazinan-2-yl]isoquinoline-1-carbonitrile (#11; R=(S)—CH$_3$)

LCMS m/z=301.0 (M−1). $^1$H NMR (400 MHz, d$_6$-DMSO): δ 0.98 (d, J=7.2 Hz, 3H), 2.22-2.27 (m, 1H), 3.13-3.22 (m, 1H), 3.32-3.39 (m, 1H), 3.59-3.65 (m, 1H), 3.77-3.81 (m, 1H), 7.76-7.79 (m, 1H, disappeared in D$_2$O exchange), 7.96 (dd, J=9.2 Hz, J=2.0 Hz, 1H), 8.06 (d, J=2.0 Hz, 1H), 8.23-8.27 (m, 2H), 8.70 (d, J=5.2 Hz, 1H). $R_f$: 0.3 (60% EtOAc in petroleum ether). Chiral HPLC purity: 97.5% (retention time 12.81 minutes).

Targets #12, #13, #14, #15, #17, #18, #19, #20, #21, #22 of the General Formula Below Were Prepared According to a Similar Procedure Outlined Above for Targets #10, #11.

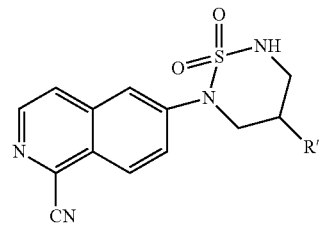

Example 12

6-{(3R)-1,1-dioxido-3-(3-phenyl)-1,2,5-thiadiazolidin-2-yl}isoquinoline-1-carbonitrile (Stereochemistry Arbitrarily Assigned) (#12; R=C$_6$H$_5$)

LCMS m/z=365.1 (M+1). $^1$H NMR (400 MHz, d$_6$-DMSO): δ 3.39-3.57 (m, 2H), 3.67-3.81 (m, 1H), 3.87 (d, J=11.2 Hz, 1H), 4.14 (t, J=11.9 Hz, 1H), 7.26-7.48 (m, 5H), 8.02 (d, J=9.37 Hz, 2H), 8.13 (br. s., 1H), 8.25 (d, J=7.0 Hz, 2H) 8.69 (d, J=5.4 Hz, 1H).

Example 13

6-(4,4-dimethyl-1,1-dioxido-1,2,6-thiadiazinan-2-yl)isoquinoline-1-carbonitrile (#13; R'=(gem-(CH$_3$)$_2$)

LCMS m/z=317.0 (M+1). $^1$H NMR (400 MHz, d$_6$-DMSO): δ 1.10 (s, 6H), 3.16 (d, J=7.3 Hz, 2H), 3.55 (s,

2H), 7.92 (dd, J=9.1, 2.1 Hz, 1H), 7.97-8.04 (m, 2H), 8.21-8.28 (m, 2H), 8.69 (d, J=5.6 Hz, 1H).

Example 14

6-(6,6-dioxido-6-thia-5,7-diazaspiro[2.5]oct-5-yl)isoquinoline-1-carbonitrile (#14; R'=cyclopropyl)

LCMS m/z=315.2 (M+1). $^1$H NMR (400 MHz, d$_6$-DMSO): δ 0.66 (d, J=6.2 Hz, 4H), 3.24 (d, J=7.1 Hz, 2H), 3.64 (s, 2H), 7.89-8.00 (m, 2H), 8.03 (d, J=2.1 Hz, 1H), 8.21-8.27 (m, 2H), 8.69 (d, J=5.6 Hz, 1H).

Example 15

6-[(4R)-4-(3-methylbenzyl)-1,1-dioxido-1,2,6-thiadiazinan-2-yl]isoquinoline-1-carbonitrile (Stereochemistry Arbitrarily Assigned) (#15; R'=CH$_2$-[m-CH$_3$—C$_6$H$_4$])

LCMS m/z=393.0 (M+1). $^1$H NMR (400 MHz, d$_6$-DMSO): δ 2.26 (s, 3H), 2.58-2.69 (m, 1H), 2.69-2.78 (m, 1H), 3.63-3.81 (m, 2H), 6.98-7.11 (m, 3H), 7.18 (t, J=7.5 Hz, 1H), 7.69-7.78 (m, 1H), 7.93 (dd, J=9.1, 2.0 Hz, 1H), 8.03 (d, J=2.1 Hz, 1H), 8.21-8.28 (m, 2H), 8.70 (d, J=5.6 Hz, 1H) (Additional protons under water peak and cannot be integrated).

Targets #16 was Prepared According to a Similar Procedure Outlined Above for Target #5.

Example 16

6-[(4R)-6-ethyl-4-methyl-1,1-dioxido-1,2,6-thiadiazinan-2-yl]isoquinoline-1-carbonitrile (Stereochemistry Arbitrarily Assigned) (#16; R'=CH$_3$, N—C$_2$H$_5$)

LCMS m/z=303.0 (M+1). $^1$H NMR (400 MHz, d$_6$-DMSO): δ 0.95 (d, J=6.3 Hz, 3H), 1.15 (t, 3H), one proton under DMSO peak, 3.09-3.14 (m, 1H), 3.20-3.26 (m, 3H), 3.64-3.69 (m, 2H), 7.96 (dd, J=8.8 Hz, J=2.1 Hz, 1H), 8.05 (m, 1H), 8.21-8.25 (m, 2H), 8.703 (m, 1H).

Example 17

6-(5-methyl-1,1-dioxido-1,2,6-thiadiazinan-2-yl)isoquinoline-1-carbonitrile (Racemic Mixture)

LCMS m/z=303.1 (M+1). $^1$H NMR (400 MHz, CDCl3): δ 1.39 (d, J=6.3 Hz, 3H), 1.79-1.94 (m, 1H), 2.05 (dd, J=14.1, 2.5 Hz, 1H), 3.66-3.77 (m, 1H), 4.03-4.18 (m, 2H), 7.78-7.91 (m, 3H), 8.34 (d, J=9.0 Hz, 1H), 8.66 (d, J=5.7 Hz, 1H) (NH proton exchanged).

Example 18

6-[(4S)-4-(4-methylphenyl)-1,1-dioxido-1,2,6-thiadiazinan-2-yl]isoquinoline-1-carbonitrile (Stereochemistry Arbitrarily Assigned) (#18; R'=(S)-p-CH$_3$—C$_6$H$_4$)

LCMS m/z=379.1 (M+1). $^1$H NMR (400 MHz, d$_6$-DMSO): δ 2.29 (s, 3H), 3.36-3.52 (m, 2H), 3.71 (d, J=12.0 Hz, 1H), 3.83 (d, J=11.0 Hz, 1H), 4.05-4.16 (m, 1H), 7.19 (m, J=7.9 Hz, 2H), 7.30 (m, J=7.9 Hz, 2H), 7.95-8.05 (m, 2H), 8.09-8.14 (m, 1H), 8.21-8.28 (m, 2H), 8.69 (d, J=5.6 Hz, 1H).

Example 19

6-[(4R)-4-(4-methylphenyl)-1,1-dioxido-1,2,6-thiadiazinan-2-yl]isoquinoline-1-carbonitrile (Stereochemistry Arbitrarily Assigned) (#19; R'=(R)-p-CH$_3$—C$_6$H$_4$])

LCMS m/z=379.1 (M+1). $^1$H NMR (400 MHz, d$_6$-DMSO): δ 2.29 (s, 3H), 3.36-3.53 (m, 2H), 3.63-3.77 (m, 1H), 3.83 (d, J=11.0 Hz, 1H), 4.03-4.16 (m, 1H), 7.19 (m, J=7.9 Hz, 2H), 7.30 (m, J=8.0 Hz, 2H), 7.94-8.05 (m, 2H), 8.12 (d, J=1.9 Hz, 1H), 8.21-8.30 (m, 2H), 8.69 (d, J=5.5 Hz, 1H).

Example 20

6-[(4S)-4-(3-methylphenyl)-1,1-dioxido-1,2,6-thiadiazinan-2-yl]isoquinoline-1-carbonitrile (Stereochemistry Arbitrarily Assigned) (#20; R'=(S)—C$_2$H$_5$)

LCMS m/z=317.1 (M+1). $^1$H NMR (400 MHz, d$_6$-DMSO): δ 0.94 (t, J=7.5 Hz, 3H), 1.31-1.44 (m, 2H), 1.91-2.07 (m, 1H), 3.19 (dd, J=14.0, 10.4 Hz, 1H), 3.37-3.48 (m, 1H), 3.63 (dd, J=12.4, 10.3 Hz, 1H), 3.74-3.84 (m, 1H), 7.73 (s, 1H), 7.95 (dd, J=9.1, 2.2 Hz, 1H), 8.06 (d, J=2.1 Hz, 1H), 8.20-8.30 (m, 2H), 8.70 (d, J=5.6 Hz, 1H).

Example 21

6-[(4S)-4-ethyl-1,1-dioxido-1,2,6-thiadiazinan-2-yl]isoquinoline-1-carbonitrile (Stereochemistry Arbitrarily Assigned) (#21; R'=(S)-m-CH$_3$—C$_6$H$_4$)

LCMS m/z=379.1 (M+1). $^1$H NMR (400 MHz, d$_6$-DMSO): δ 2.32 (s, 3H), 3.35-3.54 (m, 2H), 3.66-3.79 (m, 1H), 3.84 (d, J=10.7 Hz, 1H), 4.06-4.19 (m, 1H), 7.12 (d, J=7.3 Hz, 1H), 7.17-7.22 (m, 1H), 7.22-7.31 (m, 2H), 7.96-8.05 (m, 2H), 8.12 (d, J=2.1 Hz, 1H), 8.21-8.28 (m, 2H), 8.69 (d, J=5.7 Hz, 1H).

Example 22

6-(1,1-dioxido-4-propyl-1,2,6-thiadiazinan-2-yl)isoquinoline-1-carbonitrile (Racemic Mixture) (#22; R'=C$_3$H$_7$)

LCMS m/z=331.2 (M+1). $^1$H NMR (400 MHz, d$_6$-DMSO): δ 0.81-0.96 (m, 3H), 1.33 (br. s., 4H), 2.09 (br. s., 1H), 3.12-3.25 (m, 1H), 3.41 (d, J=13.5 Hz, 1H), 3.56-3.68 (m, 1H), 3.77 (d, J=10.4 Hz, 1H), 7.73 (dd, J=9.0, 4.6 Hz, 1H), 7.95 (d, J=9.1 Hz, 1H), 8.06 (s, 1H), 8.20-8.30 (m, 2H), 8.70 (d, J=5.6 Hz, 1H).

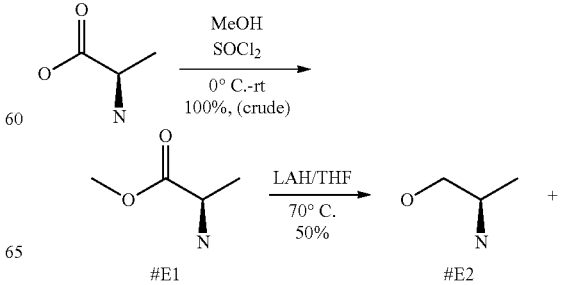

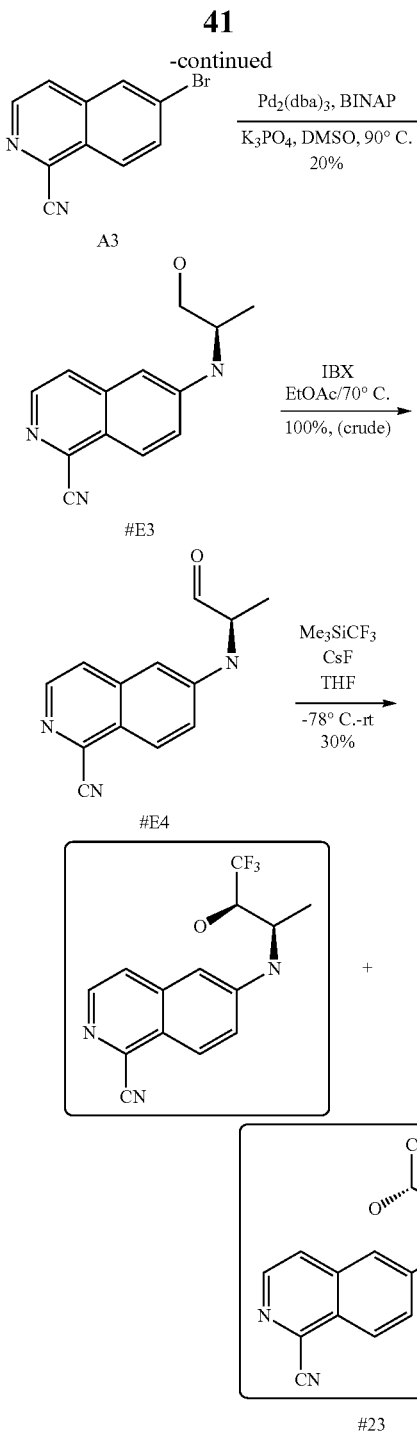

¹H NMR (400 MHz, d₆-DMSO): δ 1.36 (d, J=7.2 Hz, 3H), 3.11 (s, 1H), 3.68 (s, 3H), 3.90 (q, J=7.2 Hz, 1H), 6.50 (br s, 3H).

Step 2. Synthesis of aminoalcohol (#E2). A solution of #E1 (19.0 g, 184.5 mmol) in THF (300 mL) was cooled to 0° C., and LiAlH₄ (21.0 g, 553.4 mmol) was added portionwise over 30 minutes. The reaction mixture was stirred at room temperature till the reaction mixture become slurry, and then refluxed for 2 h. The reaction mixture was cooled to room temperature, quenched with 2N NaOH solution to pH 7. The solids were filtered through a Celite™ pad and washed with THF (100 mL×3). The filtrate was concentrated under reduced pressure to give crude material. The product was purified by neutral alumina column chromatography with 100% MeOH as an eluting system to give #E2 as a brown liquid (6.0 g, 43%). $R_f$: 0.1 (20% MeOH in DCM).

¹H NMR (400 MHz, d₆-DMSO): δ 0.89 (d, J=6.4 Hz, 3H), 2.71-2.78 (m, 1H), 3.06-3.10 (m, 1H), 3.17-3.23 (m, 1H).

Step 3. Synthesis of 6-amino isoquinoline (#E3). A solution of #A2 (4.0 g, 51.7 mmol), 6-bromoisoquinoline-1-carbonitrile #A3 (6.0 g, 25.9 mmol), BINAP (3.2 g, 5.2 mmol), Pd₂(dba)₃ (2.3 g, 2.6 mmol) and potassium phosphate (11.0 g, 51.7 mmol) in anhydrous DMSO (35 mL) was heated at 80° C. for 2 h. The complete disappearance of the 6-bromoisoquinoline-1-carbonitrile #A3 was observed on TLC. The reaction mixture was cooled to room temperature, filtered through Celite™ pad and the filtrate was diluted with water (100 mL). The mixture was extracted with EtOAc (100 mL×3). The combined organic layers were dried over anhydrous sodium sulfate and concentrated under reduced pressure to give crude material which was purified by silica gel (100-200 mesh) column chromatography using 40% EtOAc in petroleum ether as an eluting system to give #E3 as yellow solid (1.5 g, 25.4%). $R_f$: 0.4 (60% EtOAc in petroleum ether).

LCMS m/z=227.9 (M+H); ¹H NMR (400 MHz, d₆-DMSO): δ 1.18 (d, J=6.8 Hz, 3H), 3.36-3.47 (m, 1H), 3.48-3.53 (m, 1H), 3.60-3.66 (m, 1H), 6.80-6.82 (m, 2H), 7.32 (dd, J=2.4 Hz, 8.8 Hz, 1H), 7.72 (d, J=5.6 Hz, 1H), 7.87 (d, J=9.6 Hz, 1H), 8.30 (d, J=5.6 Hz, 1H).

Step 4. Synthesis of aldehyde product (#E4). A solution of #E3 (0.70 g, 3.1 mmol) in EtOAc (15 mL) was cooled to 0° C., and IBX (1.7 g, 6.2 mmol) was added portionwise. The reaction mixture was stirred at 80° C. for 2 h and was cooled to room temperature. Then the reaction mixture was filtered through Celite™ pad and rinsed with EtOAc. The filtrate was washed with aqueous saturated NaHCO₃ solution (50 mL). The organic layer was collected, washed with water, brine, dried over anhydrous sodium sulfate and concentrated under reduced pressure to give #E4 (0.7 g, crude). This was used as such in next step without any further purification. $R_f$: 0.7 (60% EtOAc in petroleum ether).

LCMS m/z=225.9 (M+H).

Step 5. Synthesis of product (#23). A solution of #E4 (0.70 g crude, 3.1 mmol), cesium fluoride (2.3 g, 15.5 mmol), in THF (15 mL) was cooled at −78° C., and Me₃SiCF₃ (0.7 mL, 4.7 mmol) was added dropwise over 10 minutes. After stirring 1 h, the reaction mixture was stirred at room temperature for 16 h. Water (50 mL) was added, and the reaction mixture was extracted with EtOAc (50 mL×3). The combined organic layers were dried over anhydrous sodium sulfate and concentrated under reduced pressure to give crude material. The stereoisomers were separated by chromatography on silica gel (230-400 mesh) using 30% EtOAc in petroleum ether as the eluent to provide compound #23 (55 mg, 6%) and its stereoisomer (130 mg, 14%). Total yield (185 mg, 20%). $R_f$:

Step 1. Synthesis of methyl alanine (#E1). Thionyl chloride (18.4 mL, 252.8 mmol) was added to a solution of alanine (15.0 g, 168.5 mmol) in methanol at 0° C. Then, the reaction mixture was stirred at room temperature for 3 h. After the depletion of the starting material, the reaction was cooled to 0° C. and treated with solid NaHCO₃. The slurry was filtered through Celite™ pad, and rinsed with MeOH (100 mL). The filtrate was concentrated under reduced pressure to provide a residue that was diluted with DCM, washed with water, brine, dried and concentrated to give #E1 (19.0 g, crude). This was used for the next step without further purification. $R_f$: 0.6 (20% methanol in DCM).

Example 23

6-{[(2R,3S)-4,4-trifluoro-3-hydroxybutan-2-yl]amino}isoquinoline-1-carbonitrile (#23)

LCMS m/z=296.3 (M+1). $^1$H NMR (400 MHz, d$_6$-DMSO): δ 1.27 (d, J=8.0 Hz, 3H), 4.01-4.04 (m, 1H), 4.11-4.15 (m, 1H), 6.69 (d, J=6.8 Hz, 1H), 6.76 (d, J=9.2 Hz, 1H), 6.89 (d, J=2.0 Hz, 1H), 7.44 (dd, J=2.0 Hz, 1H), 7.74 (d, J=5.6 Hz, 1H), 7.88 (d, J=9.6 Hz, 1H), 8.33 (d, J=6.0 Hz, 1H).

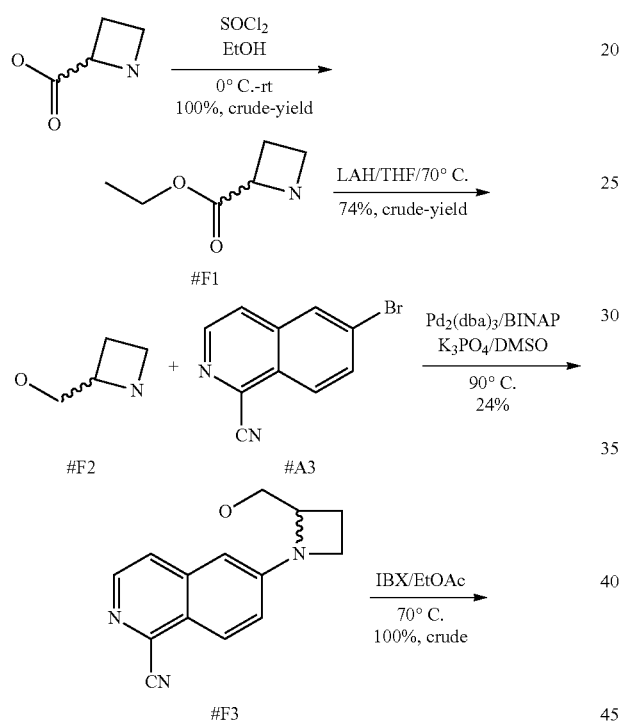

Step 1. Synthesis of azetidine-2-carboxylic acid ethyl ester (#F1). Thionyl chloride (5.5 mL, 74.3 mmol) was added to a solution of azetidine-2-carboxylic acid (5.0 g, 49.5 mmol) in ethanol at 0° C. The reaction mixture was stirred at room temperature for 2 h. After the depletion of the starting material, the reaction was cooled to 0° C. and treated with solid NaHCO$_3$. The slurry was filtered through a Celite™ pad and washed with (100 mL) of ethanol. The filtrate was stripped under reduced pressure to give a residue then dissolved in DCM and washed with water, brine, dried and concentrated to give #F1 (6.3 g, 100% crude). The residue was used for the next step without any further purification. R$_f$: 0.6 (10% MeOH in DCM).

GCMS m/z=129.2; $^1$H NMR (300 MHz, D$_2$O): δ 1.33 (t, J=6.9 Hz, 3H), 2.70-2.92 (m, 2H), 3.95-4.08 (m, 1H), 4.16-4.25 (m, 1H), 4.37 (q, J=6.9 Hz, 2H), 5.21 (t, J=9.9 Hz, 1H).

Step 2. Synthesis of azetidin-2-ylmethanol (#F2). A solution of #F1 (9.0 g, 70.0 mmol) in THF (300 mL) was cooled to 0° C. LiAlH$_4$ (8.0 g, 210.0 mmol) was added portionwise over 30 minutes. Then the reaction mixture was stirred at room temperature for 30 minutes followed by reflux for 2 h. The reaction mixture was cooled to room temperature, and saturated aqueous NH$_4$Cl solution (80 mL) was added dropwise at 0° C. The reaction mixture was filtered through Celite™ pad and washed with EtOAc (100 mL×3). The filtrate was concentrated under reduced pressure to give crude #F2 which was purified by silica gel (100-200 mesh) column chromatography using 10% MeOH in DCM as eluant to give #F2 as brown liquid (4.5 g, 74%). R$_f$: 0.2 (20% MeOH in DCM).

GCMS m/z=87.0 (M+H)

Step 3. Synthesis of 6-amino isoquinoline (#F3). A solution of #F2 (4.5 g, 51.7 mmol), 6-bromoisoquinoline-1-carbonitrile (6.0 g, 25.9 mmol), BINAP (3.2 g, 5.1 mmol), Pd$_2$(dba)$_3$ (2.3 g, 2.6 mmol) and potassium phosphate (11.0 g, 51.7 mmol) in anhydrous DMSO (35 mL) was heated at 80° C. for 2 h. The complete disappearance of the 6-bromoisoquinoline-1-carbonitrile was observed on TLC. The reaction mixture was cooled to room temperature, filtered through a Celite™ pad and the filtrate was diluted with water (100 mL). The mixture was extracted with EtOAc (100 mL×3). The combined organic layers were dried over anhydrous sodium sulfate and concentrated under reduced pressure to give crude material. The product was purified by chromatography on silica gel (100-200 mesh) using 10% MeOH in DCM as eluant to give racemic #F3 as yellow solid (1.5 g, 24.3%). R$_f$: 0.4 (50% EtOAc in petroleum ether). Chiral HPLC: two enantiomers (61.0%, 39.0%).

LCMS m/z=240.1 (M+H). $^1$H NMR (400 MHz, d$_6$-DMSO): δ 2.19-2.27 (m, 1H), 2.36-2.45 (m, 1H), 3.67-3.84 (m, 3H), 4.02-4.07 (m, 1H), 4.33-4.39 (m, 1H), 5.09 (t, J=4.8 Hz, 1H), 6.83 (d, J=1.6 Hz, 1H), 7.33 (dd, J=8.8 Hz, J=2.0 Hz, 1H), 7.78 (d, J=6.4 Hz, 1H), 7.97 (d, J=8.8 Hz, 1H), 8.36 (d, J=5.6 Hz, 1H).

Step 4. Synthesis of aldehyde (#F4). A solution of #F3 (1.5 g, 6.3 mmol) in EtOAc (45 mL) was cooled to 0° C., and IBX (3.5 g, 12.6 mmol) was added portionwise over 10 minutes. The reaction mixture was stirred at 80° C. for 2 h. The reaction mixture was cooled to room temperature, filtered through a Celite™ pad, and the filtrate was washed with saturated aqueous NaHCO$_3$ solution (100 mL). The organic layer was separated, washed with water, brine, dried over anhydrous sodium sulfate and concentrated under reduced pressure to give #F4 (1.5 g, crude). This was used for the next step without any further purification. R$_f$: 0.5 (60% EtOAc in petroleum ether).

LCMS m/z=238.1 (M+H).

Step 5. Synthesis of products (#24, #25). A solution of #F4 (1.5 g crude material as above, ~6.3 mmol) and cesium fluoride (5.1 g, 34.2 mmol) in THF (30 mL) was cooled to −78° C. Me$_3$SiCF$_3$ (1.5 mL, 9.5 mmol) was added to the mixture dropwise over 10 minutes. The reaction mixture was allowed to warm to room temperature and stirred for 16 h. The reaction mixture was diluted with water (100 mL) and extracted with EtOAc (100 mL×3). The combined organic layers were dried over anhydrous sodium sulfate and concentrated under reduced pressure to give crude material. This was purified by chromatography on silica gel (230-400) using 40% EtOAc in petroleum ether as eluant to provide an inseparable mixture of diastereoisomers (650 mg, 33% yield) which were further separated by chiral preparative HPLC to give target compounds #24 (92 mg, 5%) and #25 (44 mg, 2%) and two other diastereomers.

Final target #24. R$_f$: 0.3 (50% EtOAc in petroleum ether). Chiral HPLC purity: 98.2%.

Final target #25. R$_f$: 0.4 (50% EtOAc in petroleum ether). Chiral HPLC purity: 99.0%.

Example 24

6-{(2R)-2-[(1R)-2,2,2-trifluoro-1-hydroxyethyl]azetidin-1-yl}isoquinoline-1-carbonitrile (#2) (Stereochemistry Arbitrarily Assigned)

LCMS m/z=308.0 (M+1). $^1$H NMR (300 MHz, CDCl$_3$): δ 2.39-2.50 (m, 1H), 2.91-2.97 (m, 1H), 3.83 (q, J=7.8 Hz, 1H), 4.27-4.34 (m, 1H), 4.52-4.66 (m, 1H), 5.29 (br s, 1H, disappeared in D$_2$O exchange), 6.16 (d, J=2.1 Hz, 1H), 6.88 (dd, J=6.3 Hz, J=3.0 Hz, 1H), 7.33 (d, J=5.7 Hz, 1H), 7.81 (d, J=9.0 Hz, 1H), 8.17 (d, J=5.7 Hz, 1H).

Example 25

6-{(2S)-2-[(1S)-2,2,2-trifluoro-1-hydroxyethyl]azetidin-1-yl}isoquinoline-1-carbonitrile (Stereochemistry Arbitrarily Assigned)

LCMS m/z=308.0 (M+1). $^1$H NMR (300 MHz, CDCl$_3$): δ 2.32-2.50 (m, 1H), 2.85-2.30 (m, 1H), 3.87-3.95 (m, 1H), 4.27-4.32 (m, 1H), 4.54-4.67 (m, 2H), 5.29 (br s, 1H, disappeared in D2O exchange), 6.19 (d, J=2.1 Hz, 1H), 6.89 (dd, J=9.0 Hz, J=2.1 Hz, 1H), 7.35 (d, J=5.7 Hz, 1H), 7.83 (d, J=9.0 Hz, 1H), 8.19 (d, J=6.3 Hz, 1H).

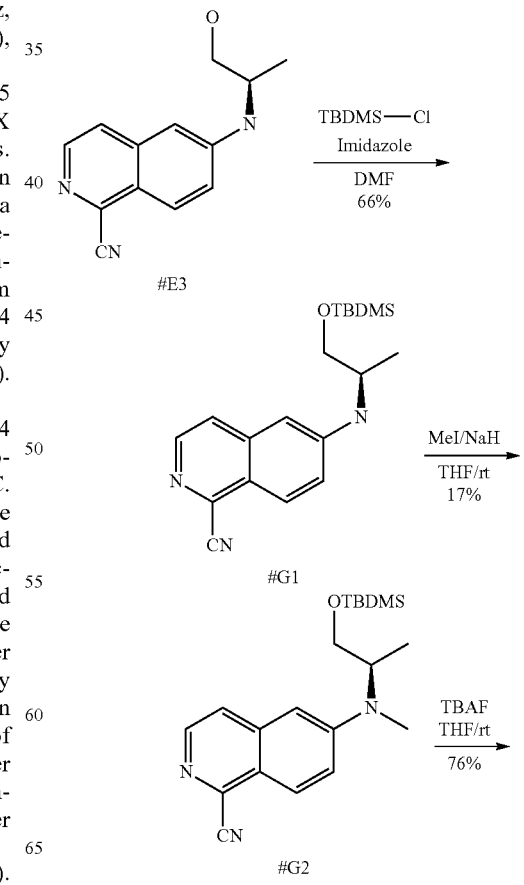

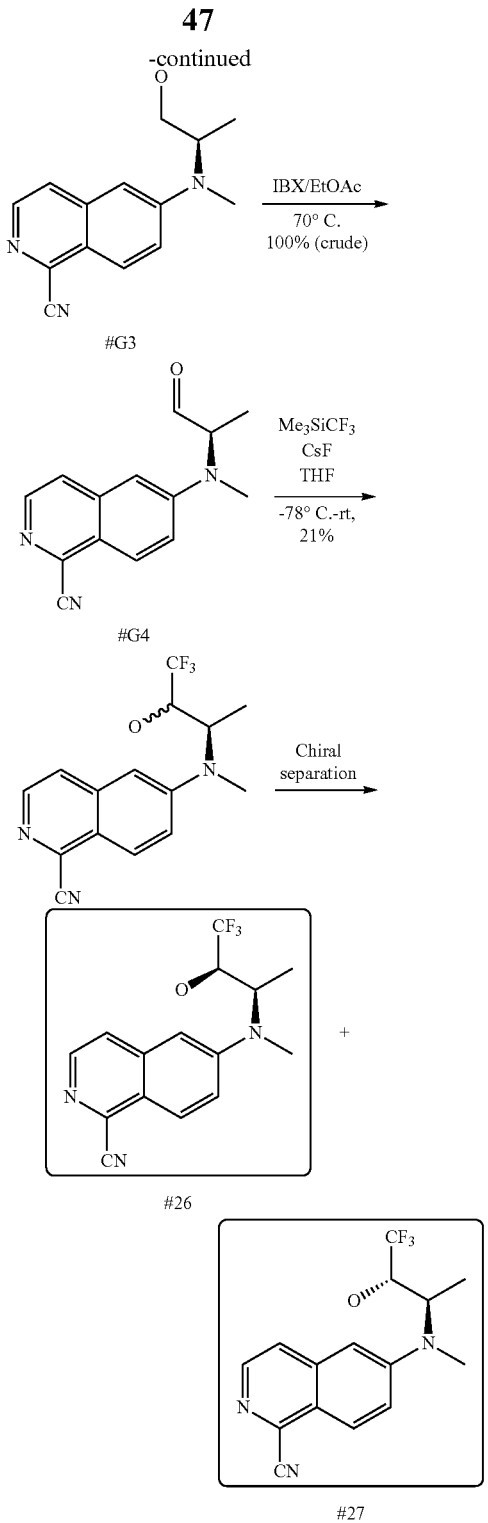

EtOAc in petroleum ether as eluant to give #G1 as brown solid (0.7 g, 66.5%). $R_f$: 0.5 (30% EtOAc in petroleum ether).

$^1$H NMR (400 MHz, CDCl$_3$): δ 0.07 (s, 6H), 0.91 (s, 9H), 1.29 (d, J=6.0 Hz, 3H), 3.65-3.75 (m, 3H), 4.59 (d, J=6.8 Hz, 1H), 6.70 (d, J=2.4 Hz, 1H), 7.05 (dd, J=1.6 Hz, 8.8 Hz, 1H), 7.53 (d, J=6.0 Hz, 1H), 8.04 (d, J=8.8 Hz, 1H), 8.36 (d, J=6.0 Hz, 1H).

Step 2. Synthesis of methyl t-butyldimethylsilyl alcohol (#G2). #G1 (0.70 g, 2.1 mmol) was added dropwise to a solution of NaH (0.20 g, 8.2 mmol) in THF (15 mL) at 0° C. The reaction mixture was stirred for 15 minutes at room temperature then MeI (0.40 mL, 6.2 mmol) was added. The reaction mixture was stirred for 2 h at room temperature and then at 50° C. for 12 h. The reaction mixture was cooled, quenched with ice-cold water (10 mL) and extracted with EtOAc (25 mL×2). All the organic layers were combined, dried over anhydrous Na$_2$SO$_4$ and concentrated under reduced pressure to give crude #G2 as oily solid. The product was purified by chromatography on silica gel (100-200 mesh) using 20% EtOAc in petroleum ether as eluant to give #G2 as yellow solid (0.13 g, 17.3%). $R_f$: 0.6 (30% EtOAc in petroleum ether).

LCMS m/z=356.1 (M+H). $^1$H NMR (400 MHz, CDCl$_3$): δ 0.002 (s, 6H), 0.78 (s, 9H), 1.26 (d, J=6.8 Hz, 3H), 2.94 (s, 3H), 3.65-3.75 (m, 2H), 4.24-4.29 (m, 1H), 6.82 (d, J=2.0 Hz, 1H), 7.45 (dd, J=2.8 Hz, 9.6 Hz, 1H), 7.54 (d, J=5.6 Hz, 1H), 8.08 (d, J=9.2 Hz, 1H), 8.35 (d, J=6.0 Hz, 1H).

Step 3. Synthesis of N-methyl amino alcohol (#G3). A solution of 1M TBAF (2 mL in THF, 2.1 mmol) was added to a solution of #G2 (0.25 g, 1.0 mmol) in THF (10 mL) at room temperature. The reaction mixture was diluted with EtOAc (50 mL), and the organic layer was washed with water and brine. The combined organic layer was dried over anhydrous Na$_2$SO$_4$, filtered and concentrated under reduced pressure to give crude #G3. This was purified by chromatography on silica gel (100-200 mesh) using 100% EtOAc as eluant to give #G3 as a yellow oily liquid (0.13 g, 75.4%). $R_f$: 0.3 (40% EtOAc in petroleum ether).

LCMS m/z=242.0 (M+H). $^1$H NMR (400 MHz, CDCl$_3$): δ 3.05 (s, 3H), 3.68-3.81 (m, 3H), 3.36-3.63 (m, 1H), 6.93 (d, J=2.4 Hz, 1H), 7.50 (dd, J=2.4 Hz, 9.2 Hz, 1H), 7.58 (d, J=5.6 Hz, 1H), 8.12 (d, J=1.2 Hz, 1H), 8.38 (q, 1H).

Step 4. Synthesis of N-methyl amino aldehyde (#G4). A solution of #G3 (0.13 g, 0.54 mmol) in EtOAc (5 mL) was cooled to 0° C., and IBX (0.38 g, 1.3 mmol) was added portionwise. The reaction mixture was stirred at 70° C. for 2 h, and then it was cooled to room temperature, filtered through a Celite™ pad and washed with EtOAc (25 mL). The filtrate was washed with aqueous saturated NaHCO$_3$ solution (10 mL), water and brine. The organic layer was separated, dried over anhydrous sodium sulfate and concentrated under reduced pressure to give #G4 (0.13 g, crude). The product was used for the next step without further purification. $R_f$: 0.5 (60% EtOAc in petroleum ether).

LCMS m/z=240.0 (M+H).

Step 5. Synthesis of products (#26, #27). A solution of #G4 (0.13 g, crude, 0.54 mmol), cesium fluoride (0.40 g, 2.7 mmol) in THF (5 mL) was cooled to −78° C., and Me$_3$SiCF$_3$ (0.12 mL, 0.80 mmol) was added dropwise over 10 minutes. The reaction mixture was allowed to warm and stirred at room temperature for 16 h. Water (2 mL) was added, and the mixture was diluted with EtOAc (100 mL), washed with water, brine, dried over anhydrous sodium sulfate and concentrated under reduced pressure to get crude mixture of products. The isomers were separated by chiral preparative HPLC to give compounds #26 (23 mg, 13.6%) and #27 (11 mg, 6.5%). Total yield (34 mg, 21%).

Step 1. Synthesis of t-butyldimethylsilyl alcohol (#G1). t-Butyldimethylsilyl chloride (0.9 g, 6.2 mmol) was added to a solution of #E3 (0.7 g, 3.1 mmol) and imidazole (0.6 g, 9.2 mmol) in DMF (10 mL) at 0° C. The reaction mixture was stirred at room temperature for 12 h. After consumption of the starting material, the reaction mixture was diluted with water (50 mL) and extracted with EtOAc (50 mL×3). The combined organic layers were dried and concentrated under reduced pressure to give crude #G1. The product was purified by chromatography on silica gel (100-200 mesh) using 20%

26. $R_f$: 0.6 (50% EtOAc in petroleum ether). Chiral HPLC purity: 97.9%.

27. $R_f$: 0.6 (50% EtOAc in petroleum ether). Chiral HPLC purity: 98.5%.

Example 26

6-{methyl[(2R,3R)-4,4,4-trifluoro-3-hydroxybutan-2-yl]amino}isoquinoline-1-carbonitrile (Stereochemistry Arbitrarily Assigned)

LCMS m/z=310.1 (M+1). $^1$H NMR (300 MHz, $d_6$-DMSO): δ 1.32 (d, J=6.3 Hz, 3H), 2.94 (s, 3H), 4.20-4.26 (m, 1H), 4.40-4.45 (m, 1H), 6.67 (d, J=6.9 Hz, 1H), 7.10 (s, 1H), 7.64 (d, J=9.9 Hz, 1H), 7.85 (d, J=5.7 Hz, 1H), 8.02 (d, J=9.0 Hz, 1H), 8.38 (d, J=5.4 Hz, 1H).

Example 27

6-{methyl[(2R,3S)-4,4,4-trifluoro-3-hydroxybutan-2-yl]amino}isoquinoline-1-carbonitrile (Stereochemistry Arbitrarily Assigned)

LCMS m/z=310.1 (M+1). $^1$H NMR (300 MHz, $d_6$-DMSO): δ 1.30 (d, J=6.3 Hz, 3H), 2.97 (s, 3H), 4.22-4.25 (m, 1H), 4.49-4.53 (m, 1H), 6.55 (d, J=6.3 Hz, 1H), 7.07 (s, 1H), 7.65 (d, J=7.5 Hz, 1H), 7.83 (d, J=7.6 Hz, 1H), 8.04 (d, J=9.0 Hz, 1H), 8.37 (d, J=9.2 Hz, 1H).

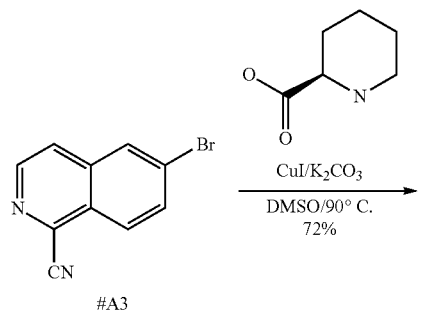

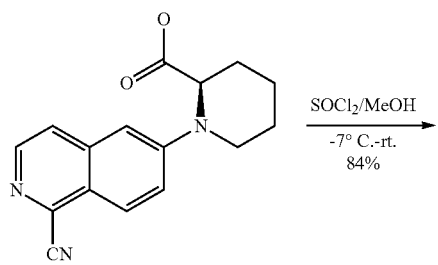

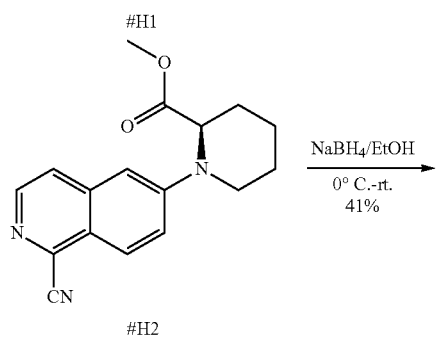

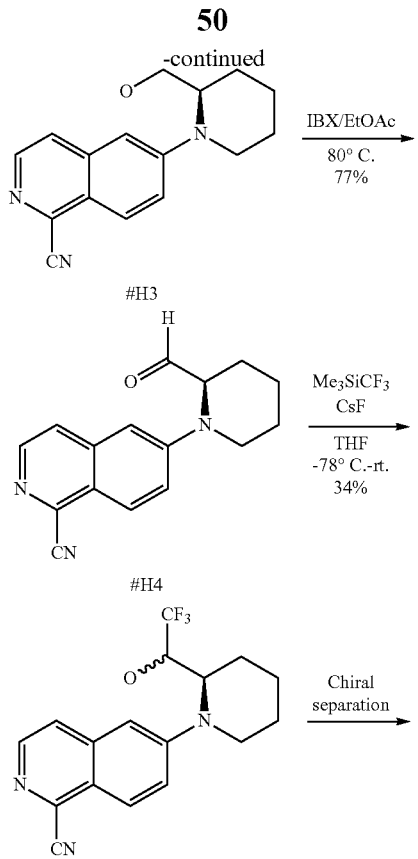

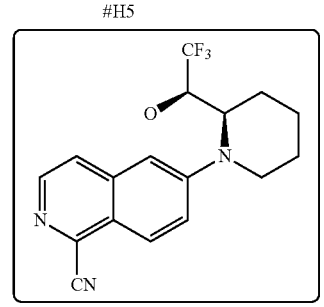

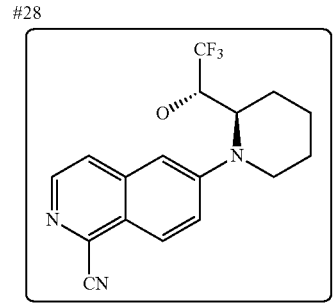

Step 1. Synthesis of product (#H1). A mixture of 6-bromoisoquinoline-1-carbonitrile #A3 (4.5 g, 19.3 mmol), (R)-piperidine carboxylic acid (2.7 g, 20.9 mmol), CuI (3.2 g, 1.9 mmol) and $K_2CO_3$ (5.4 g, 39.1 mmol) in DMSO (15 mL) was heated at 90° C. for 5 h. The consumption of 6-bromoisoquinoline-1-carbonitrile was observed on TLC. The reaction mixture was cooled to room temperature, filtered through a Celite™ pad, rinsed with EtOAc and the filtrate was diluted with water (200 mL). The filtrate was washed with EtOAc (100 mL×3). The combined organic layers were dried over anhydrous sodium sulfate, filtered and concentrated under reduced pressure to give crude material. This was triturated with pentane to give #H1 as a pure yellow solid (4 g, 72%). $R_f$: 0.1 (EtOAc).

LCMS m/z=281.9 (M+H). $^1$H NMR (300 MHz, $d_6$-DMSO): δ 1.56-1.89 (m, 3H), 2.26 (d, J=12.6 Hz, 1H), 2.71 (dd, J=15.3 Hz, 17.4 Hz, 1H), 3.16 (td, J=12.6 Hz, 3.6 Hz, 1H), 3.90 (d, J=11.7 Hz, 1H), 4.99 (d, J=3.3 Hz, 1H), 7.26 (d, J=2.7 Hz, 1H), 7.75 (dd, J=9.2 Hz, J=2.4 Hz, 1H), 7.86 (d, J=5.4 Hz, 1H), 7.98 (d, J=9.0 Hz, 1H), 8.41 (d, J=6.3 Hz, 1H), 12.60 (br s, 1H).

Step 2. Synthesis of methyl ester product (#H2). Thionyl chloride (2.0 mL, 28.6 mmol) was added to a solution of #H1 (4.0 g, 14.3 mmol) in methanol at 0° C. The reaction mixture was stirred at room temperature for 16 h. After the depletion of the starting material, the reaction was cooled to 0° C. and treated with solid NaHCO$_3$. The mixture was filtered to remove solids, and the filtrate was concentrated under reduced pressure. The residue was diluted with EtOAc, washed with water and brine. The organic layer was dried over anhydrous Na$_2$SO$_4$ and concentrated under reduced pressure to give crude material. This was purified by column chromatography on silica gel (100-200) using 20% EtOAc in petroleum ether as eluent to give #H2 (3.5 g, 84%). $R_f$: 0.6 (50% EtOAc in petroleum ether).

LCMS m/z=296.0 (M+H). $^1$H NMR (400 MHz, $d_6$-DMSO): δ 1.56-1.61 (m, 1H), 1.71-1.89 (m, 3H), 2.24 (d, J=12 Hz, 1H), 2.73 (d, J=15.2 Hz, 1H), 2.87 (d, J=15.2 Hz, 1H), 3.57 (s, 3H), 3.91 (d, J=11.2 Hz, 1H), 5.14 (d, J=3.6 Hz, 1H), 7.29 (d, J=2.4 Hz, 1H), 7.76 (dd, J=2.8 Hz, 9.6 Hz, 1H), 7.87 (d, J=5.6 Hz, 1H), 7.99 (d, J=9.6 Hz, 1H), 8.43 (d, J=6.0 Hz, 1H).

Step 3. Synthesis of alcohol (#H3). A solution of #D2 (3.5 g, 11.9 mmol) in ethanol (35 mL) was cooled to 0° C., and NaBH$_4$ (0.90 g, 23.7 mmol) was added portionwise over 30 minutes. The reaction mixture was stirred at room temperature for 16 h. Water (10 mL) was added to the reaction mixture at 0° C., and ethanol was removed under reduced pressure. The resulting crude material was diluted with EtOAc (300 mL), and washed with water. The organic layer was dried over Na$_2$SO$_4$ and concentrated under reduced pressure to give crude material. This was purified by chromatography on silica gel (100-200) using 30% EtOAc in petroleum ether as eluent to give #H3 (1.3 g, 41%). $R_f$: 0.5 (50% EtOAc in petroleum ether).

LCMS m/z=268.0 (M+H). $^1$H NMR (300 MHz, $d_6$-DMSO): δ 1.51-1.64 (m, 4H), 1.77 (d, J=10.5, 1H), 1.94 (d, J=5.7 Hz, 1H), 3.04-3.12 (m, 1H), 3.48-3.66 (m, 2H), 3.81 (d, J=13.2 Hz, 1H), 4.22 (br s, 1H), 4.74 (t, 1H), 7.19 (s, 1H), 7.73 (dd, J=2.1 Hz, 9.9 Hz, 1H), 7.79 (d, J=5.7 Hz, 1H), 7.94 (d, J=9.9 Hz, 1H) 8.36 (d, J=5.4 Hz, 1H).

Step 4. Synthesis of aldehyde (#H4). A solution of #H3 (1.3 g, 4.9 mmol) in EtOAc (10 mL) was cooled to 0° C., and IBX (2.7 g, 9.7 mmol) was added portionwise over 10 minutes. The reaction mixture was stirred at 80° C. for 2 h, cooled to room temperature, and filtered through Celite™ pad. The filtrate was washed with saturated aqueous NaHCO$_3$ solution (30 mL). The organic layer was separated, washed with water, brine, dried over anhydrous Na$_2$SO$_4$ and concentrated under reduced pressure to provide #H4 (1 g, crude). This material was used for the next step without any further purification. $R_f$: 0.6 (50% EtOAc in petroleum ether).

$^1$H NMR (300 MHz, $d_6$-DMSO): δ 1.48-1.52 (m, 1H), 1.53-1.74 (m, 3H), 3.01-3.20 (m, 1H), 3.97-4.12 (m, 1H), 5.07 (d, J=4.8 Hz, 1H), 7.32 (s, 1H), 7.75 (d, J=9.6 Hz, 1H), 7.84 (d, J=5.4, 1 H), 7.99 (d, J=9.0 Hz, 1H), 8.42 (d, J=5.4 Hz, 1H), 9.67 (s, 1H).

Step 5. Synthesis of products (#28, #29). A solution of #D4 (1.0 g, crude, 3.8 mmol), CsF (3.1 g, 20.5 mmol) in THF (10 mL) was cooled to −78° C. Me$_3$SiCF$_3$ (0.47 mL, 6.0 mmol) was added dropwise over 10 minutes. The reaction mixture was stirred at room temperature for 16 h. Water (20 mL) was added at 0° C. The mixture was washed with EtOAc (100 mL×3). The combined organic layer was dried over anhydrous sodium sulfate and concentrated under reduced pressure to give crude material. It was purified by chromatography on silica gel (230-400 mesh) using 20% EtOAc in petroleum ether as eluent to give a mixture of final compounds (500 mg, 94% LCMS purity). This was again purified by chiral preparative HPLC to get target compounds #28 (303 mg, 24%) and #29 (104 mg, 8%). Total yield (407 mg, 32%). Final target GCSW#193966:

28. $R_f$: 0.5 (40% EtOAc in petroleum ether). Chiral HPLC purity: (99.1%).

29. $R_f$:0.5 (40% EtOAc in petroleum ether). Chiral HPLC purity: (98.7%)

Example 28

6-{(2R)-2-[(1R)-2,2,2-trifluoro-1-hydroxyethyl]piperidin-1-yl}isoquinoline-1-carbonitrile (Stereochemistry Arbitrarily Assigned)

LCMS m/z=336.1 (M+1). $^1$H NMR (300 MHz, $d_6$-DMSO): δ 1.61-1.77 (m, 6H), 3.24 (d, J=11.1 Hz, 1H), 3.90 (d, J=13.5 Hz, 1H), 4.43 (d, J=9.0 Hz, 1H), 4.56 (m, 1H), 6.37 (d, J=6.3 Hz, 1H), 7.21 (d, J=2.1 Hz, 1H), 7.70 (dd, J=2.4 Hz, 9.2 Hz, 1H), 7.81 (d, J=5.7 Hz, 1H), 7.95 (d, J=9.0 Hz, 1H), 8.36 (d, J=5.4 Hz, 1H).

Example 29

6-{(2R)-2-[(1S)-2,2,2-trifluoro-1-hydroxyethyl]piperidin-1-yl}isoquinoline-1-carbonitrile (Stereochemistry Arbitrarily Assigned)

LCMS m/z=336.1 (M+1). $^1$H NMR (300 MHz, $d_6$-DMSO): δ 1.49-1.68 (m, 4H), 1.76-1.85 (m, 1H), 2.08 (d, J=13.5 Hz, 1H), 3.25-3.29 (m, 1H), 3.92 (d, J=13.8 Hz, 1H), 4.36 (br s, 1H), 4.55-4.60 (m, 1H), 6.64 (d, J=7.2 Hz, 1H), 7.24 (d, J=2.1 Hz, 1H), 7.65 (d, J=2.1 Hz, 9.6 Hz, 1H), 7.83 (d, J=5.4 Hz, 1H), 7.99 (d, J=9.6 Hz, 1H), 8.38 (d, J=5.4 Hz, 1H).

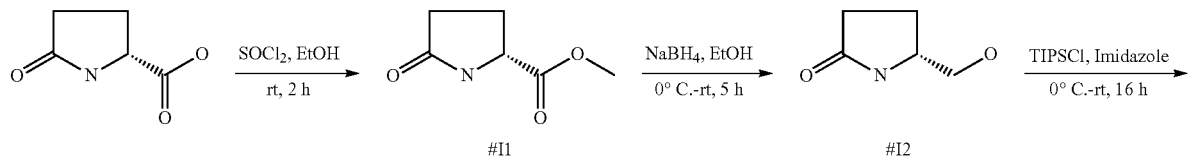

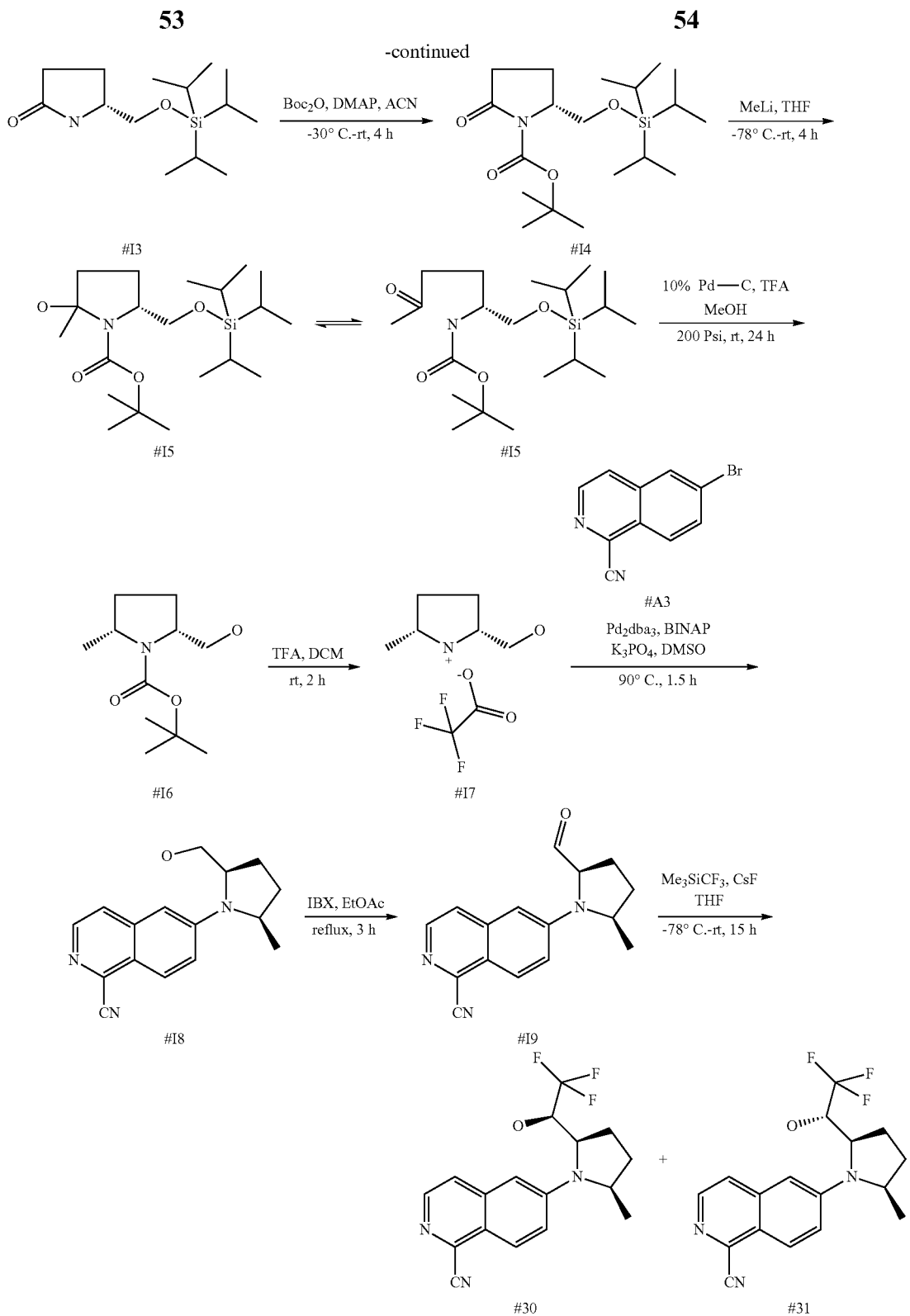

Step 1. Synthesis of amino ester (#I1). Thionyl chloride (56.0 mL, 775.0 mmol) was added dropwise to the solution of amino acid (100.0 g, 775.0 mmol) in methanol (1.3 L) at 0° C. and the reaction mixture allowed to stirred at room temperature for 2 h. Excess methanol was removed under vacuum to give a crude mixture. It was dissolved in DCM, washed with saturated aqueous $NaHCO_3$ solution, dried over $Na_2SO_4$, and concentrated to afford crude #I1 as a yellow liquid (80 g, 72%). $R_f$: 0.4 (10% methanol in DCM, $KMnO_4$ active).

$^1$H NMR (300 MHz, $d_6$-DMSO): δ 1.92-2.01 (m, 1H), 2.03-2.16 (m, 2H), 2.27-2.37 (m, 1H), 3.67 (s, 3H), 4.16-4.20 (m, 1H), 8.00 (s, 1H).

Step 2. Synthesis of amino alcohol (#I2). NaBH$_4$ (21.1 g, 558.9 mmol) was added portionwise to the solution of #I1 (80.0 g, 558.9 mmol) in ethanol (800 mL) at 0° C. for 30 minutes and stirring was continued at room temperature for 5 h. The reaction mixture was acidified with concentrated HCl, filtered through a Celite™ pad and washed with ethanol.

The ethanol was removed under vacuum to give #I2 as a colorless viscous liquid (48 g, 75%). R$_f$: 0.3 (50% EtOAc: petroleum ether, KMnO$_4$ active).

LCMS m/z=116.0 (M+H). $^1$H NMR (300 MHz, d$_6$-DMSO): δ 1.65-1.78 (m, 1H), 1.90-2.13 (m, 3H), 2.27-2.37 (m, 1H), 3.30 (d, 2H, J=6 Hz), 3.46-3.56 (m, 1H), 7.59 (s, 1H).

Step 3. Synthesis of TIPs ether (#I3). TIPSCl (55.5 mL, 260.6 mmol) was added dropwise to a solution of #I2 (25.0 g, 217.1 mmol) and imidazole (19.2 g, 282.2 mmol) in DCM (500 mL) at 0° C., and the reaction mixture was allowed to stir at room temperature for 16 h. The reaction mixture was quenched with water, DCM layer separated and concentrated under reduced pressure. The residue was dissolved in EtOAc, washed with 10% aqueous citric acid solution, followed by water and brine. The organic layer was separated, dried over Na$_2$SO$_4$, concentrated and was purified by chromatography on silica gel (100-200 mesh) using 20-40% EtOAc and petroleum ether to afford #I3 as a pale yellow liquid (20 g, 37%). R$_f$: 0.4 (50% EtOAc/petroleum ether, KMnO$_4$ active)

$^1$H NMR (300 MHz, d$_6$-DMSO): δ 1.00-1.05 (m, 21H), 1.77-1.84 (m, 1H), 2.03-2.17 (m, 3H), 3.31-3.62 (m, 3H), 7.50 (s, 1H).

Step 4. Synthesis of N-Boc TIPs ether (#I4). (Boc)$_2$O (16.80 mL, 73.67 mmol) was added to a stirred solution of #I3 (20.0 g, 73.7 mmol) and DMAP (0.90 g, 7.4 mmol) in acetonitrile (200 mL) at −30° C. and the reaction mixture was stirred for 30 minutes and then stirring was continued at room temperature for 16 h. The reaction mixture was concentrated under reduced pressure to give crude material, which was purified by column chromatography on silica gel (100-200 mesh) using 10% EtOAc in petroleum ether to afford #I4 as a light brown liquid (18 g, 66%). R$_f$: 0.5 (20% EtOAc in petroleum ether, KMnO$_4$ active).

$^1$H NMR (400 MHz, d$_6$-DMSO): δ 1.00-1.05 (m, 21H), 1.43 (s, 9H), 1.84-1.90 (m, 1H), 2.08-2.16 (m, 1H), 2.24-2.32 (m, 1H), 2.53-2.58 (m, 1H), 3.73 (dd, 1H, J=2.0, 10.0 Hz), 4.00 (dd, 1H, J=3.2, 10.0 Hz), 4.13 (d, 1H, J=8.8 Hz).

Step 5. Methyl addition adduct N-Boc TIPs protected alcohol (#I5). MeLi in DCM (20.0 mL, 2M, 60.0 mmol) was added dropwise to a solution of #I4 (20.0 g, 53.8 mmol) in dry THF (100 mL) at −78° C. and stirring was continued for 4 h. The reaction mixture was quenched with NH$_4$Cl solution, extracted with EtOAc, dried over Na$_2$SO$_4$, concentrated to give #I5 as a light brown liquid (20 g, 95%) which was used for the next step without further purification. R$_f$: 0.6 (30% EtOAc/petroleum ether, KMnO$_4$ active).

$^1$H NMR (300 MHz, d$_6$-DMSO): δ 0.97-1.02 (m, 21H), 1.17 (s, 9H), 1.73-1.75 (m, 2H), 2.05 (s, 3H), 2.40-2.45 (m, 2H), 3.45-3.55 (m, 3H), 6.52-6.54 (m, 1H).

Step 6. Dehydroxylation product of N-Boc alcohol (#I6). A mixture of #I5 (7.0 g, 18.1 mmol) and 10% Pd/C (1.8 g) in 10% trifluoroacetic acid/MeOH (80 mL) was shaken in a Parr apparatus under hydrogen atmosphere at 200 psi at room temperature for 24 h. The reaction mixture was filtered through a Celite™ pad, washed with EtOAc and concentrated under reduced pressure to give crude mixture. This was purified by chromatography on silica gel (100-200 mesh) using 10-30% EtOAc in petroleum ether to give #I6 as a yellow liquid (2.3 g, 63%). R$_f$: 0.4 (30% EtOAc/petroleum ether, KMnO$_4$ active).

$^1$H NMR (300 MHz, d$_6$-DMSO) δ 1.11 (d, J=6 Hz, 3H), 1.39 (s, 9H), 1.45-1.51 (m, 1H), 1.76-1.98 (m, 3H), 3.18-3.34 (m, 1H), 3.46-3.49 (m, 2H), 3.65-3.74 (m, 2H).

Step 7. Synthesis of amino alcohol trifluoroacetic acid salt (#I7). Trifluoroacetic acid (40 mL) was added dropwise to a solution of #I6 (6.5 g, 30.2 mmol) in DCM (40 mL) at room temperature and the reaction mixture was stirred for 2 h. The solvents were evaporated under reduced pressure to get residue mixture which was co-distilled with methanol to afford #I7 as a pale yellow liquid (6.5 g, 94%). R$_f$: 0.2 (20% MeOH in DCM, KMnO$_4$ active).

LCMS m/z=116.1 (M+H) (free base). $^1$H NMR (300 MHz, d$_6$-DMSO): δ 1.28 (d, 3H, J=6.3 Hz), 1.48-1.68 (m, 2H), 1.92-2.11 (m, 2H), 3.49-3.64 (m, 4H), 8.15 (br s, 1H), 9.3 (br s, 1H).

Step 8. Synthesis of coupling product (#I8). #I7 (3.4 g, 29.9 mmol) was added to degassed DMSO. K$_3$PO$_4$ (7.3 g, 34.5 mmol) was added to the solution and stirring was continued for 5 minutes, followed by the addition of Pd$_2$(dba$_3$) (0.27 g, 0.30 mmol), BINAP (0.55 g, 0.88 mmol) and 6-bromoisoquinoline-1-carbonitrile #A3 (2.3 g, 9.9 mmol) under an argon atmosphere. The resulting reaction mixture was heated at 90° C. under argon atmosphere for 1.5 h. The reaction mixture was cooled to room temperature, diluted with EtOAc, and filtered through a Celite™ pad. The filtrate was washed with water followed by brine. The organic layer was dried over Na$_2$SO$_4$, evaporated under reduced pressure to get the crude mixture which was chromatographed on silica gel (100-200 mesh) using 20-80% EtOAc in petroleum ether as eluent to give #I8 as a yellow solid (3.8 g, 48%). R$_f$: 0.2 (50% EtOAc in petroleum ether, UV active)

LCMS m/z=268.4 (M+H). $^1$H NMR (400 MHz, d$_6$-DMSO): δ 1.27 (d, J=6 Hz, 3H), 1.72-1.79 (m, 1H), 1.91-2.03 (m, 2H), 2.11-2.19 (m, 1H), 3.38-3.44 (m, 1H), 3.58-3.63 (m, 1H), 3.93-4.03 (m, 2H), 4.94 (t, J=5.6 Hz, 1H), 6.94 (d, J=2 Hz, 1H), 7.47 (dd, J=2.4, 9.2 Hz, 1H), 7.80 (d, J=5.6 Hz, 1H), 7.94 (d, J=9.6 Hz, 1H), 8.33 (d, J=6.4 Hz, 1H).

Step 9. Synthesis of aldehyde (#I9). Mixture of #I8 (3.8 g, 14.0 mmol) and IBX (7.8 g, 28.0 mmol) in EtOAc (150 mL) was refluxed for 3 h. The reaction mixture was cooled to room temperature, filtered through a Celite™ pad and washed with EtOAc. The organic layer was washed with saturated aqueous NaHCO$_3$ solution, dried over Na$_2$SO$_4$ and evaporated in vacuo to obtain crude mixture. This was triturated with pentane to afford #I9 as light yellow solid (3.1 g, 82%) which was used for the next step without further purification. R$_f$: 0.4 (50% EtOAc/petroleum ether, UV active).

LCMS m/z=266.2 (M+H). $^1$H NMR (300 MHz, d$_6$-DMSO): δ 1.28 (d, J=6.3 Hz, 3H), 1.66-1.68 (m, 1H), 2.16-2.26 (m, 3H), 4.20-4.22 (m, 1H), 4.52-4.55 (m, 1H), 6.89 (d, J=2.1 Hz, 1H), 7.35 (dd, J=2.7, 9.6 Hz, 1H), 7.82 (d, J=5.7 Hz, 1H), 8.00 (d J=9 Hz, 1H), 8.37 (d, J=5.7 Hz, 1H), 9.59 (s, 1H).

Step 10. Synthesis of products (#30, #31). Me$_3$SiCF$_3$ (2.30 g, 16.35 mmol) was added to a solution of #I9 (3.1 g, 16.4 mmol) and CsF (16.7 g, 109.8 mmol) in THF (100 mL) at −78° C. and the reaction mixture was allowed to warm and stirred at room temperature for 15 h. Ethanol (25 mL) was added to the reaction mixture and stirring was continued at room temperature for 3 h. The reaction mixture was poured into water, extracted with EtOAc, dried over Na$_2$SO$_4$, concentrated under reduced pressure to give a crude product mixture (3.8 g) which was purified by preparative HPLC to afford diastereomers #30 (1.1 g) and #31 (1.1 g). R$_f$: 0.3 and 0.4 in 30% EtOAc in petroleum ether simultaneously. The absolute stereochemistry was established using crystallography.

Example 30

6-{(2R,5R)-2-methyl-5-[(1R)-2,2,2-trifluoro-1-hydroxyethyl]pyrrolidin-1-yl}isoquinoline-1-carbonitrile LCMS m/z=336.3 (M+1). $^1$H NMR (400 MHz, d$_6$-DMSO): δ 1.32 (d, J=6.3 Hz, 3H), 1.75-1.83 (m, 1H), 1.91-1.96 (m, 1H), 1.97-2.08 (m, 1H), 2.34-2.39 (m, 1H), 4.05-4.10 (m, 1H), 4.22-4.27 (m, 1H), 4.33-4.38 (m, 1H), 6.62 (d, J=6.6 Hz, 1H), 6.86 (d, J=2.1 Hz, 1H), 7.42 (dd, J=2.7, 9.6 Hz, 1H), 7.87 (d, J=5.4 Hz, 1H), 8.05 (d, J=9.3 Hz, 1H), 8.37 (d, J=5.7 Hz, 1H). Chiral HPLC purity: 97.9%.

Example 31

6-{(2R,5R)-2-[(1R)-1-hydroxyethyl]-5-methylpyrrolidin-1-yl}isoquinoline-1-carbonitrile (Stereochemistry Arbitrarily Assigned)

LCMS m/z=336.3 (M+1). $^1$H NMR (400 MHz, d$_6$-DMSO): δ 1.35 (d, J=6.3 Hz, 3H), 1.79-1.88 (m, 1H), 1.93-1.98 (m, 2H), 2.34-2.37 (m, 1H), 3.96-4.01 (m, 1H), 4.03-4.13 (m, 1H), 4.22-4.27 (m, 1H), 6.64 (d, J=6.6 Hz, 1H), 7.03 (d, J=2.1 Hz, 1H), 7.55 (dd, J=2.3, 9.3 Hz, 1H), 7.83 (d, J=5.7 Hz, 1H), 7.97 (d, J=9 Hz, 1H), 8.35 (d, J=6 Hz, 1H). Chiral HPLC purity: 99.2%.

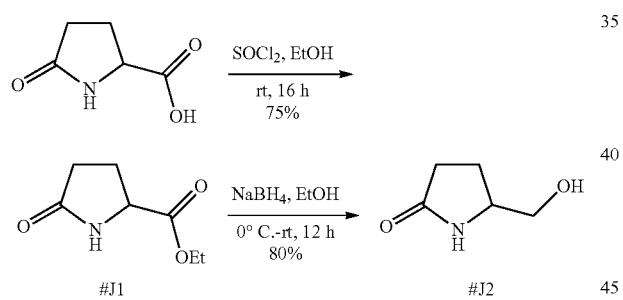

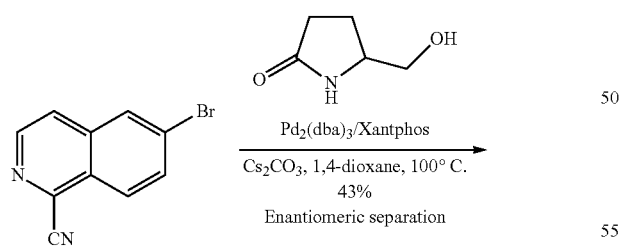

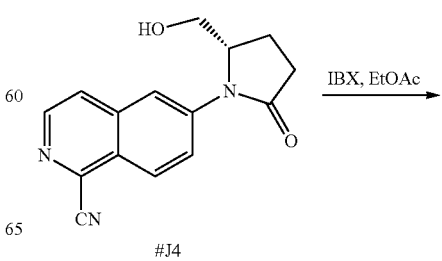

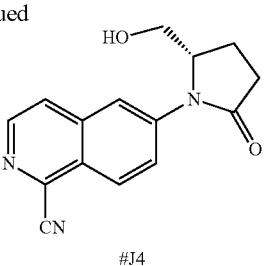

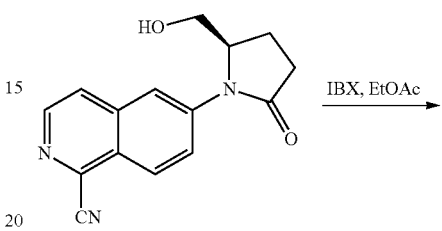

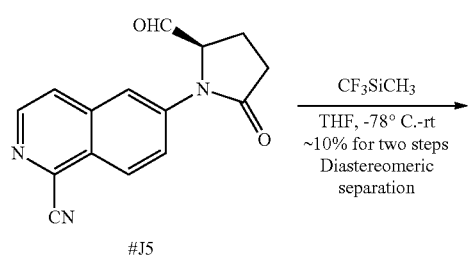

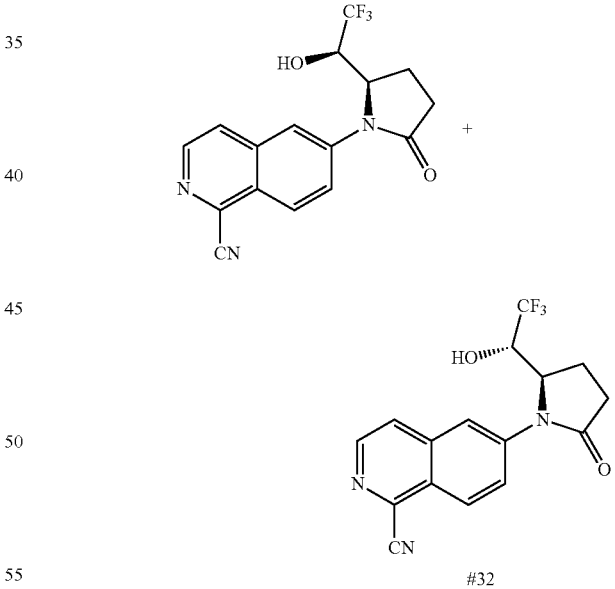

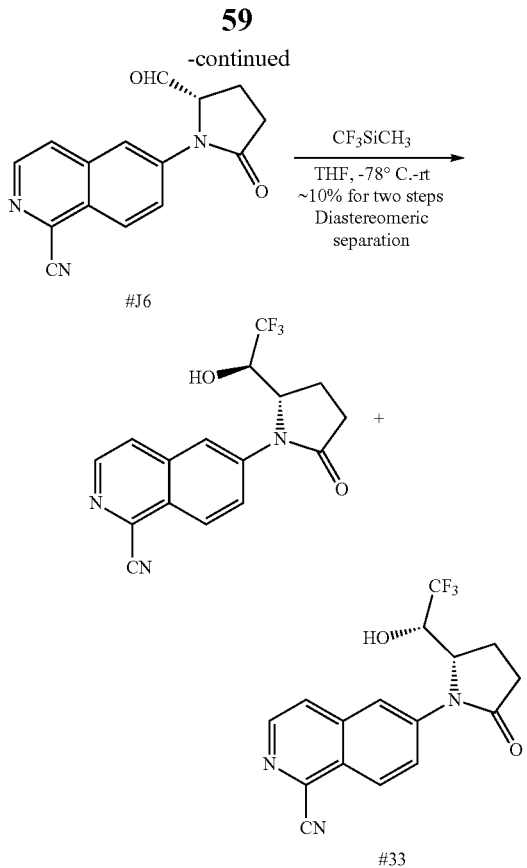

Step 1. Synthesis of ester (#J1). Thionyl chloride (5.6 mL, 77.0 mmol) was slowly added to a solution of acid (10.0 g, 77.0 mmol) in ethanol (130 mL) at 0° C. The reaction mixture was allowed to stir at room temperature overnight. The mixture was concentrated in vacuo to remove ethanol. The crude residue was diluted with DCM washed with saturated aqueous NaHCO$_3$ solution, water and brine. The organic layer was dried over Na$_2$SO$_4$ and concentrated to give #J1 (9 g, 75%) as yellow liquid. R$_f$: 0.3 EtOAc (KMnO$_4$ active).

GCMS m/z=157.1 (M).

Step 2. Synthesis of lactam carbinol (#J2). NaBH$_4$ (1.2 g, 30.0 mmol) was added slowly to a solution of #J1 (8.0 g, 50.0 mmol) in ethanol (60 mL) at 0° C. portionwise. The reaction mixture was allowed to stir at room temperature for 6 h. The mixture was quenched with concentrated HCl and the precipitated solid was filtered and purified by column chromatography on 100-200 silica gel with 8% methanol in DCM as eluent to give pure #J2 (4.7 g, 80%) as pale yellow thick liquid. R$_f$: 0.1 (20% MeOH in DCM, KMnO$_4$ active).

$^1$H NMR (400 MHz, d$_6$-DMSO) δ 1.65-1.78 (m, 1H); 1.96-2.15 (m, 3H); 3.25 (m, 2H); 3.46 (m, 1H); 3.92 (br. s., 1H); 7.58 (br. s., 1H).

Step 3. Synthesis of carbinol products (#J3, #J4). Pd$_2$(dba)$_3$ (55.0 mg, 0.06 mmol), xanthphos (110.0 mg, 0.19 mmol) and Cs$_2$CO$_3$ (2.0 g, 6.4 mmol) were added to a mixture of #J2 (0.50 g, 2.1 mmol) and 6-bromoisoquinoline-1-carbonitrile (0.50 g, 4.3 mmol) in 1,4-dioxane (10 mL) under nitrogen atmosphere. The reaction mixture was heated to 110° C. for 2.5 h. After the consumption of the starting material, the mixture was diluted with EtOAc, washed with water and brine. The organic layer was dried over Na$_2$SO$_4$ and concentrated in vacuo to get crude material. This was purified by column chromatography using 100-200 silica gel and eluted with 70% EtOAc in petroleum ether to get pure #J3 and #J4 as a racemic mixture. The reaction was repeated three times. The combined crude products were separated by chiral prep HPLC to give #J3 (350 mg) and #J4 (350 mg) as pale brown solids. Absolute configuration was arbitrarily assigned as shown. R$_f$: 0.2 (EtOAc).

LCMS m/z=268.1 (M+H). $^1$H NMR (400 MHz, CDCl$_3$): δ 2.22 (m, 1H), 2.39 (m, 1H), 2.62 (m, 1H), 2.84 (m, 1H), 3.73 (m, 1H), 3.83 (m, 1H), 4.60 (m, 1H), 7.85 (d, J=5.6 Hz, 1H), 8.00 (dd, J=1.6, 9.2 Hz, 1H), 8.20 (d, J=2.0 Hz, 1H), 8.34 (d, J=9.2 Hz, 1H), 8.61 (d, J=5.6 Hz, 1H).

Step 4. Synthesis of aldehyde (#J5). IBX (587.0 mg, 2.1 mmol) was added to a stirred solution of #J3 (280.0 mg, 1.0 mmol) in EtOAc (10 mL) at room temperature. The reaction mixture was heated to 80° C. for 3 h. After completion of the reaction, the mixture was filtered through a Celite™ pad and was washed with EtOAc. The filtrate was washed with saturated aqueous NaHCO$_3$ solution, dried over Na$_2$SO$_4$, filtered and concentrated to give #J5 (300 mg crude) as a pale yellow liquid used in the next step without further purification. R$_f$: 0.3 (EtOAc).

LCMS m/z=266.1 (M+H).

Step 5. Synthesis of product (#32). Me$_3$SiCF$_3$ (224 mg, 1.58 mmol) was added dropwise to a stirred suspension of compound #J5 (300.0 mg, 1.1 mmol) and CsF (950.0 mg, 5.9 mmol) in THF (10 mL) at −78° C. very slowly. Then, the reaction mixture was allowed to warm to room temperature and stir overnight. The mixture was quenched with water and extracted with EtOAc. The organic layer was dried over Na$_2$SO$_4$, filtered and concentrated in vacuo to give crude compound (diastereomeric mixture). This was purified by column chromatography on silica gel (100-200 mesh). Elution with 15% EtOAc in petroleum ether provides the first eluting hydroxyl center diastereomer and 40% EtOAc in petroleum ether gave the other diastereomer, target #32 (45 mg, 12%). Hydroxyl center diastereomer (10 mg, 3%). R$_f$: 0.7 (other diastereomer) and 0.5 (#32) (EtOAc).

Example 32

6-{(5R)-2-oxo-5-[(1S)-2,2,2-trifluoro-1-hydroxyethyl]pyrrolidin-1-yl}isoquinoline-1-carbonitrile (Stereochemistry Arbitrarily Assigned)

LCMS m/z=336.0 (M+1). $^1$H NMR (400 MHz, d$_6$-DMSO) δ 2.42-2.50 (m, 2H); 2.72-2.73 (m, 1H); 4.28-4.30 (m, 1H); 4.97-5.03 (m, 1H); 6.68 (d, J=6.9 Hz, 1H); 8.11-8.28 (m, 4H); 8.65 (d, J=5.4 Hz, 1H).

Step 6. Synthesis of aldehyde (#J6). IBX (730.0 mg, 2.6 mmol) was added to a stirred solution of #J4 (350 mg, 1.3 mmol) in EtOAc (10 mL) at room temperature. The reaction mixture was heated to 80° C. for 3 h. After completion of reaction, the mixture was filtered through a Celite™ pad and washed with EtOAc. The filtrate was washed with saturated aqueous NaHCO$_3$ solution, dried over Na$_2$SO$_4$, filtered and concentrated to give crude #J6 (400 mg crude) as a pale yellow liquid. The crude compound was used without further purification in the next step. R$_f$: 0.3 (EtOAc).

LCMS m/z=266.1 (M+H).

Step 7. Synthesis of product (#33). Me$_3$SiCF$_3$ (297.0 mg, 2.1 mmol) was added dropwise to a stirred suspension of #J6 (400.0 mg, 1.5 mmol) and CsF (1.2 g, 7.9 mmol) in THF (10 mL) at −78° C. very slowly. The reaction mixture was allowed to warm to room temperature and stirred overnight. The mixture was quenched with water and extracted with EtOAc. Organic layer was dried over Na$_2$SO$_4$, filtered and concentrated to give a crude diastereomeric mixture. This was purified by column chromatography on silica gel (100-200 mesh).

Elution with 15% EtOAc in petroleum ether provides the first eluting hydroxyl center diastereomer and 40% EtOAc in petroleum ether gave the other diastereomer, target #33 (72 mg, 14%) and hydroxy center diastereomer (17 mg, 3%). $R_f$: 0.5 (other diastereomer) and 0.7 (#33) (EtOAc).

Example 33

6-{(5S)-2-oxo-5-[(1S)-2,2,2-trifluoro-1-hydroxy-ethyl]pyrrolidin-1-yl}isoquinoline-1-carbonitrile (Stereochemistry Arbitrarily Assigned)

LCMS m/z=336.0 (M+1). $^1$H NMR (400 MHz, $d_6$-DMSO) δ 1.98-2.17 (m, 1H); 2.39-2.46 (m, 2H); 2.5-2.77 (m, 1H); 4.23-4.30 (m, 1H); 4.99 (t, J=7.2 Hz, 1H); 6.70 (d, J=6.3 Hz, 1H); 8.11-8.25 (m, 3H); 8.29 (d, J=2.1 Hz, 1H); 8.65 (d, J=5.7 Hz, 1H).

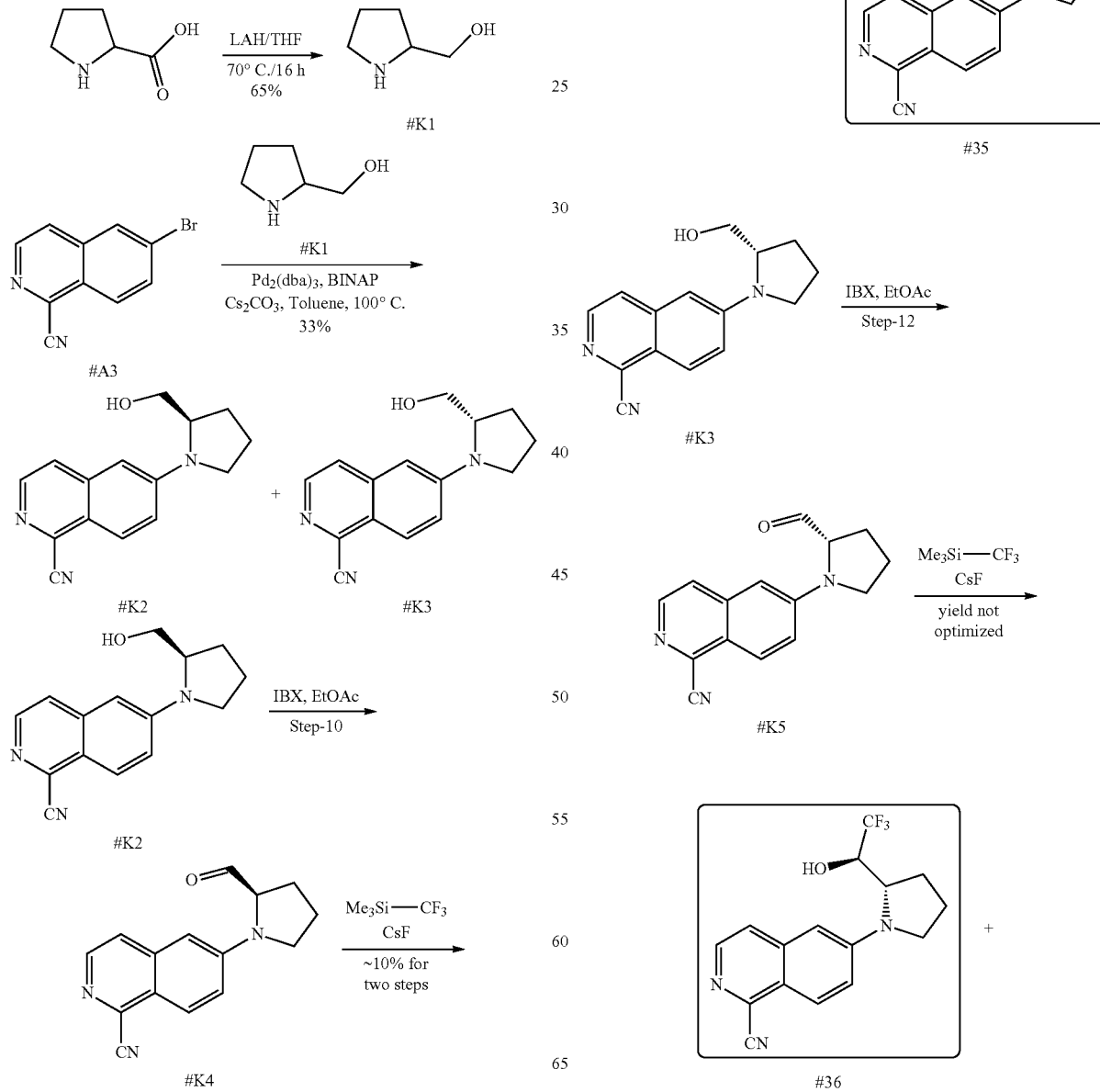
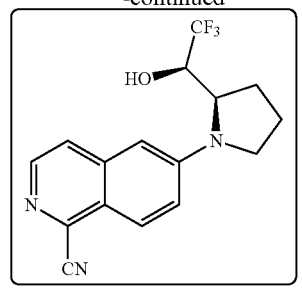
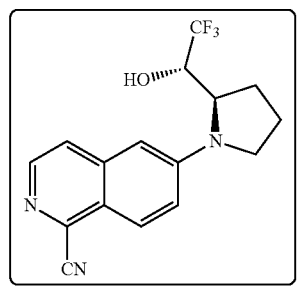
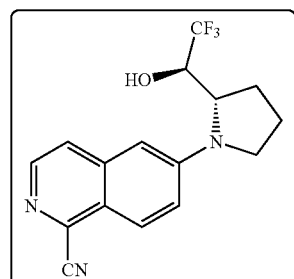

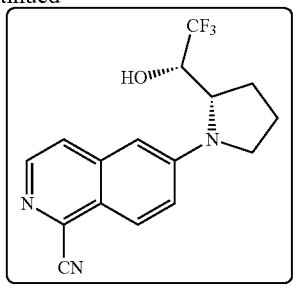

37

Step 1. Preparation of amino alcohol (#K1). DL-Proline (6.0 g, 52.0 mmol) was added slowly and portion wise to a stirred suspension of LiAlH₄ (3.0 g, 78.0 mmol) in THF (80 mL) at 0° C. under nitrogen atmosphere carefully over a period of 30 minutes. The reaction mixture was warmed to room temperature and then heated to reflux for 3 h. The mixture was quenched with 20% KOH solution at 0° C. slowly (18-20 mL). The mixture was filtered through a Celite™ pad and washed ith THF. The filtered precipitate was again refluxed with THF for 30 minutes and filtered. The combined filtrates were concentrated to give #K1 as pale yellow liquid which is slowly converts to dark brown liquid (3.2 g, 65%). $R_f$: 0.1 (10% MeOH in DCM & 1 drop AcOH, ninhydrin active).

Step 2. Synthesis of coupling products (#K2, #K3). Pd₂(dba)₃ (350 mg, 0.06 mmol), BINAP (790.0 mg, 0.2 mmol), Cs₂CO₃ (6.2 g, 3.0 mmol) were added to a mixture of 6-bromoisoquinoline-1-carbonitrile #A3 (1.5 g, 6.4 mmol) and #K1 (1.3 g, 12.8 mmol) in toluene (10 mL) under nitrogen atmosphere. The reaction mixture was heated to 110° C. for 3 h. The mixture was diluted with EtOAc and washed with water and brine solution. Organic layer was dried over Na₂SO₄ and concentrated to give crude material. The crude material was purified by column chromatography on silica gel (100-200 mesh) eluted with 40% EtOAc in petroleum ether to give racemic material (#K2, #K3, 1 g, 33%). The isomers were separated by chiral preparative HPLC to give #K2 (500 mg) and #K3 (450 mg). $R_f$: 0.2 (EtOAc).

Step 3. Synthesis of aldehyde (#K4). IBX (1.5 g, 5.5 mmol) was added to a stirred solution of #K2 (0.7 g, 2.7 mmol) in EtOAc (15 mL) at room temperature. The reaction mixture was heated to 80° C. for 3 h. The mixture was filtered through a Celite™ pad and washed with EtOAc. The collected organic layers were washed with saturated aqueous NaHCO₃ solution, dried over Na₂SO₄, filtered and concentrated to get crude #K4 (1 g crude) as a yellow liquid. The crude compound was used for next step without further purification. $R_f$: 0.7 (EtOAc).

Step 4. Synthesis of products (#34, #35). Me₃SiCF₃ (0.6 g, 4.7 mmol) was added dropwise to a stirred suspension of #K4 (1.0 g, 4.0 mmol) and CsF (3.0 g, 19.7 mmol) in THF at −78° C. very slowly. The reaction mixture was allowed to warm to room temperature and stirred overnight. The mixture was quenched with water and extracted with EtOAc. Organic layer was dried over Na₂SO₄, filtered and concentrated to give the crude diastereomeric mixture. This was purified by column chromatography on) silica gel (100-200 mesh eluting with 15% EtOAc in petroleum ether to give diastereomer #34 and 30% EtOAc in pet ether to give diastereomer #35. Yield of #34 (66 mg, 6%) and #35 (72 mg, 7%) as pale yellow solids. $R_f$: 0.5 (#34) and 0.7 (#35) (EtOAc).

Example 34

6-{(2R)-2-[(1R)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). ¹H NMR (300 MHz, d₆-DMSO): δ 1.90-2.10 (m, 2H); 2.18-2.43 (m, 2H); 3.43-3.53 (m, 1H); 3.57-3.65 (m, 1H); 4.32 (t, 2H); 6.50 (d, J=9.6 Hz, 1H); 6.89 (d, J=3.6 Hz, 1H); 7.41 (d, J=6.8 Hz, 1H); 7.85 (d, J=6.0 Hz, 1H); 8.06 (d, J=9.6 Hz, 1H); 8.38 (d, J=6.0 Hz, 1H).

Example 35

6-{(2R)-2-[(1S)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). ¹H NMR (300 MHz, d₆-DMSO): δ 1.96-2.15 (m, 1H); 3.30 (t, J=12.4 Hz, 1H); 3.56 (t, J=7.6 Hz, 1H); 4.05-4.15 (m, 1H); 4.33 (d, J=5.2 Hz, 1H); 6.53 (d, J=6.4 Hz, 1H); 6.95 (d, J=2.0 Hz, 1H); 7.51 (d, J=7.2 Hz, 1H); 7.80 (d, J=6.0 Hz, 1H); 7.96 (d, J=9.6 Hz, 1H); 8.35 (d, J=6.0 Hz, 1H).

Step 5. Synthesis of aldehyde (#K5). IBX (1.1 g, 3.8 mmol) was added to a stirred solution of #K3 (0.5 g, 1.9 mmol) in EtOAc (10 mL) at room temperature. The reaction mixture was heated to reflux for 3 h. The mixture was filtered through a Celite™ pad and washed with EtOAc. The collected organic layers were washed with saturated aqueous NaHCO₃ solution, dried over Na₂SO₄, filtered and concentrated to give crude #K5 (0.5 g crude) as a pale yellow liquid. The crude compound was used in the next step without further purification. $R_f$: 0.7 (EtOAc).

Step 6. Synthesis of final compounds (#36, #37). Me₃SiCF₃ (0.34 g, 2.4 mmol) was added dropwise to a stirred suspension of aldehyde #K5 (0.5 g, 1.4 mmol) and CsF (1.5 g, 10.0 mmol) in THF (15 mL) at −78° C. very slowly. The reaction mixture was allowed to warm to room temperature and stirred overnight. The mixture was quenched with water and extracted with EtOAc. The organic layer was dried over Na₂SO₄ and concentrated to give crude diastereomeric mixture. This was purified by column chromatography on silica gel (100-200 mesh) eluted with 15% EtOAc in petroleum ether to give diastereomer #36 (22 mg, 4%) and 30% EtOAc in petroleum ether to give diastereomer #37 (33 mg, 6%) as pale brown solids. $R_f$: 0.5 (#36) and & 0.7 (#37) (EtOAc).

Example 36

6-{(2S)-2-[(1S)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). ¹H NMR (300 MHz, d₆-DMSO) δ 2.05 (m, 4H); 3.29-3.30 (m, 1H); 3.57 (m, 1H); 4.07-4.09 (m, 1H); 4.34 (s, 1H); 6.53 (d, J=1.8 Hz, 1H); 7.52 (dd, J=9.0 Hz, 1H); 7.80 (d, J=6.0 Hz, 1H); 7.96 (d, J=9.6 Hz, 1H); 8.36 (d, J=5.4 Hz, 1H).

Example 37

6-{(2S)-2-[(1R)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). ¹H NMR (300 MHz, d₆-DMSO) δ 1.95-2.04 (m, 2H), 2.18-2.32 (m, 2H); 3.36-3.40 (m, 1H);

3.58-3.61 (m, 1H); 4.29-4.38 (m, 2H); 6.5 (d, J=5.1 Hz, 1H); 6.89 (d, J=1.5 Hz, 1H); 7.40-7.43 (d, J=7.2 Hz, 1H); 7.85 (d, J=4.2 Hz, 1H); 8.06 (d, J=6.9 Hz; 1H); 8.38 (d, J=4.5 Hz, 1H).

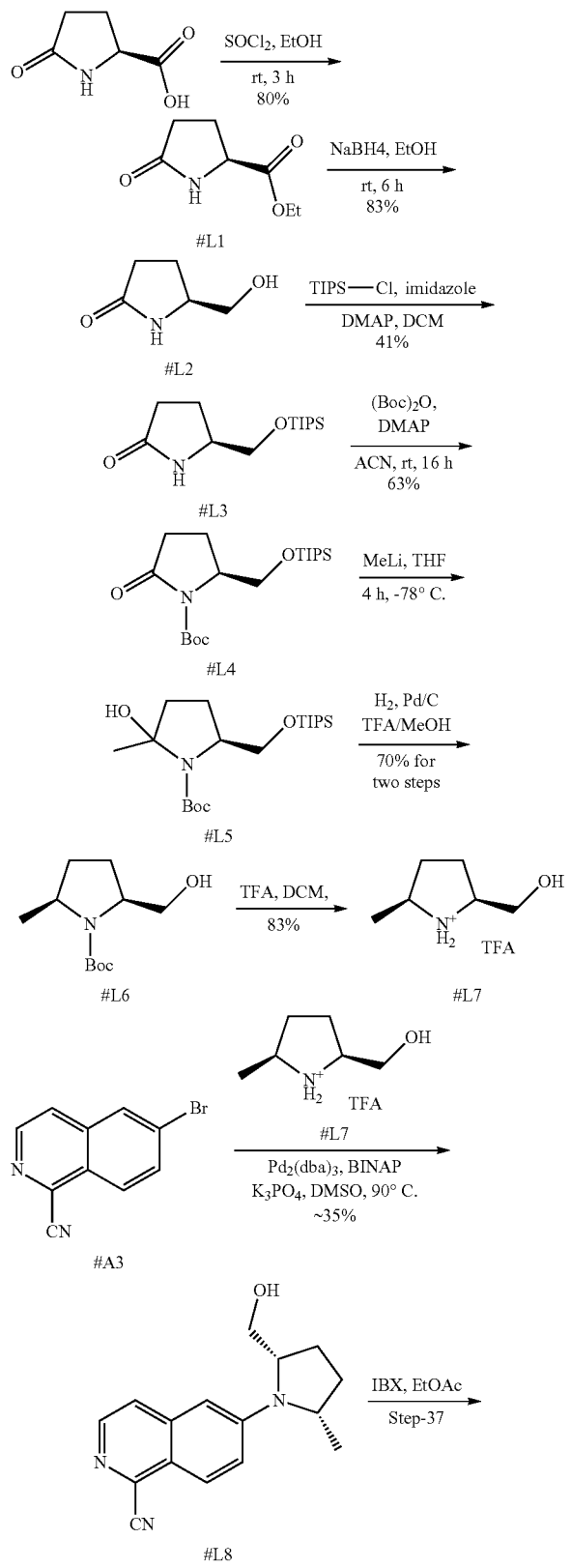

Step 1. Synthesis of ester (#L1). Thionyl chloride (11.2 mL, 154 mmol) was added to a solution of acid (20.0 g, 155.0 mmol) in ethanol (200 mL) at 0° C. slowly. The reaction mixture was allowed to stir at room temperature overnight. The mixture was concentrated in vacuo to remove ethanol. The crude residue was diluted with DCM, washed with saturated aqueous $NaHCO_3$ solution, water and brine. The organic layer was dried over $Na_2SO_4$ and concentrated to give #L1 (19 g, 80%) as yellow liquid. $R_f$: 0.3 in 100% EtOAc ($KMnO_4$ active).

Step 2. Synthesis of alcohol (#L2). $NaBH_4$ (1.7 g, 45.0 mmol) was added slowly to a solution of #L1 (12.0 g, 76.0 mmol) in ethanol (120 mL) at 0° C. portionwise. The reaction mixture was allowed to stir at room temperature for 6 h. After the reaction completion, the mixture was quenched with concentrated HCl and the precipitated solid was filtered. The crude compound was purified by column chromatography using silica gel (100-200 mesh) and eluted with 8% methanol in DCM to give pure #L2 (7.3 g, 83%) as pale yellow thick liquid. $R_f$: 0.1 (20% MeOH in DCM, $KMnO_4$ active).

Step 3. Synthesis of TIPS protected alcohol (#L3). Imidazole (11.8 g, 173.0 mmol) and DMAP (3.1 g, 26.0 mmol) were added to a stirred solution of #L2 (10.0 g, 87.0 mmol) in DCM at 0° C. followed by TIPS-Cl (27.8 mL, 130.0 mmol). The mixture was allowed to stir at room temperature for 16 h. After the starting material was consumed, the mixture was quenched with ice water and extracted with EtOAc. The organic layer was washed with brine, dried over $Na_2SO_4$, filtered and concentrated to give crude product which was purified by column chromatography on silica gel (100-200 mesh) eluted with 20% EtOAc in petroleum ether to give pure #L3 (10.0 g, 31%) as pale yellow liquid. $R_f$: 0.3 (50% EtOAc in petroleum ether, $KMnO_4$ active).

Step 4. Synthesis of N-Boc TIPS protected alcohol (#L4). $(Boc)_2O$ (4.5 mL, 20.5 mmol) was added to a stirred solution of #L3 (5.0 g, 18.0 mmol) and DMAP (0.5 g, 4.0 mmol) in acetonitrile (40 mL) at −30° C. The reaction mixture was stirred for 30 minutes and then continued at room temperature for 16 h. The reaction mixture was concentrated under reduced pressure to give a crude product which was purified by column chromatography on silica gel (100-200 mesh) using 10% EtOAc and petroleum ether to afford #H4 (4.5 g, 66%) as a light brown liquid. $R_f$: 0.6 (30% EtOAc/petroleum ether, $KMnO_4$ active).

Step 5. Synthesis of methylated N-Boc TIPS protected alcohol (#L5). MeLi (3 M in diethylamine, 2.6 mL, 8.1 mmol) was added dropwise to a solution of #L4 (3.0 g, 8.1 mmol) in dry THF (20 mL) at −78° C. and stirring was continued at same at temperature for 4 h. The reaction mixture was quenched with saturated aqueous NH$_4$Cl solution, extracted with EtOAc, dried over Na$_2$SO$_4$ and concentrated to give #L5 (3 g, 96%) as a light brown liquid which was used in next step without further purification. R$_f$: 0.2 (30% EtOAc in petroleum ether, KMnO$_4$ active).

Step 6. Synthesis of N-Boc alcohol (#H6). A mixture of #L5 (3.5 g, 9.0 mmol) and 10% Pd/C (1.2 g) in 10% trifluoroacetic acid in methanol (80 mL) was shaken in a Parr apparatus under a hydrogen atmosphere at 200 psi at room temperature for 24 h. The reaction mixture was filtered through a Celite™ pad, washed with EtOAc, concentrated under reduced pressure to provide crude product. This was purified by column chromatography on silica gel (100-200 mesh) using 15% EtOAc/petroleum ether to get #L6 (2 g, 60%) as a yellow liquid. R$_f$: 0.4 (30% EtOAc: petroleum ether, KMnO$_4$ active).

Step 7. Synthesis of amino alcohol trifluoroacetic acid salt (#L7). Trifluoroacetic acid (10.0 mL) was added dropwise to a solution of #H6 (1.0 g, 4.6 mmol) in DCM (10 mL) at room temperature, and the reaction mixture was stirred for 2 h. The solvents were evaporated under reduced pressure to get residue mixture which was co-distilled with methanol and concentrated under reduced pressure to afford #L7 (1 g, 94%) as a pale yellow liquid. R$_f$: 0.2 (20% methanol in DCM, KMnO$_4$ active).

Step 8. Synthesis of product (#L8). Pd$_2$(dba)$_3$ (235.0 mg, 0.25 mmol), BINAP (480.0 mg, 0.77 mmol), K$_3$PO$_4$ (1.9 g, 9.0 mmol) were added to a mixture of 6-bromoisoquinoline-1-carbonitrile (600.0 mg, 2.57 mmol) and #L7 (1 g, 4.1 mmol) in DMSO (5 mL) under nitrogen atmosphere. The reaction mixture was heated to 110° C. for 3 h. The mixture was diluted with EtOAc and washed with water and brine. Organic layer was dried over Na$_2$SO$_4$ and concentrated to give crude compound. The crude material was purified by column chromatography using silica gel (100-200 mesh) eluted with 40% EtOAc in petroleum ether to get pure #L8 (400 mg, 58%) as pale yellow solid. R$_f$: 0.4 (50% EtOAc in petroleum ether).

LCMS m/z=268.2 (M+1).

Step 9. Synthesis of aldehyde (#L9). IBX (800.0 mg, 2.9 mmol) was added to a stirred solution #L8 (400 mg, 1.45 mmol) in EtOAc (10 mL) at room temperature. The reaction mixture was heated to 80° C. for 3 h. The mixture was filtered through a Celite™ pad and washed with EtOAc. The filtrate was washed with saturated aqueous NaHCO$_3$ solution, dried over Na$_2$SO$_4$, filtered and concentrated to give #L9 (400 mg crude) as a pale yellow solid. The crude compound was used in the next step without further purification. R$_f$: 0.5 (50% EtOAc in petroleum ether).

Step 10. Synthesis of product (#38). Me$_3$SiCF$_3$ (300.0 mg, 2.1 mmol) was added dropwise to a stirred suspension of #L9 (400 mg, 1.5 mmol) and CsF (1.2 g, 8 mmol) in THF (10 mL) at −78° C. very slowly. The reaction mixture was stirred at room temperature overnight. The mixture was quenched with water and extracted with EtOAc. The organic layer was dried over Na$_2$SO$_4$, filtered and concentrated to give a crude diastereomeric mixture. Purification by column chromatography on silica gel (230-400 mesh) and elution with 10% EtOAc in petroleum ether provided hydroxy center diastereomer (75 mg, 15%) as a pale brown solid. Further elution with 20% EtOAc in petroleum ether gave hydroxy center diastereomer #38 (60 mg, 12%) as off white solids. R$_f$: 0.6 (hydroxyl center diastereomer) and 0.7 (#38) (50% EtOAc in pet ether).

Example 38

6-{(2S,5S)-2-methyl-5-[(1S)-2,2,2-trifluoro-1-hydroxyethyl]pyrrolidin-1-yl}isoquinoline-1-carbonitrile (Stereochemistry Arbitrarily Assigned)

LCMS m/z=336.2 (M+1). $^1$H NMR (400 MHz, d$_6$-DMSO) δ 1.36 (d, J=6.3 Hz, 3H); 1.79-1.93 (m, 3H); 2.27 (s, 1H); 3.97-4.03 (m, 2H); 4.29-4.26 (m, 1H); 6.64 (d, J=6.3 Hz; 1H); 7.04 (d, J=2.1 Hz; 1H); 7.56 (q, J=9.0 Hz, 9.9 Hz, 1H); 7.84 (d, J=5.4 Hz; 1H); 7.98 (d, J=9 Hz; 1H); 8.36 (d, J=5.4 Hz; 1H).

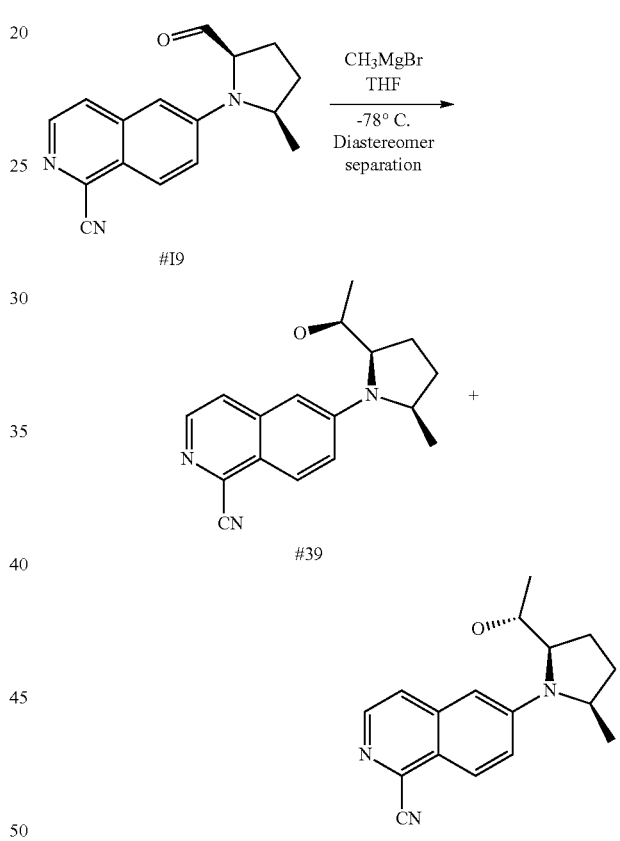

Step 1. Synthesis of final product (#39). Step 1. Synthesis of product (#17). [125536-36-1,4]. Methylmagnesium bromide (1.2 mL, 1.2 mmol) was added to #19 (0.30 g, 1.1 mmol) in dry THF (8 mL) at −78° C. The mixture warmed to −30° C. and stirred for 4 h. After consumption of starting material the mixture was quenched with saturated aqueous NH$_4$Cl solution and extracted with EtOAc. The organic layer was washed with brine, dried over Na$_2$SO$_4$, filtered and concentrated. This crude material was purified by column chromatography on silica gel (230-400 mesh). Elution with 20% EtOAc in pet ether gave (#39) (37 mg, 11%) as a pale brown solid. Further elution with 30% EtOAc in petroleum ether gave hydroxy center diastereomer (18 mg, 5%) as a pale brown solid. R$_f$: 0.4 (#39) and 0.2 (hydroxyl center diastereomer) (60% EtOAc in petroleum ether).

Example 39

6-{(2R,5R)-2-[(1S)-1-hydroxyethyl]-5-methylpyrrolidin-1-yl}isoquinoline-1-carbonitrile (Stereochemistry Arbitrarily Assigned)

LCMS m/z=282.1 (M+1). $^1$H NMR (300 MHz, d$_6$-DMSO) δ 1.14 (d, J=6.3 Hz, 3H); 1.30 (d, J=6.3 Hz, 3H); 1.17-1.83 (m, 2H); 2.01-2.07 (m, 1H); 2.07-2.27 (m, 1H); 3.82-3.85 (m, 1H); 3.97-4.04 (m, 2H); 4.73 (d, J=3.3 Hz, 1H); 6.9 (d, J=2.1 Hz, 1H); 7.43 (m, 1H); 7.82 (d, J=5.4 Hz, 1H); 7.96 (d, J=9.0 Hz, 1H); 8.30 (d, J=5.7 Hz, 1H).

The following examples are prepared using 2-bromo-5-cyanonaphthalene instead of 1-cyano-6-bromoisoquinoline:

Example 40

6-((2R,3S)-4,4,4-trifluoro-3-hydroxybutan-2-ylamino)-1-naphthonitrile

Example 41

6-((R)-2-((R)-2,2,2-trifluoro-1-hydroxyethyl)azetidin-1-yl)-1-naphthonitrile

Example 42

6-((S)-2-((S)-2,2,2-trifluoro-1-hydroxyethyl)azetidin-1-yl)-1-naphthonitrile

Example 43

6-(methyl((2R,3R)-4,4,4-trifluoro-3-hydroxybutan-2-yl)amino)-1-naphthonitrile

Example 44

6-(methyl((2R,3S)-4,4,4-trifluoro-3-hydroxybutan-2-yl)amino)-1-naphthonitrile

Example 45

6-((R)-2-((R)-2,2,2-trifluoro-1-hydroxyethyl)piperidin-1-yl)-1-naphthonitrile

Example 46

6-((R)-2-((S)-2,2,2-trifluoro-1-hydroxyethyl)piperidin-1-yl)-1-naphthonitrile

Example 47

6-((2R,5R)-2-methyl-5-((R)-2,2,2-trifluoro-1-hydroxyethyl)pyrrolidin-1-yl)-1-naphthonitrile

Example 48

6-((2R,5R)-2-((R)-1-hydroxyethyl)-5-methylpyrrolidin-1-yl)-1-naphthonitrile

Example 49

6-((R)-2-oxo-5-((S)-2,2,2-trifluoro-1-hydroxyethyl)pyrrolidin-1-yl)-1-naphthonitrile

Example 50

6-((S)-2-oxo-5-((S)-2,2,2-trifluoro-1-hydroxyethyl)pyrrolidin-1-yl)-1-naphthonitrile

Example 51

6-((R)-2-((R)-2,2,2-trifluoro-1-hydroxyethyl)pyrrolidin-1-yl)-1-naphthonitrile

Example 52

6-((R)-2-((S)-2,2,2-trifluoro-1-hydroxyethyl)pyrrolidin-1-yl)-1-naphthonitrile

Example 53

6-((S)-2-((S)-2,2,2-trifluoro-1-hydroxyethyl)pyrrolidin-1-yl)-1-naphthonitrile

Example 54

6-((S)-2-((R)-2,2,2-trifluoro-1-hydroxyethyl)pyrrolidin-1-yl)-1-naphthonitrile

Example 55

6-((2S,5S)-2-methyl-5-((S)-2,2,2-trifluoro-1-hydroxyethyl)pyrrolidin-1-yl)-1-naphthonitrile

Example 56

6-((2R,5R)-2-((S)-1-hydroxyethyl)-5-methylpyrrolidin-1-yl)-1-naphthonitrile

Androgen Receptor-Mediated Transcriptional Assay Summary

CV-1 cells (American Tissue Culture Collection cat# CCL-70) were expanded in Growth Media and transiently transfected in T225 cm$^2$ flasks with a full length human Androgen Receptor (AR) cDNA in the pcDNA3 expression vector and a human Androgen Response Element (ARE)-luciferase cDNA in the pGL3 vector (both from Invitrogen). DNA (μg) and Lipofectamine (μl) at a ratio of 1:3 were incubated with the cells in a total volume of 55 mL Basal Media for 4 hours. Cells were harvested by trypsinization and frozen back (−150° C. cryomed) at a concentration of 4.3 million cells/mL.

On the day of the assay, frozen cells were thawed and re-suspended in Re-suspension Media and plated at 40,000 cells/well (in 100 μL volume) in 96 well white plates and were incubated for at least 4 h at 37° C., 5% CO$_2$. After incubation, cells were treated with the compounds to be screened. 10 mM stocks of the compounds were serially diluted 1:10 in 100% DMSO followed by an additional 1:100 dilution in Assay Media. These dilution series were added to the cell plates resulting in a further 1:10 dilution and a final % DMSO of 0.1%. The vehicle control wells also contained this dilution of DMSO and the positive control wells contained Dihydroxytestosterone (DHT) as an AR agonist at final concentration of 0.3 nM in 0.1% DMSO. Cells were incubated for 16-18 hours at 37° C. and 5% $CO_2$. Then the culture media was removed from and the cells were lysed in 20 µL of cell lysis reagent for 5 minutes at room temperature. 50 µL of luciferase reagent was added to each well and luminescence, over 5 seconds, was measured. The $EC_{50}$ for each compound was calculated using the formulas shown below.

Formulas $EC_{50}$ (half maximal effective concentration) was calculated from concentration series plots which generated sigmoidal curves. Xlfit software was used to plot the best fit of the % effect vs concentration and to calculate the $EC_{50}$. Using this protocol, the results set forth in the Tables below were generated for the title compounds 1-39. The $IC_{50}$ values obtained suggest that the compounds of the present invention are effective in selectively modulating androgenic receptors, a key feature in many diseases affected by SARMs.

Reagents and Materials used in the Androgen Receptor-Mediated Transcriptional Assay include the following:
Growth Media—DMEM/high glucose—10% FBS: 500 ml phenol red DMEM/high glucose (Gibco, Grand Island N.Y., cat #10569-010), 10% non heat-inactivated Fetal Bovine Serum (FBS) (Atlanta Biologicals, Norcross Ga., cat #S-12450), 1% Nonessential Amino Acids (Gibco, cat #11140-050), 1% Penicillin-Streptomycin (Gibco, cat #15140-122)
Basal Media—phenol red free DMEM/high glucose (Gibco, cat #31053-028)+1% Na Pyruvate (Gibco, cat #11360-070), 1% Nonessential Amino Acids (Gibco, cat #11140-050), 1% GlutaMAX-I (Gibco, cat #35050-061)
Re-suspension Media—basal media+1% Penicillin-Streptomycin (Gibco, cat #15140-122)
Assay Media—basal media+5% charcoal stripped FBS (HyClone, Logan Utah, Cat #SH30068)+1% Penicillin-Streptomycin (Gibco, cat #15140-122)
Cell Lysis Reagent—Promega, Cat #PAE1531
Luciferase Reagent—Promega, Cat #PAE1483

TABLE 1

$EC_{50}$ Values for Compounds 1-22 from Androgen Receptor-Mediated Transcriptional Assay

| Compound # | $EC_{50}$, nM |
|---|---|
| 1 | 15 |
| 2 | 18 |
| 3 | 79 |
| 4 | 22 |
| 5 | 5 |
| 6 | 10 |
| 7 | 22 |
| 8 | 271 |
| 9 | 4 |
| 10 | 0.4 |
| 11 | 687 |
| 12 | 217 |
| 13 | 0.7 |
| 14 | 22 |
| 15 | 195 |
| 16 | 262 |
| 17 | 16 |
| 18 | 20 |
| 19 | 177 |
| 20 | 8 |
| 21 | 8 |
| 22 | 569 |

TABLE 2

$EC_{50}$ Values for Compounds 23-39 from Androgen Receptor-Mediated Transcriptional Assay

| Compound # | $EC_{50}$, nM |
|---|---|
| 23 | 5.1 |
| 24 | 9.6 |
| 24 | 383.2 |
| 26 | 0.1 |
| 27 | 12.9 |
| 28 | 61.5 |
| 29 | 0.02 |
| 30 | 0.1 |
| 31 | 473.9 |
| 32 | 84.3 |
| 33 | 231.3 |
| 34 | 0.1 |
| 35 | 7.4 |
| 36 | 120.2 |
| 37 | 9.1 |
| 38 | 187.0 |
| 39 | 37.3 |

What is claimed is:
1. A compound of Formula 1, 2 or 3:

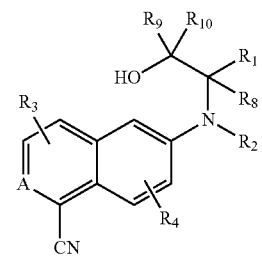

Formula 1

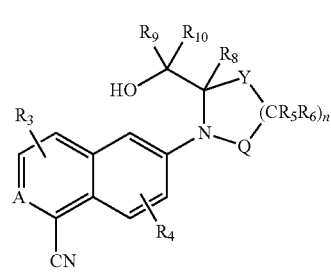

Formula 2

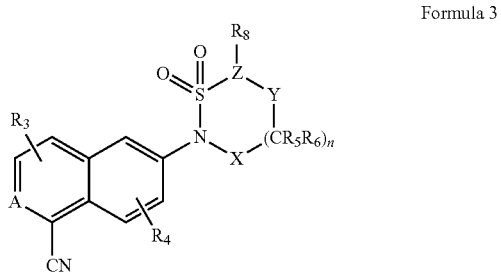

Formula 3 wherein A is N or —$CR_0$—, where $R_0$ is hydrogen, $C_1$-$C_6$ linear or branched chain alkyl, $C_1$-$C_6$ linear or branched chain perfluoroalkyl, aryl, perfluoroaryl, alkylaryl, heteroaryl; or, alkylheteroaryl X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl; or, $R_a$ and $R_b$ together form a chain comprising —$(CH_2)_j$—, —$(CHR_c)_j$—, or —$(CR_c$ $R_d)_j$—, where $R_c$ and $R_d$ are independently $C_1$-$C_6$ linear or branched chain alkyl, $C_1$-$C_6$ linear or branched chain perfluoroalkyl, aryl, alkylaryl, heteroaryl or alkylheteroaryl; where j is 2; 3, 4 or 5

Z is —$CR_e$—, —, or, —N—, where $R_e$ is hydrogen, $C_1$-$C_6$ linear or branched chain alkyl, $C_1$-$C_6$ linear or branched chain perfluoroalkyl, aryl, alkylaryl, heteroaryl or, alkylheteroaryl;

$R_1$ is hydrogen, $C_1$-$C_6$ linear or branched chain alkyl, aryl, $C_1$-$C_6$ linear or branched chain perfluoroalkyl, alkylaryl, heteroaryl, alkylheteroaryl, $C_1$-$C_6$ linear or branched chain alkoxylcarbonyl, $C_1$-$C_6$ linear or branched chain alkylamino-carbonylamino, $C_1$-$C_6$ linear or branched chain alkyloxycarbonylamino, $C_1$-$C_6$ linear or branched chain alkylcarbonylamino, or, $C_1$-$C_6$ linear or branched chain alkylaminocarbonyl;

$R_2$ are independently hydrogen or $C_1$-$C_6$ linear or branched chain alkyl;

$R_3$ and $R_4$ are independently hydrogen, $C_1$-$C_6$ linear or branched chain alkyl, $C_1$-$C_6$ linear or branched chain perfluoroalkyl, $C_1$-$C_6$ linear or branched chain perfluoroalkoxy, halogen, cyano, hydroxyl, amino, carboxy, hydroxyl, aryl, heteroaryl, $C_1$-$C_6$ linear or branched chain alkoxylcarbonyl, $C_1$-$C_6$ linear or branched chain alkylamino-carbonylamino, or, $C_1$-$C_6$ linear or branched chain alkylaminocarbonyl;

$R_5$ and $R_6$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_5$ and $R_6$ together form a chain comprising —$(CH_2)_k$—, —$(CHR_7)_k$—, or —$(CR_{7a}R_{7b})_k$—, where $R_7$, $R_{7a}$, and $R_{7b}$ are independently $C_1$-$C_6$ linear or branched chain alkyl, $C_1$-$C_6$ linear or branched chain perfluoroalkyl, aryl, alkylaryl, heteroaryl or alkylheteroaryl; where k is 2; 3, 4 or 5;

$R_8$ is hydrogen, $C_1$-$C_6$ linear or branched chain alkyl, $C_1$-$C_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising —$(CH_2)_m$—, —$(CHR_f)_m$—, or —$(CR_fR_g)_m$—, where $R_f$ and $R_g$ are independently $C_1$-$C_6$ linear or branched chain alkyl, aryl, alkylaryl, heteroaryl or alkylheteroaryl; where m is 2; 3, 4 or 5;

$R_9$ and $R_{10}$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_9$ and $R_{10}$ together form a chain comprising —$(CH_2)_p$—, —$(CHR_h)_p$—, or —$(CR_hR_i)_p$—, where $R_h$ and $R_i$ are independently $C_1$-$C_6$ linear or branched chain alkyl, aryl, alkylaryl, heteroaryl or alkylheteroaryl; where p is 2; 3, 4 or 5;

Q is —CO—, —$(CH_2)_q$—, —$(CHR_s)_q$—, or —$(CR_sR_t)_q$—, where $R_s$ and $R_t$ are independently $C_1$-$C_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof.

2. The compound of claim 1 having Formula 1 wherein $R_1$ and $R_2$ are independently $C_1$-$C_6$ linear or branched chain alkyl; and, $R_3$ and $R_4$ are both hydrogen.

3. The compound of claim 2 wherein $R_1$ and $R_2$ are independently methyl, ethyl or propyl.

4. The compound of claim 1 having Formula 2 wherein Q is —$(CH_2)_q$—, —$(CHR_s)_q$—, or —$(CR_sR_t)_q$—, where $R_s$ and $R_t$ are independently $C_1$-$C_6$ linear or branched chain alkyl; and, q is 1 or 2.

5. The compound of claim 4 wherein Q is —CO—.

6. The compound of claim 1 having Formula 3 wherein X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl.

7. The compound of claim 6 wherein X and Y are independently —$CH_2$—, —$CHR_a$—, or, —$CR_aR_b$—, where $R_a$ and $R_b$ are independently methyl, ethyl.

8. The compound of claim 1 selected from the group consisting of:
- 6-[(3S)-3-methyl-1,1-dioxido-1,2,5-thiadiazolidin-2-yl]isoquinoline-1-carbonitrile;
- 6-[(3S)-3-ethyl-1,1-dioxido-1,2,5-thiadiazolidin-2-yl]isoquinoline-1-carbonitrile
- 6-[(3R)-1,1-dioxido-3-(2,2,2-trifluoroethyl)-1,2,5-thiadiazolidin-2-yl]isoquinoline-1-carbonitrile;
- 6-[(3R)-1,1-dioxido-3-(2-phenylethyl)-1,2,5-thiadiazolidin-2-yl]isoquinoline-1-carbonitrile;
- 6-[1-methyl-(3S)-3-methyl-1,1-dioxido-1,2,5-thiadiazolidin-2-yl]isoquinoline-1-carbonitrile;
- 6-{(3R)-1,1-dioxido-3-[3-(trifluoromethyl)phenyl]-1,2,5-thiadiazolidin-2-yl}isoquinoline-1-carbonitrile;
- 6-[(3S)-3-(4-chlorophenyl)-1,1-dioxido-1,2,5-thiadiazolidin-2-yl]isoquinoline-1-carbonitrile;
- 6-[(3S)-3-methyl-1,1-dioxido-1,2-thiazolidin-2-yl]isoquinoline-1-carbonitrile;
- 6-[(3S)-3-methyl-1,1-dioxido-1,2,5-thiadiazolidin-2-yl]naphthalene-1-carbonitrile;
- 6-[(4R)-4-methyl-1,1-dioxido-1,2,6-thiadiazinan-2-yl]isoquinoline-1-carbonitrile;
- 6-[(4S)-4-methyl-1,1-dioxido-1,2,6-thiadiazinan-2-yl]isoquinoline-1-carbonitrile;
- 6-{(3R)-1,1-dioxido-3-(3-phenyl)-1,2,5-thiadiazolidin-2-yl}isoquinoline-1-carbonitrile;
- 6-(4,4-dimethyl-1,1-dioxido-1,2,6-thiadiazinan-2-yl)isoquinoline-1-carbonitrile;
- 6-(6,6-dioxido-6-thia-5,7-diazaspiro[2.5]oct-5-yl)isoquinoline-1-carbonitrile;
- 6-[(4R)-4-(3-methylbenzyl)-1,1-dioxido-1,2,6-thiadiazinan-2-yl]isoquinoline-1-carbonitrile;
- 6-[(4R)-6-ethyl-4-methyl-1,1-dioxido-1,2,6-thiadiazinan-2-yl]isoquinoline-1-carbonitrile;
- 6-(5-methyl-1,1-dioxido-1,2,6-thiadiazinan-2-yl)isoquinoline-1-carbonitrile;
- 6-[(4S)-4-(4-methylphenyl)-1,1-dioxido-1,2,6-thiadiazinan-2-yl]isoquinoline-1-carbonitrile;
- 6-[(4R)-4-(4-methylphenyl)-1,1-dioxido-1,2,6-thiadiazinan-2-yl]isoquinoline-1-carbonitrile;
- 6-[(4S)-4-(3-methylphenyl)-1,1-dioxido-1,2,6-thiadiazinan-2-yl]isoquinoline-1-carbonitrile;
- 6-[(4S)-4-ethyl-1,1-dioxido-1,2,6-thiadiazinan-2-yl]isoquinoline-1-carbonitrile; and,
- 6-(1,1-dioxido-4-propyl-1,2,6-thiadiazinan-2-yl)isoquinoline-1-carbonitrile,
- 6-{[(2R,3S)-4,4,4-trifluoro-3-hydroxybutan-2-yl]amino}isoquinoline-1-carbonitrile;
- 6-{(2R)-2-[(1R)-2,2,2-trifluoro-1-hydroxyethyl]azetidin-1-yl}isoquinoline-1-carbonitrile;
- 6-{(2S)-2-[(1S)-2,2,2-trifluoro-1-hydroxyethyl]azetidin-1-yl}isoquinoline-1-carbonitrile;
- 6-{methyl-[(2R,3R)-4,4,4-trifluoro-3-hydroxybutan-2-yl]amino}isoquinoline-1-carbonitrile;
- 6-{methyl-[(2R,3S)-4,4,4-trifluoro-3-hydroxybutan-2-yl]amino}isoquinoline-1-carbonitrile;
- 6-{(2R)-2-[(1R)-2,2,2-trifluoro-1-hydroxyethyl]piperidin-1-yl}isoquinoline-1-carbonitrile;

6-{(2R)-2-[(1S)-2,2,2-trifluoro-1-hydroxyethyl]piperidin-1-yl}isoquinoline-1-carbonitrile;
6-{(2R,5R)-2-methyl-5-[(1R)-2,2,2-trifluoro-1-hydroxyethyl]pyrrolidin-1-yl}isoquinoline-1-carbonitrile;
6-{(2R,5R)-2-[(1R)-1-hydroxyethyl]-5-methylpyrrolidin-1-yl}isoquinoline-1-carbonitrile;
6-{(5R)-2-oxo-5-[(1S)-2,2,2-trifluoro-1-hydroxyethyl]pyrrolidin-1-yl}isoquinoline-1-carbonitrile;
6-{(5S)-2-oxo-5-[(1S)-2,2,2-trifluoro-1-hydroxyethyl]pyrrolidin-1-yl}isoquinoline-1-carbonitrile;
6-{(2R)-2-[(1R)-2,2,2-trifluoro-1-hydroxyethyl]pyrrolidin-1-yl}isoquinoline-1-carbonitrile;
6-{(2R)-2-[(1S)-2,2,2-trifluoro-1-hydroxyethyl]pyrrolidin-1-yl}isoquinoline-1-carbonitrile;
6-{(2S)-2-[(1S)-2,2,2-trifluoro-1-hydroxyethyl]pyrrolidin-1-yl}isoquinoline-1-carbonitrile;
6-{(2S)-2-[(1R)-2,2,2-trifluoro-1-hydroxyethyl]pyrrolidin-1-yl}isoquinoline-1-carbonitrile;
6-{(2S,5S)-2-methyl-5-[(1S)-2,2,2-trifluoro-1-hydroxyethyl]pyrrolidin-1-yl}isoquinoline-1-carbonitrile;
6-{(2R,5R)-2-[(1S)-1-hydroxyethyl]-5-methylpyrrolidin-1-yl}isoquinoline-1-carbonitrile;
6-((2R,3S)-4,4,4-trifluoro-3-hydroxybutan-2-ylamino)-1-naphthonitrile;
6-((R)-2-((R)-2,2,2-trifluoro-1-hydroxyethyl)azetidin-1-yl)-1-naphthonitrile;
6-((S)-2-((S)-2,2,2-trifluoro-1-hydroxyethyl)azetidin-1-yl)-1-naphthonitrile
6-(methyl((2R,3R)-4,4,4-trifluoro-3-hydroxybutan-2-yl)amino)-1-naphthonitrile;
6-(methyl((2R,3S)-4,4,4-trifluoro-3-hydroxybutan-2-yl)amino)-1-naphthonitrile;
6-((R)-2-((R)-2,2,2-trifluoro-1-hydroxyethyl)piperidin-1-yl)-1-naphthonitrile;
6-((R)-2-((S)-2,2,2-trifluoro-1-hydroxyethyl)piperidin-1-yl)-1-naphthonitrile;
6-((2R,5R)-2-methyl-5-((R)-2,2,2-trifluoro-1-hydroxyethyl)pyrrolidin-1-yl)-1-naphthonitrile;
6-((2R,5R)-2-((R)-1-hydroxyethyl)-5-methylpyrrolidin-1-yl)-1-naphthonitrile;
6-((R)-2-oxo-5-((S)-2,2,2-trifluoro-1-hydroxyethyl)pyrrolidin-1-yl)-1-naphthonitrile;
6-((S)-2-oxo-5-((S)-2,2,2-trifluoro-1-hydroxyethyl)pyrrolidin-1-yl)-1-naphthonitrile;
6-((R)-2-((R)-2,2,2-trifluoro-1-hydroxyethyl)pyrrolidin-1-yl)-1-naphthonitrile;
6-((R)-2-((S)-2,2,2-trifluoro-1-hydroxyethyl)pyrrolidin-1-yl)-1-naphthonitrile;
6-((S)-2-((S)-2,2,2-trifluoro-1-hydroxyethyl)pyrrolidin-1-yl)-1-naphthonitrile;
6-((S)-2-((R)-2,2,2-trifluoro-1-hydroxyethyl)pyrrolidin-1-yl)-1-naphthonitrile;
6-((2S,5S)-2-methyl-5-((S)-2,2,2-trifluoro-1-hydroxyethyl)pyrrolidin-1-yl)-1-naphthonitrile; and,
6-((2R,5R)-2-((S)-1-hydroxyethyl)-5-methylpyrrolidin-1-yl)-1-naphthonitrile, or, a pharmaceutically acceptable salt thereof.

9. The compound of claim 1 comprising 6-[(3R)-3-methyl-1,1-dioxido-1,2,5-thiadiazolidin-2-yl]isoquinoline-1-carbonitrile, or a pharmaceutically acceptable salt thereof.

10. The compound of claim 1 comprising 6-[(3S)-3-methyl-1,1-dioxido-1,2,5-thiadiazolidin-2-yl]isoquinoline-1-carbonitrile, or a pharmaceutically acceptable salt thereof.

11. The compound of claim 1 comprising 6-[(4R)-4-methyl-1,1-dioxido-1,2,6-thiadiazinan-2-yl]isoquinoline-1-carbonitrile, or a pharmaceutically acceptable salt thereof.

12. The compound of claim 1 comprising 6-[(4S)-4-methyl-1,1-dioxido-1,2,6-thiadiazinan-2-yl]isoquinoline-1-carbonitrile, or a pharmaceutically acceptable salt thereof.

13. The compound of claim 1 comprising 6-(methyl-((2R,3R)-4,4,4-trifluoro-3-hydroxybutan-2-yl)amino)-1-naphthonitrile, or a pharmaceutically acceptable salt thereof.

* * * * *